US007476500B1

(12) United States Patent
Liu et al.

(10) Patent No.: US 7,476,500 B1
(45) Date of Patent: Jan. 13, 2009

(54) IN VIVO SELECTION SYSTEM FOR ENZYME ACTIVITY

(75) Inventors: David R. Liu, Lexington, MA (US); Zev Gartner, Somerville, MA (US); Daniel M. Rosenbaum, Cambridge, MA (US); Mathias Gruen, Jena (DE); Jeffrey Doyon, Allston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 10/102,056

(22) Filed: Mar. 19, 2002

Related U.S. Application Data

(60) Provisional application No. 60/277,094, filed on Mar. 19, 2001, provisional application No. 60/306,691, filed on Jul. 20, 2001, provisional application No. 60/353,565, filed on Feb. 1, 2002.

(51) Int. Cl.
*C12Q 1/68* (2006.01)
*C12N 9/22* (2006.01)
(52) U.S. Cl. .......................................... 435/6; 435/199
(58) Field of Classification Search ................ 435/440, 435/29, 4
See application file for complete search history.

(56) References Cited

U.S. PATENT DOCUMENTS

2002/0094516 A1* 7/2002 Calos et al. ..................... 435/4

OTHER PUBLICATIONS

Altamirano, et al., "Directed Evolution of New Catalytic Activity Using the α/β-Barrell Scaffold" *Nature*, 403: 617-622, 2000.
Atwell, et al., "Structural Plasticity in a Remodeled Protein-Protein Interface" *Science*, 278: 1125-1128, 1997.
Axe, et al., "Active Barnase Variants with Completely Random Hydrophobic Cores" *Proc. Natl. Acad. Sci. USA*, 93: 5590-5594, 1996.
Ayers, et al., "Introduction of Unnatural Amino Acids into Proteins Using Expressed Protein Ligation" *Biopolymers*, 51: 343-354, 1999.
Belfort, et al., "Homing Endonucleases: Keeping the House in Order" *Nucleic Acids Res.* 25: 3379-3388. 1997.
Beylot, et al., "Chemical Probing Shows that the Intron-Encoded Endonuclease I-SecI Distorts DNA Through Binding in Monomeric Form to Its Homing Site" *J. Biol. Chem.* 276: 25243-25253, 2001.
Blaschke, et al., "Protein Engineering by Expressed Protein Ligation" *Methods Enzymol.* 328: 478-496, 2000.
Bornscheuer, et al., "Directed Evolution of an Esterase: Screening of Enzyme Libraries Based on pH-Indicators and a Growth Assay" *Bioorg Med. Chem.* 7: 2169-2173, 1999.
Chen, et al., "Crystal Structural of Flp Recombinase-Holliday Junction Complex: Assembly of an Active Oligomer by Helix Swapping" *Mol. Cell*, 6: 885-897, 2000.
Chevalier, et al., "Homing Endonucleases: Structural and Functional Insight into the Catalysts of Intron/Intein Mobility" *Nucleic Acids Res.* 29: 3757-3774, 2001.

Chong, et al., "Single-Column Purification of Free Recombinant Proteins using a Self-Cleavable Affinity Tag Derived from a Protein Splicing Element" *Gene*, 192: 271-281, 1997.
Christ, et al., "The Monomeric Homing Endonuclease PI-Scel has Two Catalytic Centres for Cleavage of the Two Strands of its DNA Substrate" *EMBO, J.* 18: 6908-6916, 1999.
Clackson, et al., "Structural and Functional Analysis of the 1:1 Growth Hormone: Receptor Complex Reveals the Molecular Basis for Receptor Affinity" *J. Mol. Biol.* 277: 1111-1128, 1998.
Colleaux, et al., "Recognition and Cleavage Site of the Intron-Encoded Omega Transposase" *Proc. Natl. Acad. Sci.* 85: 6022-6026, 1988.
Copenhaver, et al., "RFLP and Physical Mapping with an rDNA-Specific Endonuclease Reveals that Nucleolus Organizer Regions of *Arabidopsis thaliana* Adjoin the Telomeres on Chromosomes 2 and 4" *Plant J.*, 9: 259-272, 1996.
Cupples, et al., "A Set of lacZ Mutations in *Escherichia coli* that Allow Rapid Detection of Each of the Six Base Substitutions" *Proc. Natl. Acad. Sci, USA*, 86: 5345-5349, 1989.
Daugelat, et al., "The Mycobacterium Tuberculosis recA Intein Can be Used in an ORFTRAP to Select for Open Reading Frames" *Protein Sci.*, 8: 644-653, 1999.
DeDecker, "Allosteric Drugs: Thinking Outside the Active-Site Box" *Chem. Biol.* 7: R103-R107, 2000.
Evans, et al., "Intein-Mediated Protein Ligation: Harnessing Nature's Escape Artists" *Biopolymers*, 51: 333-342, 1999.
Evans, et al., "The Cyclization and Polymerization Bacterially Expressed Proteins Using Modified Self-Splicing Inteins" *J. Biol. Chem.* 274: 18359-18363, 1999.
Famulok, et al., "Oligonucleotide Libraries—Variatio Delectat" *Curr. Opin. Chem. Biol.* 2: 320-327, 1998.
Fiering, et al., "Analysis of Mammalian Cis-Regulatory DNA Elements by Homologous Recombination" *Methods Enzymol.* 306: 42-66, 1999.
Fong, et al., "Directed Evolution of D-2-Keto-3-Deoxy-6-Phosphogluconate Aldolase to New Variants for the Efficient Synthesis of D- and L-Sugars" *Chem. Biol.* 7: 873-883, 2000.
Foster, et al., "Pharmacological Rescue of Mutant p53 Conformation and Function" *Science*, 286: 2507-2510, 1999.
Freire, "The Propagation of Binding Interactions to Remote Sites in Proteins: Analysis of the Binding of the Monoclonal Antibody D1.3 to Lysozyme" *Proc. Natl. Acad. Sci, USA*, 96: 10118-10122, 1999.
Gimble, "Putting Protein Splicing to Work" *Chem. Biol.* 5: R251-256, 1998.
Giver, et al., "Combinatorial Protein Design by in Vitro Recombination" *Curr Opin. Chem. Biol.* 2:335-338, 1998.

(Continued)

*Primary Examiner*—Nancy Vogel
(74) *Attorney, Agent, or Firm*—Choate, Hall & Stewart, LLP; Hunter Baker; K. Nicole Clouse

(57) ABSTRACT

The present invention provides in vivo systems in which activity of a biological cleavage enzyme, such as a site-specific recombinase, a homing endonuclease, or an intein, is linked to cell viability and therefore can be selected. The invention further provides methods of making cells in which the activity of a biological cleavage enzyme is linked to viability, as well as methods of identifying new biological cleavage enzymes, including enzymes having altered site specificity, using such cells.

45 Claims, 37 Drawing Sheets

OTHER PUBLICATIONS

Gopaul et al., "Structure and Mechanism in Site-Specific Recombination" *Curr. Opin. Struct. Biol.*, 9:14-20, 1999.

Gopaul, et al., "Structure of the Holliday Junction Intermediate in Cre-LoxP Site-Specific Recombination" *EMBO J*, 17: 4175-4187, 1998.

Gorham, et al., "Site-Specific Gene Targeting for Gene Expression in Eukaryotes" *Curr. Opin Biotechnol.* 11:455-460, 2000.

Guo, et al., "Structure of Cre Recombinase Complexed with DNA in a Site-Specific Recombination Synapse" *Nature*, 389: 40-46, 1997.

Guo, et al., "Asymmetric DNA Bending in the Cre-LoxP Site-Specific Recombination Synapse" *Proc. Natl. Acad. Sci. USA*, 96: 7143-7148, 1999.

Guo, et al., "Designing Small-Molecule Switches for Protein-Protein Interactions" *Science*, 288: 2042-2045, 2000.

Guzman, et al., "Tight Regulation, Modulation, and High-Level Expression by Vectors Containing the Arabinose $P_{BAD}$ Promoter" *J. Bacteriol.* 177: 4121-4130, 1995.

Harayama, "Artificial Evolution by Shuffling" *Trends Biotechnol.* 16:76-82, 1998.

Hart, et al., "Directed Evolution to Investigate Steric Control of Enzymatic Oxidosqualene Cyclization. an Isoleucine-to-Valine Mutation in Cycloartenol Synthase Allows Lanosterol and Parkeol Biosyntheis" *J. Am. Chem. Soc.*, 121: 9887-9888, 1999.

Hartley, et al., "Barnase and Barstar: Two Small Proteins to Fold and Fit Together" *Trends Biochem. Sci.* 14: 450-454, 1989.

Hartley, et al., "Expression of Its Cloned Inhibitor Permits Expression of a Cloned Ribonuclease" *J. Mol. Biol.* 202: 913-915, 1988.

He, et al., "Amino Acid Residues in Both the Protein Splicing and Endonuclease Domains of the PI-SceI Intein Mediate DNA Binding" *J. Biol. Chem.* 273: 4607-4615, 1998.

Hedstrom, et al., "Converting Trypsin to Chymotrypsin: The Role of Surface Loops" *Science*, 255: 1249-1253, 1992.

Holford, et al., "Adding "Splice" To Protein Engineering" *Structure*, 6: 951-956, 1998.

Hon, et al., "Structure of an Enzyme Required for Aminoglycoside Antibiotic Resistance Reveals Homology to Eukaryotic Protein Kinases" *Cell*, 89: 887-895, 1997.

Hoseki, et al., "Directed Evolution of Thermostable Kanamycin-Resistance Gene: A Convenient Selection Marker for *Thermus Thermophilus*" *J. BioChem.* (Tokyo), 126:951-956, 1999.

Iffland, et al., "Directed Molecular Evolution of Cytochrome *c* Peroxidase" *Biochemistry* 39: 10790-10798, 2000.

Jäschke, et al., "Evolution of DNA and RNA as Catalysts for Chemical Reactions" *Curr Opin. Chem. Biol.* 4: 257-262, 2000.

Jayaram, "The Cis-Trans Paradox of Integrase" *Science*, 276: 49-51, 1997.

Jelsch, et al., "Crystal Structure of *Escherichia Coli* TEM1 β-Lactamase at 1.8 Å Resolution" Proteins, 16: 364-383, 1993.

Jucovic, et al., "In Vivo System for the Detection of Low Level Activity Barnase Mutants" *Protein Eng.*, 8: 497-499, 1995.

Jürgens, et al., "Directed Evolution of a (βα)$_8$-Barrel Enzyme to Catalyze Related Reactions in Two Different Metabolic Pathways" *Proc. Natl. Acad.Sci. USA*, 97: 9925-9930, 2000.

Jurica, et al., "Horning Endonucleases: Structure, Function and Evolution" *Cell. Mol. Life Sci*, 55: 1304-1326, 1999.

Krantz, "Diversification of the Drug Discovery Process" *Nat Biotechnol.* 16: 1294, 1998.

Kuchner, et al., "Directed Evolution of Enzyme Catalysts" *Trends Biotechnol.* 15: 523-530, 1997.

Kumamaru, et al., "Enhanced Degradation of Polychlorinated Biphenyls by Directed Evolution of Biphenyl Dioxygenase" *Nat. Biotechnol.* 16: 663-666, 1998.

Kuzminov, et al., "Stability of Linear DNA in recA Mutant *Escherichia coli* Cells Reflects Ongoing Chromosomal DNA Degradation" *J. Bacteriol.* 179: 880-888, 1997.

Lanio, et al., "Towards the Design of Rare Cutting Restriction Endonucleases; Using Directed Evolution to Generate Variants of EcoRV Differing in Their Substrate Specificity by Two Orders of Magnitude" *J. Mol. Biol.* 283: 59-69, 1998.

Le, et al., "Conditional Gene Knockout Using Cre Recombinase" *Methods Mol. Biol.* 136: 477-485, 2000.

Lee, et al., "Role of Nucleotide Sequences of *lox*P Spacer Region in Cre-Mediated Recombination" *Gene*, 216: 55-65, 1998.

Lee, et al., "Fluorescence Assays for DNA Cleavage" *Methods Enzymol.* 278: 343-363, 1997.

Li, et al., "Using Molecular Beacons as a Sensitive Fluorescence Assay for Enzymatic Cleavage of Single-Stranded DNA" *Nucleic Acids Res.* 28: e52, 2000.

Liu, et al., "Engineering a tRNA and Aminoacyl-tRNA Synthetase for the Site-Specific Incorporation of Unnatural Amino Acids into Proteins in Vivo" *Proc. Natl. Acad. Sci. USA*, 94: 10092-10097, 1997.

Liu, et al., "Highly Plastic Chromosomal Organization in *Salmonella Typhi*" *Proc. Natl. Acad. Sci. USA*, 93: 10303-10308, 1996.

Liu, et al., "Protein-Splicing Intein: Genetic Mobility, Origin and Evolution" *Annu. Rev. Genet.* 34: 61-76, 2000.

Liu, et al., "Progress Toward the Evolution of an Organism with an Expanded Genetic Code" *Proc. Natl. Acad. Sci. USA*, 96: 4780-4785, 1999.

Liu, et al., Characterization of an 'Orthogonal' Suppressor tRNA Derived from *E. coli* tRNA$_2$$^{Gln}$ *Chem. Biol.* 4: 685-691, 1999.

Liu, et al., "The Univector Plasmid-Fusion System, A Method for Rapid Construction of Recombinant DNA Without Restriction Enzymes" *Curr. Biol.* 8: 1300-1309, 1998.

Luque, et al., "Structural Stability of Binding Sites: Consequences for Binding Affinity and Allosteric Effects" *Proteins, Suppl.* 4: 63-71, 2000.

Lyznik, et al., "Heat-Inducible Expression of FLP Gene in Maize Cells" *Plant J.* 8: 177-186, 1995.

Lyznik, et al., "FLP-Mediated Recombination of FRT Sites in the Maize Genome" *Nucleic Acids Res.* 24: 3784-3789, 1996.

Mahillon, et al., "New Ultrarare Restriction Site-Carrying Transposons for Bacterial Genomics" *Gene*, 187: 273-279, 1997.

Mahillon, "Subdivision of the *Escherichia coli* K-12 Genome for Sequencing: Manipulation and DNA Sequence of Transposable Elements Introducing Unique Restriction Sites" et al., *Gene*, 223: 47-54, 1998.

Martin, et al., *Acta Crystallogr. D. Biol. Crystallogr.*, 55: 386-398, 1999.

Mathys, et al., "Refinement and Structural Analysis of Barnase at 1.5 Å Resolution" *Gene*, 231: 1-13, 1999.

Matthews, et al., "Engineering and Interfacial Zinc Site to Increase Hormone-Receptor Affinity" *Chem. Biol.* 1:25-30, 1994.

Membrillo-Hernandez, et al., "Evolution of the *adhE* Gene Product of *Escherichia coli* from a Functional Reductase to a Dehydrogenase" *J. Biol. Chem.* 275: 33869-33875, 2000.

Metzger, et al., "Engineering the Mouse Genome by Site-Specific Recombination" *Curr. Opin. Biotechnol.* 10: 470-476, 1999.

McLaughlin, et al., "Effects of Functional Group Changes in the EcoRI Recognition Site on the Cleavage Reaction Catalyzed by the Endonuclease" *Biochemistry*, 26: 7238-7245, 1987.

McMillan, et al., "Allosteric Inhibitors of Inducible Nitric Oxide Synthase Dimerization Discovered via Combinatorial Chemistry" *Proc. Natl. Acad. Sci, USA*, 97: 1506-1511, 2000.

Minshull et al., "Protein Evolution by Molecular Breeding" *Curr. Opin. Chem. Biol.* 3: 284-290, 1999.

Monteilhet, et al., Purification and Characterization of the in vitro, Activity of I-Sce I, a Novel and Highly Specific Endonuclease Encoded by a Group I Intron *Nucleic Acids Res.* 18: 1407-1413, 1990.

Monteilhet, et al., "Purification and Characterization of the DNA Cleavage and Recognition Site of I-ScaI Mitochondrial Group I Intron Encoded Endonuclease Produced in *Escherichia coli*" *Nucleic Acids Res.* 28: 1245-1251, 2000.

Muir, et al., "Expressed Protein Ligation: A General Method for Protein Engineering" *Proc. Natl. Acad. Sci, USA*, 95: 6705-6710, 1998.

Nagy, "Cre-Recombinase: The Universal Reagent for Genome Tailoring" *Genesis*, 26: 99-109, 2000.

Patten, et al., "Applications of DNA Shuffling to Pharmaceuticals and Vaccines" *Curr. Opin Biotechnol.* 8:724-733, 1997.

Paulus, "Protein Splicing and Related Forms of Protein Autoprocessing" *Annu. Rev. BioChem*, 69: 447-496, 2000.

Pearce, et al., "Structural and Mutational Analysis of Affinity-Inert Contact Residues at the Growth Hormone-Receptor Interface" *Biochemistry*, 35: 10300-10307, 1996.

Pederson, et al., "A Method for Directed Evolution and Functional Cloning of Enzymes" *Proc. Natl. Acad. Sci. USA*, 95: 10523-10528, 1998.

Perler, et al., "Protein Splicing and Autoproteolysis Mechanisms" *Curr. Opin. Chem. Biol.* I: 292-299, 1997.

Perler et al., "Protein Splicing and its Applications" *Curr. Opin. Biotechnol.* 11: 377-383, 2000.

Perler, et al., "A Natural Example of Protein Trans-Splicing" *Trends BioChem. Sci*, 24: 209-211, 1999.

Perrin, et al., "Asymmetrical Recognition and Activity of the I-SceI Endonuclease on its Site and on Intron—Exon Junctions" *EMBO J.* 12: 2939-2947, 1993.

Petrounia, et al., "Designed Evolution of Enzymatic Properties" *Curr. Opin. Biotechnol.* 11: 325-330, 2000.

Poland, et al., "Structural Insights into the Protein Splicing Mechanisms of PI-SceI" *J. Biol. Chem.* 275: 16408-16413, 2000.

Rajewsky, et al., "Perspectives Series: Molecular Medicine in Genetically Engineered Animals" *J. Clin Invest*, 98: 600-603, 1996.

Ray, et al., "The Cre-LoxP System: A Versatile Tool for Targeting Genes in a Cell- and Stage-Specific Manner" *Cell Transplant*, 9: 805-815, 2000.

Reetz, et al., "Enantioselective Enzymes for Organic Synthesis Created by Directed Evolution" *Chemistry*, 6: 407-412, 2000.

Reidhaar-Olson, et al., "Random Mutagenesis of Protein Sequences Using Oligonucleotide Cassettes" *Methods Enzymol.* 208:564-586, 1991.

Reidhaar-Olson, et al, "Combinatorial Cassette Mutgenesis as a Probe of the Informational Content of Protein Sequences" *Science*, 241: 53-57, 1988.

Ryu, et al., "Recent Progress in Biomolecular Engineering" *Biotechnol. Prog.* 16: 2-16, 2000.

Sadowski, "The Flp Recombinase of the 2-µm Plasmid of *Saccharomyces cerevisiae*" *Prog. Nucleic Acid Res. Mol. Biol.* 51: 53-91, 1995.

Schimenti, et al., "Functional Genomics in the Mouse: Phenotype-Based Mutagenesis Screens" *Genome Res.* 8: 698-710, 1998.

Seligman et al., "Genetic Analysis of the *Chlamydomonas Reinhardtii* I-CreI Mobile Intron Homing System in *Escherichia coli*"*Genetics*, 147: 1653-1664, 1997.

Senecoff, et al., "DNA Recognition by the FLP Recombinase of the Yeast 2µ Plasmid A Mutational Analysis of the FLP Binding Site" *J. Mol. Biol.* 201: 405-421, 1988.

Severinov, et al., "Expressed Protein Ligation, A Novel Method for Studying Protein-Protein Interactions in Transcription" *J. Biol. Chem.* 273: 16205-16209, 1998.

Shao, et al., "Protein Splicing: Occurrence, Mechanisms and Related Phenomena" *Chem. Biol.* 4: 187-194, 1997.

Siegal, et al., "Application of Cre/LoxP in *Drosophila*" *Methods Mol. Bol.* 136: 487-495, 2000.

Streaker, et al., "Ligand-Linked Structural Changes in the *Escherichia coli* Biotin Repressor: The Significance of Surface Loops for Binding and Allostery" *J. Mol. Biol.* 292: 619-632, 1999.

Sutherland, "Evolutionary Optimisation of Enzymes" *Curr. Opin. Chem. Biol.*, 4: 263-269, 2000.

Szczepanek, et al., "Critical Base Substitutions that Affect the Splicing and/or Homing Activities of the Group I Intron bi2 of Yeast Mitochondria" *Mol. Gen. Genet.* 264: 137-144, 2000.

Theodosiou, et al., "Use of FLP/FRT System to Study *Drosophila* Development" *Methods*, 14: 355-365, 1998.

Thierry, et al., "Nested Chromosomal Fragmentation in Yeast Using the Meganuclease I-Sec I: A New Method for Physical Mapping of Eukaryotic Genomes" *Nucleic Acids Res.* 20: 5625-5631, 1992.

Tobin, et al., "Directed Evolution: The 'Rational' Basis for 'Irrational' Design" *Curr. Opin. Struct. Biol.* 10: 421-427, 2000.

Wells, "Structural and Functional Epitopes in the Growth Hormone Receptor Complex" *Biotechnology* (NY): 13: 647-651, 1995.

Wende, et al., "Binding, Bending and Cleavage of DNA Substrates by the Homing Endonuclease PI-SceI" *Nucleic Acids Res.* 24: 4123-4132, 1996.

Wolfe, et al., "DNA Recognition by $Cys_2$ $His_2$ Zinc Finger Proteins" *Annu. Rev. Biophys. Biomol Struct.* 29: 183-212, 2000.

Wood, et al al., "A Genetic System Yields Self- Cleaving Inteins for Bioseparations" *Nat. Biotechnol.* 17: 889-892, 1999.

Yano, et al., "Directed Evolution of an Aspartate Aminotransferase with New Substrate Specificities" *Proc. Natl. Acad. Sci. USA*, 95: 5511-5515, 1998.

Yoon, et al., "Cre/*lox*P-Mediated in Vivo Excision of Large Segments from Yeast Genome and Their Amplification Based on the 2 µm Plasmid-Derived System" *Gene*, 22: 67-76, 1998.

Yoon, et al., "Cre/*lox*P-Mediated Excision and Amplification of Large Segments of the *Escherichia coli* Genome" *Genet. Anal.* 14: 89-95, 1998.

Zhang, et al., "Directed Evolution of a Fucosidase from a Galactosidase by DNA Shuffling and Screening" *Proc. Natl. Acad. Sci. USA*, 94: 4504-4509, 1997.

* cited by examiner

Figure 4
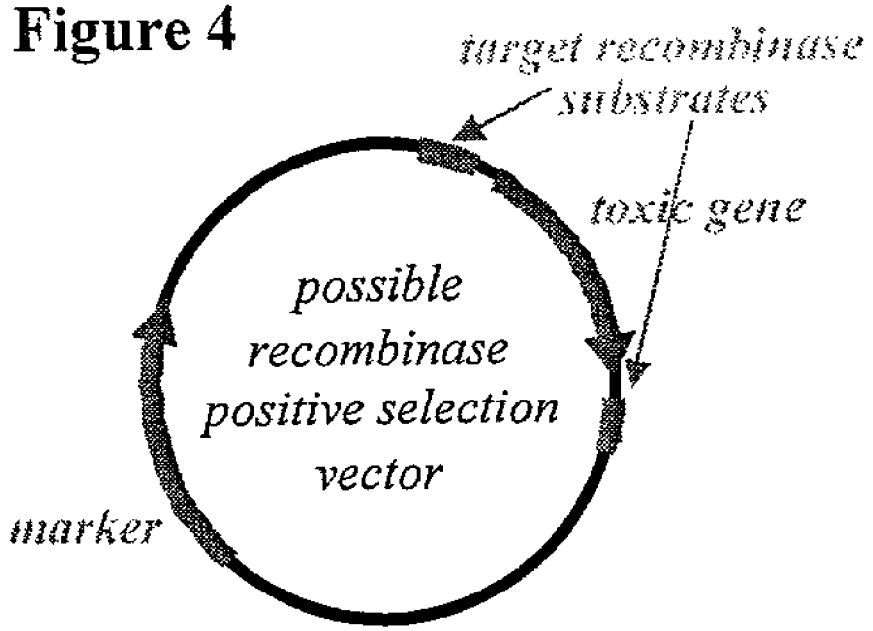
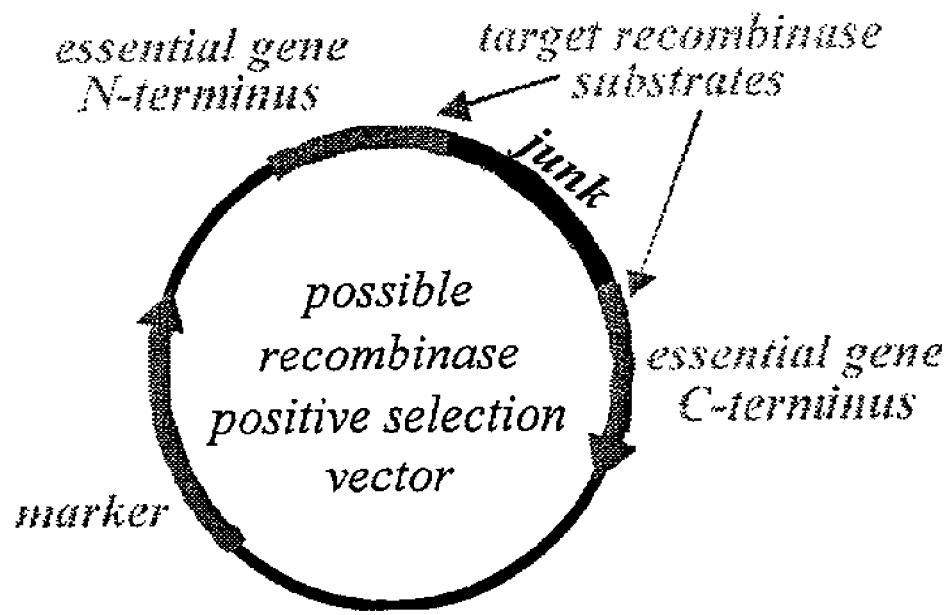

```
                                            11111111
                                   12345678901234567
FRT      5'-GAAGTTCCTATTCTCTAGAAAGTATAGGAACTTC-3'
         3'-CTTCAAGGATAAG AGATCTTT CATATCCTTGAAG-5'

FRTmut   5'-GAAGATTCTACTGTCTAGAAACAGTAGAATCTTC-3'
         3'-CTTCTAAGATGACAGATCTTTGTCATCTTAGAAG-5'
```

Figure 13

| | |
|---|---|
| I-SceI natural cleavage site | 5'-TAGGGATAACAGGGTAAT-3'<br>3'-ATCCCTATTGTCCCATTA-5' |
| target not cleaved<br>by wild-type I-SceI | 5'-TAGGGATAACA AGGTAAT-3'<br>3'-ATCCCTATTGT TCCATTA-5' |
| I-ScaI natural cleavage site | 5'-TGAGGTGCACTAGTTA-3'<br>3'-ACTCCACGTGATCAAT-5' |
| site in HIV-1 glycoprotein 120 | 5'-TGAGGTGCACTA TTAT-3'<br>3'-ACTCCACGTGAT TATA-5' |

Figure 21

*I-Sce*I natural cleavage site
```
5'-TAGGGATAACAGGGTAAT-3'
3'-ATCCCTATTGTCCCATTA-5'
``` target extended *I-Sce*I cleavage site for pSites+ vector
```
5'-TAGGGATAACAGGGTAAT G-3'
3'-ATCCCTATTGTCCCATTA C-5'
``` non-target extended *I-Sce*I cleavage sites for pSites– vector (can clone all three into one pSites–)
```
5'-TAGGGATAACAGGGTAAT A-3'
3'-ATCCCTATTGTCCCATTA T-5'

5'-TAGGGATAACAGGGTAAT T-3'
3'-ATCCCTATTGTCCCATTA A-5'

5'-TAGGGATAACAGGGTAAT C-3'
3'-ATCCCTATTGTCCCATTA G-5'
```

Figure 29

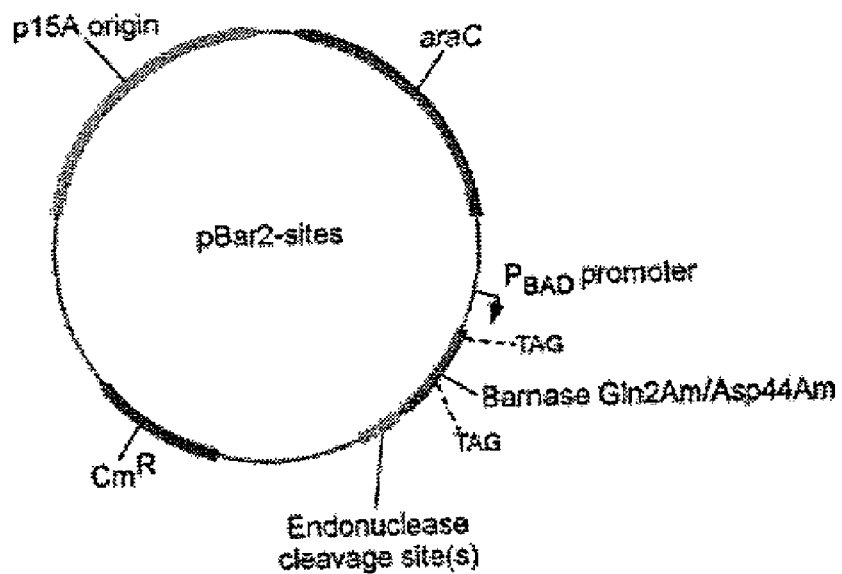
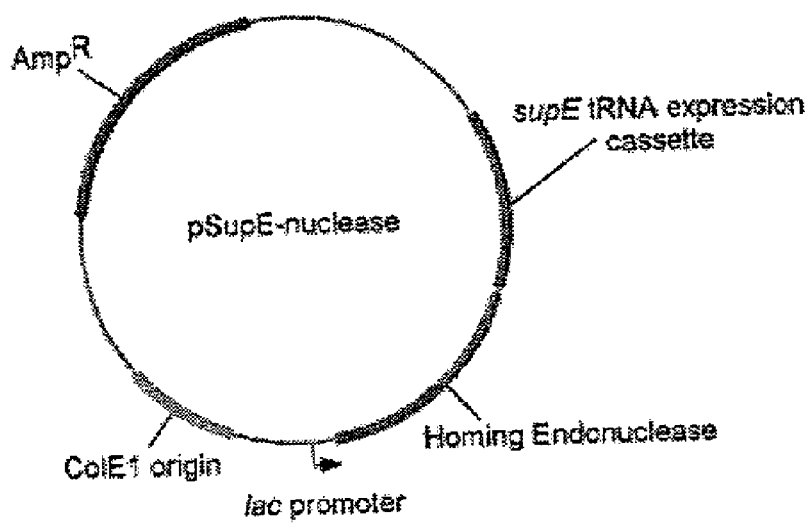
Figure 34

IN VIVO SELECTION SYSTEM FOR ENZYME ACTIVITY

PRIORITY INFORMATION

The present application claims priority under 35 U.S.C. § 119(e) to U.S. Provisional patent applications 60/277,094, filed Mar. 19, 2001, entitled "Approaches to Generating New Molecular Function"; 60/306,691, filed Jul. 20, 2001, entitled "Approaches to Generating New Molecular Function", and 60/353,565, filed Feb. 1, 2002, entitled "In Vivo Selection System for Homing Endonuclease Activity" and the entire contents of each of these applications are hereby incorporated by reference.

This invention was sponsored by NSF grant no. MCB-0094128 and the government has certain rights to the invention.

BACKGROUND OF THE INVENTION

Generating tailor-made enzymes to study biological processes and to catalyze useful new reactions remains one of the most exciting prospects of chemical biology. The rational design of enzymes with novel activities has generally proven to be difficult, Hedstrom, et al, *Science* 1992, 255, 1249-53, however, because our understanding of the interactions that govern protein function is not yet sufficiently sophisticated to predict reliably the effects of perturbing a protein's primary structure. Mimicking methods used by Nature to produce proteins with biologically essential activities, molecular evolution provides an alternate approach to generating enzymes with new functions. This approach involves iteratively (i) diversifying a protein of interest into a large library of mutant proteins, typically using whole genome mutagenesis, Schimenti, et al., *Genome Res.* 1998, 8, 698-710; Cupples, et al., *Proc. Natl. Acad. Sci. USA* 1989, 86, 5345-9; Hart, et al., *J. Am. Chem. Soc.* 1999, 121, 9887-9888, random cassette mutagenesis, Reidhaar-Olson, et al., *Methods Enzymol.* 1991, 208, 564-86; Reidhaar-Olson, et al., *Science* 1988, 241, 53-7, error-prone PCR, et al., *PCR Methods Applic.* 1992, 2, 28-33, or DNA shuffling, Stemmer, *Nature* 1994, 370, 389-91; Minshull, et al., *Curr. Opin. Chem. Biol* 1999, 3, 284-90; Harayama, *Trends Biotechnol.* 1998, 16, 76-82; Giver, et al., *Curr. Opin. Chem. Biol.* 1998, 2, 335-8; Patten, et al., *Curr. Opin. Biotechnol.* 1997, 8, 724-33, (ii) screening or selecting these variants for proteins with desired activities, and (iii) amplifying the genetic material (usually DNA) encoding the evolved proteins.

While a number of proteins have been evolved successfully using this strategy, the scope of protein molecular evolution is currently limited by the small number of methods to screen or select for proteins with desired properties. Among these methods, in vivo selections, in which cells expressing proteins with desired new functions propagate exponentially while cells expressing undesired library members fail to grow, offer several important advantages over in vitro selections and over both in vitro and in vivo screens. Because each molecule in an in vivo selection does not need to be individually separated and assayed, as is the case in screens, the potential diversity of proteins explored by in vivo selections is limited only by the transformation efficiency of *E. coli*. In vivo selections can therefore process protein libraries that are approximately 10, Hoseki, et al., *J. BioChem.* (Tokyo) 1999, 126, 951-6, members and thus 1,000- to 1,000,000-fold larger than protein libraries that are screened. Unlike selections performed in vitro, which typically select for binding or for a single bond-forming or bond-breaking event, Jäschke, et al., *Curr. Opin. Chem. Biol.* 2000, 4, 257-62; Famulok, et al., *Curr. Opin. Chem. Biol.* 1998, 2, 320-7; Pedersen, et al., *Proc. Natl. Acad. Sci. USA* 1998, 95, 10523-8, in vivo selections can choose proteins based on their ability to catalyze multiple-turnover reactions in the more relevant context of a living cell. Despite these considerable advantages, very few in vivo selections for proteins with desired properties exist. The vast majority of the in vivo selections described to date fall into one of two categories. Most link cell survival to a protein's function through complementation of an essential biosynthetic enzyme. Yano, et al., *Proc. Natl. Acad. Sci. USA* 1998, 95, 5511-5; Altamirano, et al., *Nature* 2000, 403, 617-22. The major limitation of this approach, however, is that proteins of interest can only be evolved to catalyze naturally occurring and metabolically critical reactions. The second major type of in vivo selection used for protein evolution selects for proteins that can transform substrates into the sole carbon source available to the cell. Membrillo-Hernandez, et al., *J. Biol. Chem.* 2000, 275, 33869-75; Bornscheuer, et al., *Bioorg Med. Chem.* 1999, 7, 2169-73. This selection is limited, however, to those enzymes that process cell permeable substrates into forms of carbon that can be processed by the cell.

In addition to suffering from a lack of more general in vivo selections prior strategies for the molecular evolution of proteins have been also limited by a lack of methods to select against undesired specificities or activities. As a result, evolved enzymes typically exhibit broadened, rather than truly altered, specificities or activities, Fong, et al., *Chem. Biol.* 2000, 7, 873-83; Iffland, et al., *Biochemistry* 2000, 39, 10790-8; Jurgens, et al., *Proc. Natl. Acad. Sci. USA* 2000, 97, 9925-30; Lanio, et al., *J. Mol. Biol.* 1998, 283, 59-69; Kumamaru, et al., *Nat. Biotechnol.* 1998, 16, 663-6; Zhang, et al., *Proc. Natl. Acad. Sci. USA* 1997, 94, 4504-9; Liu, et al., *Proc. Natl. Acad. Sci. USA* 1997, 94, 10092-10097; Yano, et al., *Proc. Natl. Acad. Sci. USA* 1998, 95, 5511-5, in contrast to the exquisite substrate specificities and precise activities that are characteristic of natural enzymes. Broadened specificities can emerge because the determinants allowing acceptance of a new substrate are often not mutually exclusive with those that allow acceptance of the wild-type substrate.

The lack of methods to select against undesired activities also prevents the evolution of a second important feature of many natural enzymes, the ability to be active under one set of conditions but inactive under slightly different conditions. Developing methods for the evolution of conditionally active proteins would enable researchers to address fundamental questions in protein function. For example, evolving a protein that is active in the presence of an exogenously added cell-permeable small molecule but inactive in the absence of this small molecule would allow for the first time the study of how an allosteric binding site can evolve in a library of closely related enzymes. The evolution of allostery would also reveal how frequently small molecule binding sites emerge during protein diversification.

Enzymes that manipulate the covalent structure of proteins and nucleic acids are of particular interest to chemists and biologists. These enzymes play important roles in biological processes ranging from the insertion of viral DNA into a host's genome to post-translational processing of essential enzymes. In addition, many of these enzymes catalyze intrinsically interesting and powerful chemical processes such as amide bond rearrangement or the cleavage and ligation of DNA with single-site per genome specificity. Finally, many enzymes that manipulate the structures of proteins and nucleic acids have proven to be extremely useful in a wide range of research applications including protein chemical synthesis, Chong, et al., *Gene* 1997, 192, 271-81; Blaschke, et al., *Methods Enzymol.* 2000, 328, 478-96; Evans, et al., *Biopolymers* 1999, 51, 333-42; Severinov, et al., *J. Biol. Chem.* 1998, 273, 16205-9; Muir, et al., *Proc. Natl. Acad. Sci. USA* 1998, 95, 6705-10, protein purification, Chong, et al., *Gene* 1997, 192, 271-81; Evans, et al., *J. Biol. Chem.* 1999, 274, 18359-63; Mathys, et al., *Gene* 1999, 231, 1-13, protein engineering, Ayers, et al., *Biopolymers* 1999, 51, 343-54; Holford, et al., *Structure* 1998, 6, 951-6, genome mapping, Thierry, et al., *Nucleic Acids Res.* 1992, 20, 5625-31; Belfort, et al., *Nucleic Acids Res.* 1997, 25, 3379-88; Copenhaver, et al., *Plant J.* 1996, 9, 259-72; Liu, et al., *Proc. Natl. Acad. Sci. USA* 1996, 93, 10303-8; Mahillon, et al., *Gene* 1997, 187, 273-9; Mahillon, et al., *Gene* 1998, 223, 47-54, screening protein libraries, Daugelat, et al., *Protein Sci.* 1999, 8, 644-53, and the creation of conditional genomic knock outs. Le, et al., *Methods Mol. Biol.* 2000, 136, 477-85; Rajewsky, et al., *J. Clin Invest* 1996, 98, 600-3; Yoon, et al., *Gene* 1998, 223, 67-76; Yoon, et al., *Genet. Anal* 1998, 14, 89-95. For these reasons, recombinases, homing endonucleases, and inteins have been the focus of intense research efforts over the past several years. Effective systems for generating and characterizing altered versions of these enzymes, however, have not been developed.

There remains a need for the development of improved systems for characterizing protein variants. There is a particular need for the development of systems that allow in vivo selection of protein activity. There is also a need for the development of systems that allow the characterization of altered biological cleavage proteins, and particular for the identification of cleavage enzymes with altered specificity.

SUMMARY OF THE INVENTION

The present invention provides systems for generating and characterizing protein derivatives in vivo. In particular, the invention provides systems that provide for in vivo expression and analysis of biological cleavage enzymes such as site-specific recombinases, homing endonucleases, or inteins. Preferably, the system is arranged so that activity of the relevant expressed protein is linked to a detectable, or more preferably, selectable readout, e.g., cell death.

The present invention therefore provides cells in which activity of an biological cleavage enzyme necessary for (or exclusive of) cell viability. In certain embodiments of the invention, the cell has been engineered so to allow positive selection for cleavage enzyme activity under one set of conditions, and negative selection under a different set of conditions.

The present invention also provides methods of generating cells in which activity of a biological cleavage enzyme is necessary for (or exclusive of) cell viability, as well as methods of using such cells. For instance, inventive cells may be used to identify and/or to characterize new biological cleavage enzymes having certain retained or newly acquired activities. The inventive cells are particularly useful for the identification of biological cleavage enzymes with altered specificity, and this information is useful in the evolution of novel enzymes having desired activites.

DEFINITIONS

Altered specificity, as that phrase is used herein, refers to a biological cleavage enzyme whose substrate specificity differs from that of the wild type enzyme. In particular, an altered specificity derivative of a biological cleavage enzyme preferably does not cleave, or cleaves to a substantially reduced extent, the substrate cleaved by the wild type enzyme. Thus, preferred altered specificity derivatives of a given biological cleavage enzyme do not merely have broadened specificity as compared with the wild type enzyme, but rather have different specificity.

The term antibody refers to an immunoglobulin, whether natural or wholly or partially synthetically produced. All derivatives thereof which maintain specific binding ability are also included in the term. The term also covers any protein having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, and IgE. Derivatives of the IgG class, however, are preferred in the present invention.

The term, associated with, is used to describe the interaction between or among two or more groups, moieties, compounds, monomers, etc. When two or more entities are "associated with" one another as described herein, they are linked by a direct or indirect covalent or non-covalent interaction. Preferably, the association is covalent. The covalent association may be through an amide, ester, carbon-carbon, disulfide, carbamate, ether, or carbonate linkage. The covalent association may also include a linker moiety such as a photocleavable linker. Desirable non-covalent interactions include hydrogen bonding, van der Waals interactions, hydrophobic interactions, magnetic interactions, electrostatic interactions, etc. Also, two or more entities or agents may be "associated" with one another by being present together in the same composition.

A biological cleavage enzyme, according to the present invention, is an enzyme that cleaves a biological macromolecule, preferably a nucleic acid or protein. Preferred biological cleavage enzymes recognize a particular sequence in a nucleic acid or protein as a cleavage signal. Particularly preferred biological cleavage enzymes include site-specific recombinases, homing endonucleases, and inteins. Those of ordinary skill in the art will appreciate, however, that a biological cleavage enzyme need not be a protein enzyme; various RNAs, or RNA-protein complexes, are known to have nucleic acid cleavage capabilities and may be considered to be biological cleavage enzymes in accordance with the present invention.

A biological macromolecule is a polynucleotide (e.g., RNA, DNA, RNA/DNA hybrid), protein, peptide, lipid, natural product, or polysaccharide. The biological macromolecule may be naturally occurring or non-naturally occurring. In a preferred embodiment, a biological macromolecule has a molecular weight greater than 500 g/mol.

Cell growth refers to the ability of the cell to carry out normal metabolic functions, but ultimately refers to the cell's ability to divide. Proteins that inhibit cell growth, e.g., toxic proteins, ultimately prevent the cell from dividing into two cells.

A derivative of a biological cleavage enzyme or gene is one that is highly related to, but not identical with, the biological cleavage enzyme or gene. For example, one aspect of the present invention is systems for identifying derivatives of existing biological cleavage enzymes, e.g., having altered specificity. In preferred embodiments of the invention derivative genes are generated by mutagenesis of a particular biological cleavage enzyme gene, and the encoded derivative enzymes are assayed as described herein. Those of ordinary skill in the art will appreciate that a derivative therefore will typically show very high sequence identity with the original enzyme from which it is derived. In many cases, only one or a few amino acid residues will be changed. In other cases, large stretches of amino acids will be identical, but certain specified regions will differ substantially. Those of ordinary skill in the art will recognize when a particular enzyme (or gene) is a derivative of another. In preferred embodiments of the invention, the relationship will be clear because the derivative gene will have been originally produced by mutagenesis or recombination of the original.

Inhibitory function refers to an activity in the cell that reduces or inhibits cell growth. There are two major types of inhibitory activity according to the present invention. The first type of inhibitory activity includes the addition of a toxic function to a cell. This includes introducing a plasmid encoding a toxic protein into a cell. Expression of the toxic protein in the cell slows or blocks the ability of the cell to grow and divide. Disrupting this inhibitory function involves identifying cells having reduced expression of the toxic protein. The second type of inhibitory function includes the disruption of an essential function in a cell. This includes in any way reducing or inhibiting the function of a protein essential for cell growth. Genes essential for cell growth include genes that encode proteins involved in cell metabolism, division, assimilation of nutrients, etc. Alternatively, such genes include proteins that promote growth of the cell in a particular (e.g., toxic) environment. For example, an antibiotic resistance gene may be disrupted leading to cell death in the presence of the corresponding antibiotic. Linked to, as that phrase is used herein, refers to a correlation between one event and another. For instance, activity of a biological cleavage enzyme is "linked to" cell viability when activity of the enzyme results in cell death (or cell survival) under the conditions of the experiment.

Polynucleotide, nucleic acid, or oligonucleotide refers to a polymer of nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, 0(6)-methylguanine, and 2-thiocytidine), chemically modified bases, biologically modified bases (e.g., methylated bases), intercalated bases, modified sugars (e.g., 2'-fluorori- bose, ribose, 2'-deoxyribose, arabinose, and hexose), or modified phosphate groups (e.g., phosphorothioates and 5'-N-phosphoramidite linkages).

A protein comprises a polymer of amino acid residues linked together by peptide bonds. The term, as used herein, refers to proteins, polypeptides, and peptide of any size, structure, or function. Typically, a protein will be at least three amino acids long. A protein may refer to an individual protein or a collection of proteins. A protein may refer to a full-length protein or a fragment of a protein. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive protein may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein may also be a single molecule or may be a multi-molecular complex. A protein may be just a fragment of a naturally occurring protein or peptide. A protein may be naturally occurring, recombinant, or synthetic, or any combination of these.

The term small molecule, as used herein, refers to a non-peptidic, non-oligomeric organic compound either synthesized in the laboratory or found in nature. Small molecules, as used herein, can refer to compounds that are "natural product-like", however, the term "small molecule" is not limited to "natural product-like" compounds. Rather, a small molecule is typically characterized in that it possesses one or more of the following characteristics including having several carbon-carbon bonds, having multiple stereocenters, having multiple functional groups, having at least two different types of functional groups, and having a molecular weight of less than 1500, although this characterization is not intended to be limiting for the purposes of the present invention.

The term small molecule scaffold, as used herein, refers to a chemical compound having at least one site for functionalization. In a preferred embodiment, the small molecule scaffold may have a multitude of sites for functionalization. These functionalization sites may be protected or masked as would be appreciated by one of skill in this art. The sites may also be found on an underlying ring structure or backbone.

Test enzyme refers to an enzyme of interest whose function is to be assessed by any of the assays of the invention. The test enzyme differs from the wild type enzyme by at least one amino acid residue (e.g., the test enzyme can have an insertion, deletion, or substitution of at least one residue). Alternatively, the test enzyme can differ from the wild type enzyme by the type of extent of post-translational processing (e.g., glycosylation). The test enzyme can be a particular mutant enzyme designed by the experimenter, or can be a plurality of multiple mutant enzymes generated by random mutagenesis.

The term toxic gene, as used herein, refers to a gene that either 1) produces a toxic product or 2) fails to produce an essential product. For instance, a gene that encodes a toxic enzyme (e.g., and enzyme that inhibits cell growth, usually by interfering with essential functions of the cell) is a toxic gene. Alternatively, a gene in which the coding sequence for an essential product (i.e., a product whose activity is necessary for cell survival under the conditions of the experiment) has been disrupted can be considered a "toxic gene".

DESCRIPTION OF THE FIGURES

FIG. 4 depicts a scheme for recombination that could be positively linked to cell survival either by (i) flanking a gene encoding a toxic protein by loxP sites, or (ii) disrupting an essential gene with an intervening segment of "junk DNA" flanked by loxP sites.

FIG. 13 depicts the creation of a mutant FRT (GAAGTTC-CTATTCTCTAGAAAGTATAGGAACTTC (SEQ ID NO: 17) and GAAGTTCCTATACTTTCTAGAGAATAG-GAACTTC (SEQ ID NO: 18)) target site (FRTmut) (GAA-GATTCTACTGTCTAGAAACAGTAGAATCTTC (SEQ ID NO: 23) and GAAGATTCTACTGTTTCTAGACAGTA-GAATCTTC (SEQ ID NO: 24)); in which all four critical bases implicated in the structural and biochemical characterization of the Flp-FRT complex were mutated.

FIG. 21 depicts exemplary substrate targets for the evolution of homing endonucleases with new DNA specificities (I-ScelI natural cleavage site (TAGGGATAACAGGGTAAT (SEQ ID NO: 1) and ATTACCCTGTTATCCCTA (SEQ ID NO: 19)); mutant target not cleaved by wild-type I-Scel (TAGGGATAACAAGGTAAT (SEQ ID NO: 2) and ATTAC-CTTGTTATCCCTA (SEQ ID NO: 25)): I-ScaI natural cleavage site (TGAGGTGCACTAGTTA (SEQ ID NO: 3) and TAACTAGTGCACCTCA (SEQ ID NO: 20)): site in HIV-1 glycoprotein 120 (TGAGGTGCACTATTAT (SEQ ID NO: 26) and ATATTAGTGCACCTCA (SEQ ID NO: 27)).

FIG. 29 depicts exemplary homing endonucleases with extended recognition specificity (I-Scel natural cleavage site (TAGGGATAACAGGGTAAT (SEQ ID NO: 1) and (AT-TACCCTGTTATCCCTA (SEQ ID NO: 19)): target extended I-Scel cleavage site for pSites+ vector (TAGGGATAA-CAGGGTAATG (SEQ ID NO 28) and CATTACCCTGT-TATCCCTA (SEQ ID NO: 29)): non-tarpet extented I-Scel cleavage sites for pSites− vector (can clone all three into one pSites−) (TAGGGATAACAGGGTAATA (SEQ ID NO: 30) and TATTACCCTGTTATCCCTA (SEQ ID NO: 31): TAGG-GATAACAGGGTAATT (SEQ ID NO 32) and AATTAC-CCTGTTATCCCTA (SEQ ID NO: 33): and TAGGGATAA-CAGGGTAATC (SEQ ID NO: 34) and GATTACCCTGTTATCCCTA (SEQ ID NO: 35)).

FIG. 34 depicts the selection system for homing endonuclease activity which is based on the two compatible plasmids pBar2-sites and pSup-E nuclease. The former plasmid contains nuclease cleavage sites of interest and places expression of an amber nonsense mutated barnase gene under control of an arabinose-induced and glucose-repressed PBAD promoter. The latter plasmid expresses the homing endonuclease enzyme together with an amber suppressor tRNA.

DESCRIPTION OF CERTAIN EMBODIMENTS OF THE INVENTION

Figure 1:
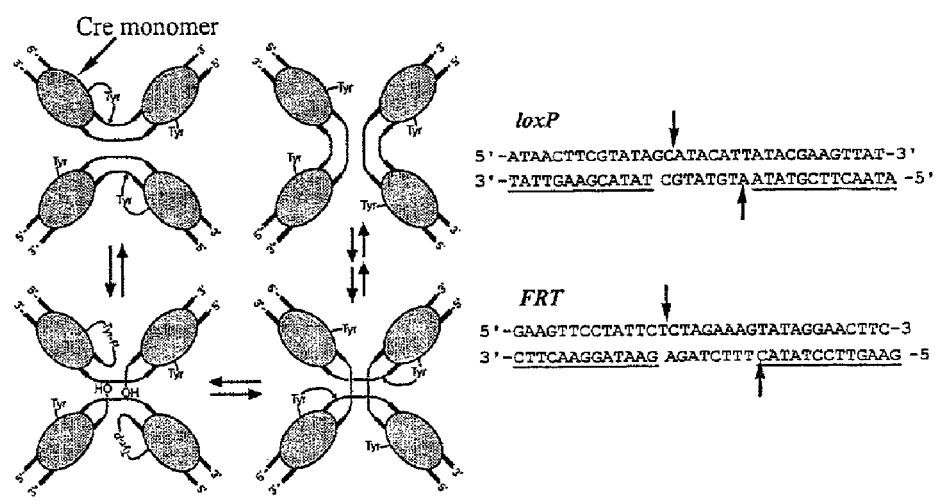
FIG. 1 depicts how Flp and Cre both catalyze the recombination of two 34 base pair DNA sequences designated FRT (GAAGTTCCTATTCTCTAGAAAGTATAGGAACTTC (SEQ ID NO: 17) and GAAGTTCCTATACTTTCTA- GAGAATAGGAACTTC (SEQ ID NO: 18)) and loxP (ATAACTTCGTATAGCATACATTATACGAAGTTAT (SEQ ID NO: 15) and ATAACTTCGTATAATGTATGC- TATACGAAGTTAT (SEQ ID NO: 16)) respectively, through a Holliday junction intermediate and require no accessory proteins or cofactors.
Figure 2:
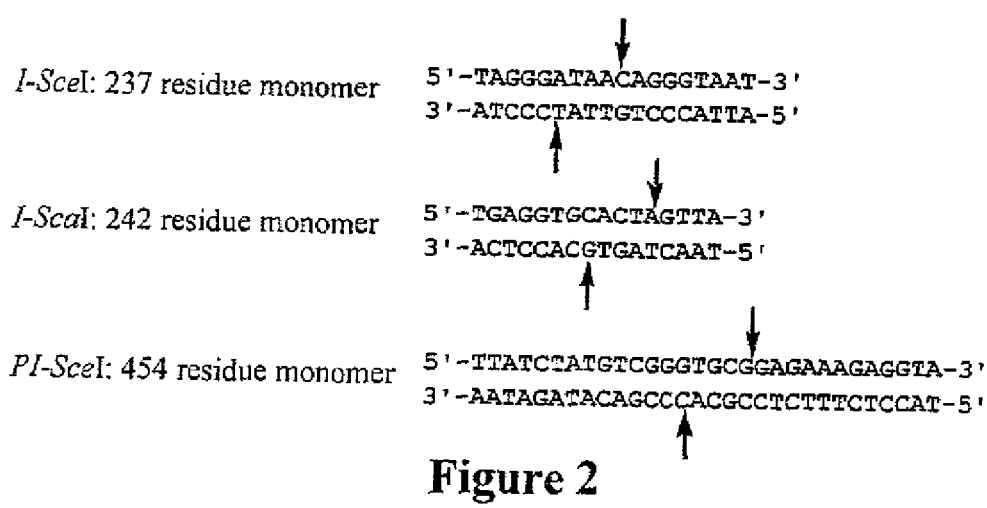
FIG. 2 depicts the cleavage specificities and physical characteristics of three members of the LAGLIDADG family (I-SceI (TAGGGATAACAGGGTAAT (SEQ ID NO: 1) and (ATTACCCTGTTATCCCTA (SEQ ID NO: 19)) PIScel and (TTATCTATGTCGGGTGCGGAGAAAGAGGTA (SEQ ID NO: 21) and TACCTCTTTCTCCGCACCCGACATA- GATAA (SEQ ID NO: 22)) and I-ScaI (TGAGGTGCAC- TAGTTA (SEQ ID NO: 3) and TAACTAGTGCACCTCA (SEQ ID NO: 20))).

As described above, the scope of protein molecular evolution would be greatly expanded by the development of new in vivo systems that link the activity of important classes of enzymes with detectable, or preferably selectable readouts. Recognizing this need, the present invention provides novel in vivo systems that allows either positive selection of cells that express a protein having a retained or acquired desired activity or negative selection against cells that express a protein having a retained or acquired undesired activity.

In general, the inventive system comprises a cell containing a toxic gene linked to a cleavage site and a cleaving enzyme whose activity is to be tested. For example, where the cleaving enzyme is a site-specific recombinase, the cleavage site comprises a nucleic acid sequence potentially recognized by the recombinase. In some embodiments, the toxic gene contains either an internal recombinase site or flanking recombinase sites, such that activity of the recombinase disrupts or removes the toxic gene; in yet other embodiments, the toxic gene comprises a disrupted essential gene (i.e., a gene whose activity is required for cell viability but whose product is not made unless an intervening sequence, flanked by recombination sites, is removed), so that activity of the recombinase is necessary for cell viability. Where the cleaving enzyme is a homing endonuclease, the cleavage site comprises a potential recognition site for the endnuclease so that the toxic gene is degraded when endonuclease activity is present. Where the cleaving enzyme is an intein, the cleavage site comprises sequences within the toxic gene that render the polypeptide encoded by the gene susceptible to cleavage by the relevant intein or derivative. In some embodiments, the cleavage site is arranged so that activity of the intein removes a disrupting sequence from an essential protein; in other embodiments, the cleavage site is arranged so that activity of the intein destroys the toxic product, resulting in cell viability.

In certain preferred embodiments of the invention, activity of the toxic gene (or its encoded product) is "caged" so that cells are not killed before the cleaving enzyme has had an opportunity to act. For example, the particular toxic gene may be under the control of a regulatable promoter. Alternatively or additionally, the particular toxic gene employed may encode a conditionally-sensitive (e.g., temperature sensitive) version of a toxic gene product, or the gene may include one or more nonsense mutations suppressable by appropriate nonsense suppressors.

In some preferred embodiments of the present invention, the inventive selection system can apply both positive and negative screening or selection pressure to the activity of the relevant biological cleavage enzyme. The present invention encompasses the recognition that application of both positive and negative screens in vivo has important advantages over other available strategies for evolving new protein functions. For example, it is well appreciated that our understanding of macromolecular function is not sophisticated enough to predict all of the key residues in a protein that are responsible for a particular aspect of substrate recognition or catalysis. Available techniques such as site-directed mutagenesis, however, are often guided by assumptions about the residues important to an enzyme's function even though researchers have repeatedly found that residues not immediately contacting any substrate moiety can play profound roles in the specificity or catalytic ability of an enzyme. Tobin, et al., *Curr. Opin. Struct. Biol.* 2000, 10, 421-7; Petrounia, et al., *Curr. Opin. Biotechnol.* 2000, 11, 325-30; Sutherland, *Curr. Opin. Chem. Biol.* 2000, 4, 263-9; Reetz. et al., *Chemistry* 2000, 6, 407-12; Ryu, et al., *Biotechnol. Prog.* 2000, 16, 2-16; Minshull, et al., *Curr. Opin. Chem. Biol.* 1999, 3, 284-90; Kuchner, et al., *Trends Biotechnol.* 1997, 15, 523-30.

Unlike traditional mutagenesis approaches, the inventive use of positive and negative in vivo selections can identify both critical and non-essential residues in an unbiased manner. In addition, the inventive use of in vivo selections ensures that the enzymes are being studied in a biologically relevant context, whereas the common approach of purifying and assaying in vitro site-directed mutants can overlook residues that are important to function in the living cell but are less important when taken out of context. Finally, the inventive "molecular evolution" strategies offer researchers a greater likelihood of achieving a gain of function rather than a loss of function when changing an enzyme's composition, compared with the difficulty of rationally engineering proteins toward increased function. The interpretation of positive results often provides deeper insights into the functional requirements of an enzyme than the interpretation of negative results since a loss of function can be accounted for by many hypotheses unrelated to the molecular interactions of interest. It will be appreciated that inventive molecular evolution approaches are often desirably used in combination with site-directed mutagenesis strategies, in order, for example, to simplify deconvolution of the volumes of data that can be generated. The results provided by inventive molecular evolution studies may be much more complex than the typical data emerging from traditional mutagenesis studies, but this complexity is an accurate and revealing reflection of the many factors that contribute to changes in protein function.

Thus, in certain preferred embodiments of the invention, a system is provided in which activity of a given biological cleavage enzyme is monitored with respect to both a desired cleavage site and an undesired cleavage site. For example, a single cell may be provided that contains 1) a biological cleavage enzyme; 2) a toxic marker (gene or protein) linked to a desired cleavage site; and 3) a detectable marker (gene or protein) linked to an undesirable cleavage site. Alternatively, two cells may be provided for comparison analysis, one of which expresses 1) the biological cleavage enzyme; and 2) a toxic marker, and the second of which comprises 1) the biological cleavage enzyme; and 2) the detectable marker. The detectable marker may be any gene or protein that can be detected, directly or indirectly, so that cleavage at the undesirable cleavage site may be monitored. Those of ordinary skill in the art will be well aware of a wide range of reporter genes or other markers that could be desirably employed. In certain preferred embodiments of the invention, the detectable marker is a selectable marker, so that undesirable cleavage may be detected by selection. To give but one example, the detectable marker may comprise an antibiotic resistance gene, so that undesirable cleavage will result in cell death on appropriate media. In some preferred embodiments of the invention, the detectable marker comprises the biological cleavage enzyme itself, so that the enzyme is not made (or is destroyed) if undesirable cleavage occurs.

The invention also provides methods of generating cells engineered to allow selection for activity of a cleavage enzyme as described herein, as well as methods of using such cells, for example, to identify new cleavage enzyme derivatives with altered cleavage specificity, etc.

Those of ordinary skill in the art will appreciate that the Examples presented below describe bacterial cells (in particular E. coli cells) engineered to allow in vivo selection for biological cleavage enzyme activity, but that the invention is not limited to the use of such cells. Any cell type in which the relevant biological cleavage enzyme is active may be utilized in accordance with the present invention. Cells that may be utilized in the present invention include, but are not limited to prokaryotic or eukaryotic cells, including bacteria, protozoa, fungi (e.g., Neurospora), yeast, and mammalian cells, to name a few.

Those of ordinary skill in the art will further appreciate that the teachings of the present invention are not limited in their application to biological cleavage enzymes. Rather, the teachings of the present invention may be applied, with no more than routine experimentation, to the generation of cells in which expression of a particular gene is correlated with cell viability. In particular, the invention encompasses any cell that has been engineered to allow both positive and negative selection for activity of a given gene product. Application of the inventive ideas and concepts to recombinases, homing endonucleases, and inteins represent merely preferred emodiments of the present invention.

Recombinases

Among the site-specific recombinase enzymes, the Flp recombinase, Jayaram, *Science* 1997, 276, 49-51; Sadowski, *Prog Nucleic Acid Res. Mol. Biol.* 1995, 51, 53-91, from the yeast 2 micron plasmid and the Cre recombinase, Le, et al., *Methods Mol. Biol.* 2000, 136, 477-85; Gorman, et al., *Curr. Opin. Biotechnol.* 2000, 11, 455-60; Nagy, *Genesis* 2000, 26, 99-109; Gopaul, et al., *Curr. Opin. Struct. Biol.* 1999, 9, 14-20, from bacteriophage P1 are the best studied examples. Flp and Cre both catalyze the recombination of two 34 base pair DNA sequences designated FRT and loxP, respectively, through a Holliday junction intermediate and require no accessory proteins or cofactors (FIG. 1, Guo, et al., *Nature* 1997, 389, 40-6). FRT and loxP consist of two 13 or 14 base pair inverted repeats ("half sites") flanking an asymmetric eight or six base pair core sequence, respectively (FIG. 1). In both enzymes, a catalytic Tyr initiates the recombination reaction by nucleophilically attacking a DNA phosphodiester. The regiospecificity of this attack by Tyr differs between Cre and Flp. The catalytic Tyr that cleaves a given half site in Cre comes from the same recombinase molecule that binds that half site (cis cleavage, Guo, et al., *Nature* 1997, 389, 40-6, depicted in FIG. 1), while the attacking Tyr comes from a different monomer in Flp (trans cleavage, Chen, et al., *Mol. Cell.* 2000, 6, 885-97). Although mutations in the core sequences in general are tolerated by Cre and FRT, mutations of the bases in the inverted repeats lead to large decreases in recombination efficiency by both wild-type enzymes. Lee, et al., *Gene* 1998, 216, 55-65; Senecoff, et al., *J. Mol. Biol.* 1988, 201, 405-21. The high-resolution X-ray crystal structures of both enzymes have been solved as complexes with their DNA substrates, Gopaul, et al., *Curr. Opin. Struct. Biol.* 1999, 9, 14-20; Guo, et al., *Nature* 1997, 389, 40-6; Chen, et al., *Mol. Cell.* 2000, 6, 885-97; Guo, et al., *Proc. Natl. Acad. Sci. USA* 1999, 96, 7143-8; Gopaul, et al., *EMBO J.* 1998, 17, 4175-87, and reveal a pseudo-$C_4$ symmetric tetramer in which each recombinase monomer is bound to one DNA half site. While a few residues in both enzymes make hydrogen bonds with bases in the substrate, the basis for the DNA specificity of site-specific recombinases is not well understood, and no successful efforts to engineer these enzymes to recombine altered DNA sequences have been reported to date.

Because Flp and Cre are active when heterologously expressed in a variety of organisms, Le, et al., *Methods Mol. Biol.* 2000, 136, 477-85; Gorman, et al., *Curr. Opin. Biotechnol.* 2000, 11, 455-60; Fiering, et al., *Methods Enzymol.* 1999, 306, 42-66; Theodosiou, et al., *Methods* 1998, 14, 355-65; Ray, et al., *Cell Transplant.* 2000, 9, 805-15; Siegal, et al., *Methods Mol. Biol.* 2000, 136, 487-95; Metzger, et al., *Curr. Opin. Biotechnol.* 1999, 10, 470-6; Lyznik, et al., *Plant J.* 1995, 8, 177-86; Lyznik, et al., *Nucleic Acids Res.* 1996, 24, 3784-9, including *E. coli*, yeast, plants, *Drosophila*, and mammals, these enzymes have proven to be very useful in the manipulation of genomic DNA. Site-specific recombinases have been used, for example, to generate conditional transgenic and "knockout" mice in which recombinase expression (under control of an inducible or tissue-specific promoter) leads to the permanent insertion or excision of genomic DNA flanked by loxP or FRT sequences. Gorman, et al., *Curr. Opin. Biotechnol.* 2000, 11, 455-60. Manipulating genomes using Flp or Cre, however, requires cell lines in which FRT or loxP sites have been incorporated into the genomic DNA since these sites do not exist in most genomes.

As described in further detail in the Examples below, we have prepared cells containing either 1) a recombinase, and 2) an essential gene whose coding sequence is interrupted by intervening DNA flanked by recombination sites; or 1) a recombinase, and 2) a toxic gene flanked by recombination sites. Furthermore, we used this system to screen for recombinase derivatives having altered specificity.

Homing Endonucleases

Homing endonucleases are a recently characterized class of sequence-specific double stranded DNA cleaving enzymes that are involved in the process of inserting mobile genetic elements into genomic DNA. Unlike restriction endonucleases, which typically operate on palindromic DNA sequences 4-8 base pairs in length, homing endonucleases recognize very long and frequently non-palindromic sequences—12-40 base pairs in length (see, for example, Chevalier et al. *Nucleic Acids Res.* 2001, 29, 3757-3774; Jurica et al. *Cell. Mol. Life. Sci.* 1999, 55, 1304-1326; Belfort et al. *Nucleic Acids Res.* 1997, 25, 3379-3388). Despite the unusual sequence specificity of homing endonucleases and their resulting utility as highly specific DNA cleavage agents, our understanding of these enzymes remains relatively limited. The few X-ray crystal or NMR solution structures of homing endonucleases solved thus far reveal a diverse set of base-specific hydrogen bonds, polar interactions and van der Waals contacts between protein and DNA, all of which may contribute to the specificity of these enzymes.

Mechanistic studies of DNA cleavage by homing endonucleases have primarily adopted one of two strategies. The substrate DNA sequence can be mutated and assayed in vitro to identify the bases required for substrate cleavage by the wild type enzyme, or the homing endonuclease can be subjected to site-directed mutagenesis and the resulting mutant enzymes assayed to identify catalytically important residues. Both attempts require the cloning, expression and purification of one of more endonucleases, the synthesis of one or more DNA substrates and the analysis of in vitro cleavage reactions. Further complicating the in vitro characterization of these enzymes, the overexpression of some homing endonucleases in common expression systems has been reported to induce cell lysis (see, for example, Jurica et al. *Cell. Mol. Life. Sci.* 1999, 55, 1304-1326), limiting the yields of active protein.

Since the availability of purified homing endonucleases and their mutants is a significant bottleneck for the rapid characterization of this class of proteins, it would be desirable to develop a general activity assay for homing endonucleases that does not require overexpression and purification of the protein of interest. While several approaches have been reported that link DNA cleavage to an observable signal in vitro (see, for example, Li et al. *Nucleic Acids Res.* 2000, 28, e52; McLaughlin et al. *Biochemistry* 1987, 26, 7238-7245; Waters et al. *Anal Biochem.* 1992, 213, 234-240; Lee et al. *Methods Enzymol.* 1997, 278, 343-363), very few general strategies exist to assay enzyme-catalyzed sequence-specific DNA cleavage in living cells (see, for example, Seligman et al. *Genetics,* 1997, 147, 1653-1664).

As described in further detail in the Examples below, cells containing 1) a homing endonuclease, and 2) a caged toxic gene linked to an endonuclease cleavage site have been prepared. In particular, cells have been generated that carry the highly toxic barnase gene under control of a repressable promoter. The particular promoter that we employed was the $P_{BAD}$ promoter, but those of ordinary skill in the art will readily appreciate that any of a variety of other inducible promoters or regulatory elements could alternatively have been used. In general, any promoter or regulatory element that functions in the relevant cells and that responds to a controllable signal could be employed in the practice of the present invention. Furthermore, we utilized a version of the barnase gene that included a nonsense mutation that was suppressed by a suppressor tRNA also present in the cell. We are using this system to screen for endonuclease derivatives having altered specificity.

Additionally, a system comprising 1) a homing endonuclease gene linked to an undesirable homing endonuclease cleavage site; and 2) a toxic gene linked to a desired homing endonuclease cleavage site has also been generated. This system allows positive and negative selection pressure to be applied simultaneously in the identification of homing endonucleases (or derivatives) having a desired site specificity. It has been particularly been found that increasing or decreasing the number of copies of undesired cleavage sites in the vector can modulate the stringency of this negative selection. For example, for the I-SceI, PI-Sce-I, I-ScaI and proteins, the wild-type cleavage sites of I-SceI, PI-SceI, or I-ScaI can be used as the "undesired" cleavage sites, and the corresponding wild-type nuclease can be expressed from the appropriate plasmid. Cells are not likely to survive under these conditions. As controls, the expression of the inactive catalytic mutants should allow cells to survive in this negative selection. Similarly, the combination of wild-type endonucleases and mutant sites known not to be cleaved by the wild-type enzymes, such as those described herein should also be viable. The phenotypic characterization of partially active mutants and cleavage substrates in these negative selections provide a robust system for removing homing endonuclease with desired cleavage specificities from the evolving pool of enzymes.

Protein Splicing Enzymes

Figure 3:
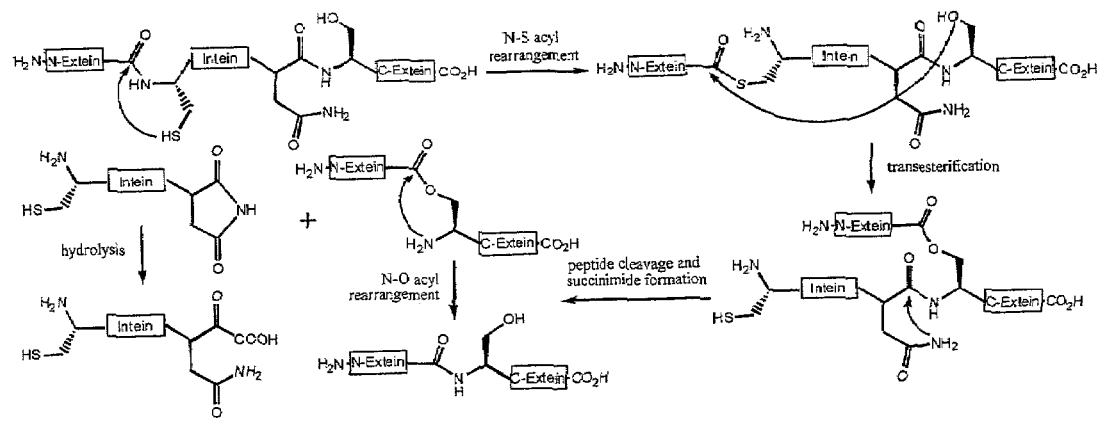
FIG. 3 depicts the currently accepted method of protein splicing.

Like recombinases and homing endonucleases, inteins are also proteins that catalyze changes in the covalent structure of macromolecules. Inteins promote the postranslational excision of an intervening protein sequence (the intein) and the ligation of the surrounding polypeptides (the "exteins"). Paulus, *Annu. Rev. BioChem.* 2000, 69, 447-96; Gimble, *Chem. Biol.* 1998, 5, R251-6; Perler, et al., *Curr. Opin. Chem. Biol.* 1997, 1, 292-9; Shao, et al., *Chem. Biol.* 1997, 4, 187-94; Liu, *Annu. Rev. Genet.* 2000, 34, 61-76; Perler, et al., *Curr. Opin. Biotechnol.* 2000, 11, 377-83. This process, known as protein splicing, is analogous to the excision of introns and ligation of exons during RNA splicing. Natural inteins are found in a wide variety of exteins unrelated in sequence, structure, or function. Liu, *Annu. Rev. Genet.* 2000, 34, 61-76; Perler, et al., *Curr. Opin. Biotechnol.* 2000, 11, 377-83. In addition to the canonical N-extein-intein-C-extein arrangement, some natural inteins such as the DnaE intein from cyanobacterium *Synechocytis* sp. strain PCC6803 are known to exist as two separate polypeptide chains (N-extein-N-intein and C-intein-C-extein) that form a complex and induce protein splicing in trans. Perler, *Trends BioChem. Sci.* 1999, 24, 209-11. The currently accepted mechanism of protein splicing (FIG. 3) begins with an N—O (or N—S) acyl rearrangement at the N-terminal splice junction to afford a linear ester or thioester intermediate. The Ser or Cys nucleophile at the C-terminal splice junction then attacks this ester to yield a branched polypeptide intermediate. The carboxamide side chain of the conserved terminal Asn in the intein then attacks polypeptide backbone to yield a succinimide and a linear ester. Hydrolysis of the succinimide provides the excised intein, while O—N (or S—N) acyl rearrangement of the linear ester affords the ligated extein. Paulus, *Annu. Rev. BioChem.* 2000, 69, 447-96; Perler, *Curr. Opin. Biotechnol.* 2000, 11, 377-83. Canonical inteins very likely undergo significant conformational changes during protein splicing. The crystal structure of the *S.* cerevisiae VMA intein precursor, Poland, et al., *J. Biol. Chem.* 2000, 275, 16408-13, indicates that the C-terminal Cys residue is positioned too far away to attack directly either a peptide or ester bond at the N-terminal splice junction, suggesting that a conformational shift must take place before formation of the branched intermediate can take place.

The conformational rearrangements that are thought to be required for intein-catalyzed protein splicing make inteins an ideal system for examining how conformational changes in one part of a protein can be transmitted to enable or disable substrate processing in the active site. In addition to rearrangements that naturally occur during an enzyme-catalyzed reaction, the binding of a small organic molecule to an allosteric site in a enzyme is a second common mechanism of inducing conformational change in proteins. Recent studies suggest that the vast majority of proteins have regions of low structural stability linked to their active sites; Luque, et al., *Proteins* 2000, Suppl. 4, 63-71, these regions of low structural ability have been experimentally, Streaker, et al., *J. Mol. Biol.* 1999, 292, 619-32, and computationally, Freire, *Proc. Natl. Acad. Sci. USA* 1999, 96, 10118-22, identified as transmitting information between distal sites in natural allosteric proteins. Proteins not naturally regulated by allostery may therefore have the potential to acquire allosteric regulation if small molecule binding sites can be introduced in the proper context. In support of this hypothesis, two examples have been reported recently in which small molecules identified from screening combinatorial libraries were found to induce allosteric changes in naturally, non-allosteric proteins. DeDecker, *Chem. Biol.* 2000, 7, R103-7; Foster, et al., *Science* 1999, 286, 2507-10; McMillan, et al., *Proc. Natl. Acad. Sci. USA* 2000, 97, 1506-11. Attempts to rationally design new small molecule binding sites into proteins, however, have met with little success despite the obvious importance of non-active site ligand binding to the pharmaceutical industry. Krantz, *Nat. Biotechnol.* 1998, 16, 1294. Promisingly, small molecules that can restore a defective protein-protein interface created by mutating a Trp residue in the human growth hormone receptor to Ala were recently found by screening. Guo, et al., *Science* 2000, 288, 2042-5. Most enzymes, however, lack protein-protein interfaces that are required for their function and that are characterized to the degree, Wells, *Biotechnology (NY)* 1995, 13, 647-51; Clackson, et al., *J. Mol. Biol.* 1998, 277, 1111-28; Matthews, et al., *Chem. Biol.* 1994, 1, 25-30; Atwell, et al., *Science* 1997, 278, 1125-8; Pearce, et al., *Biochemistry* 1996, 35, 10300-7, of the human growth hormone receptor.

As a general approach to generating artificial allosteric proteins, in vivo selections to evolve inteins that can be activated or inactivated by the binding of a synthetic small molecule can be utilized. Characterizing inteins evolved in this manner may reveal the requirements for creating an allosteric small molecule binding site in an enzyme, and would demonstrate how protein allostery can be evolved over several generations of diversification and selection. In addition, these studies may identify the structurally plastic "hot spots" conducive to small molecule binding on or near the intein surface. The identification of sites on a protein receptive to small molecule binding is a longstanding challenge with important implications for medicinal chemistry. Krantz, *Nat. Biotechnol.* 1998, 16, 1294. Such an effort, if performed in the relevant context of the living cell, would require developing new methods to link cell survival both positively and negatively with protein splicing.

As described herein, cells containing 1) an essential protein disrupted by an intein and 2) a protein splicing enzyme that removes the intein are provided. It will be appreciated that in most embodiments, the intein and the protein splicing enzyme are one and the same. However, in certain embodiments, (e.g., where intein removal is catalyzed in trans, intein removal may be catalyzed by a separate entity. The use of these cells has been further described to identify new inteins or intein derivatives that are conditionally active. In particular, assays are described that allow positive selection for intein activity in the presence (or absence) of a ligand or other regulator, preferably a small molecule, and negative selection against intein activity in the absence (or presence) of the ligand or regulator. Additionally methods and strategies are described for preparing, identifying, and characterizing ligands and/or regultors of allosteric inteins.

Kits

The present invention also provides kits for use in the inventive methods. The kits may contain any item or composition useful in practicing the present invention. For example, kits may include the inventive cells engineered to allow selection for or against activity of a biological cleavage enzyme. The kits may further include control cells, and/or reagents useful for control reactions with experimental cells. Those of ordinary skill in the art will appreciate that inventive kits may include cells that contain all of the features described herein other than a biological cleavage enzyme. Users of the kit may then introduce desired enzymes into the cells in order to characterize or otherwise study activity of the introduced enzymes.

To give but one non-limiting example of a kit provided by the present invention, cells containing 1) a toxic gene linked to a desirable cleavage site; and 2) a detectable gene linked to an undesirable cleavage site may be provided, optionally in combination with reagents useful for selection against the toxic gene and/or detection of the detectable gene. As another non-limiting example, cells containing an essential gene interrupted by an intein may be provided in combination with one or more potential conditional ligands or regulators.

In other embodiments of inventive kits, the present invention provides arrays (e.g., nucleic acid or polypeptide arrays) suitable for evaluating the specificity of biological cleavage enzymes as described herein.

Altered Specificity Enzymes and Uses Therefor

As discussed herein, the present invention provides systems for generating, identifying, and characterizing biological cleavage enzymes having altered specificity. Those of ordinary skill in the art will readily appreciate that such altered specificity enzymes have significant utility in any of a variety of applications. Altered specificity cleavage enzymes as described herein may be selected to have specificity for a biological target whose function or activity is under investigation. The altered specificity enzyme could be used to disrupt or inactivate the biological target in vivo, thereby generating a mutant cell whose characteristics will reveal insights into the function or activity of the cleaved target.

Alternatively or additionally, inventive altered specificity enzymes can usefully be employed as therapeutic agents if they are designed and/or selected to cleave targets with undesirable therapeutic characteristics. For instance, altered specificity enzymes can be identified and produced that have specificity for one or more genes or proteins found in an infectious agent such as a microbe or virus, or for an undesirable endogenous target such as a tumor-promoting agent.

The present invention therefore provides useful research agents and useful therapeutic agents, as well as methods of identifying, making, and using such agents.

EQUIVALENTS

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

EXEMPLIFICATION

Example 1

An in vivo Selection System for Homing Endonuclease Activity

As discussed above, the present invention provides a novel in vivo system for selective cells having a homing endonuclease activity.

Development of a Conditionally Toxic Homing Endonuclease Substrate: Non-native DNA cleavage is typically detrimental to living cells. In order to transform DNA cleavage into an event necessary for cell survival, the ability of homing endonucleases to transform circular plasmid DNA into linear products was utilized. Since linear DNA does not replicate efficiently in *E. coli* and is rapidly degraded by the endogenous RecBCD nuclease (Kuzminov et al. *J Bacteriol* 1997, 179, 880-888), it was hypothesized that endonuclease-catalyzed cleavage of a plasmid encoding a toxic protein could rescue the ability of cells to survive under suitably controlled growth conditions.

The first requirement of implementing this strategy is "caging" the toxicity of a toxic gene so that it will not kill cells before a homing endonuclease that may be active within the cells has had an opportunity to catalyze the toxic plasmid's cleavage. To effect this caging, a mutant form of barnase, the highly toxic RNase from *Bacillus amyloliquefaciens* (Axe et al. *Proc. Natl. Acad. Sci. USA* 1996, 93, 5590-5594; Martin et al *Acta Crystallogr. D. Biol. Crystallogr.* 1999, 55, 386-398; Jucovic et al. *Protein Eng* 1995, 8, 497-499; Hartley et al. *Trends Biochem. Sci.* 1989, 14, 450-454; Hartley et al. *J. Mol. Biol.* 1988, 202, 913-915) was utilized, in which two non-essential residues (Gln2 and Asp44) had been mutated to amber (TAG) stop codons (Liu et al. *Proc. Natl. Acad. Sci. USA* 1999, 96, 4780-4785). The amber-mutated barnase gene (Bar2) was placed under the control of the pBAD promoter (Guzman et al. *J. Bacteriol.* 1995, 177, 4121-4130), allowing barnase expression to be induced with arabinose and repressed with glucose. Efforts to cage the toxicity of wild-type barnase simply by repressing its expression using glucose were unsuccessful, suggesting that the low level of barnase expression even under pBAD repression conditions is lethal to *E. coli*. Plasmids containing Bar2 were introduced into *E. coli* strain DH10B, which has minimal ability to suppress amber nonsense codons. The resulting cells were viable in the presence of glucose as well as in the presence of arabinose, indicating that the caging strategy successfully abrogates the toxicity of barnase (see FIG. 35A).

Figure 35:
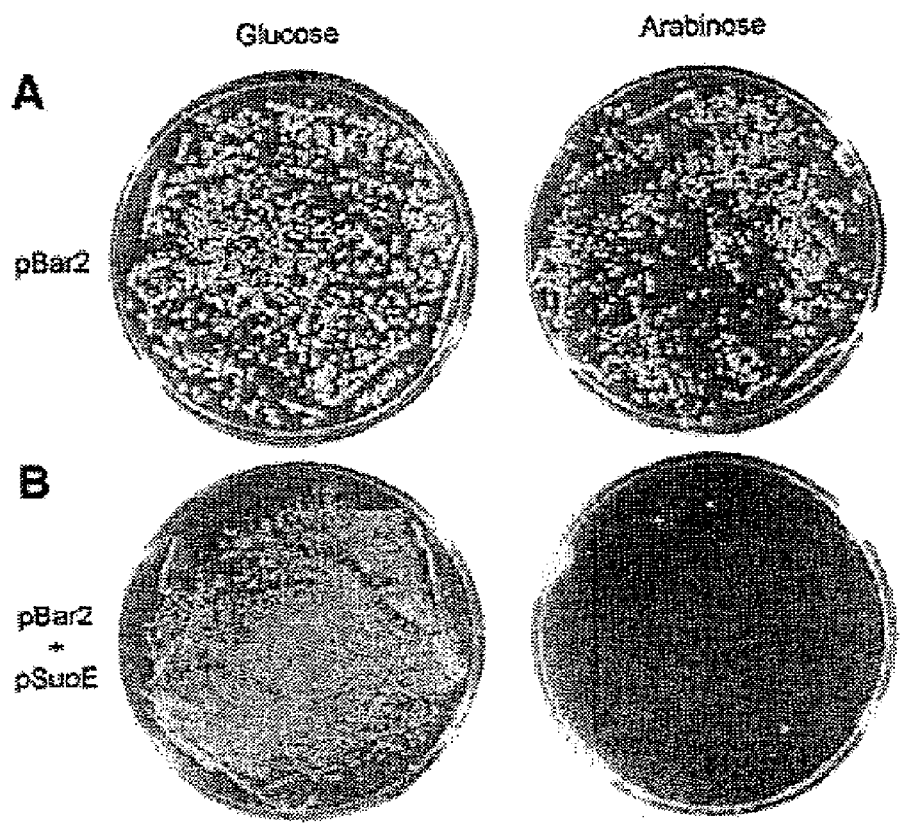
FIG. 35 depicts (A) Cells harboring the pBar2 plasmid that show similar viability on glucose and arabinose, indicating that the toxicity of barnase has been successfully caged by the two amber codons. Identical numbers of transformants were plated on arabinose and glucose plates. (B) Transforming pSupE into cells harboring pBar2 results in cell death upon induction of barnase expression wtih arabinose (right) but survival in the presence of glucose (left). Identical numbers of transformants were plated on arabinose and glucose plates.

An expression cassette encoding the efficient amber suppressor tRNA supe (Liu et al. *Chem. Biol.* 1999, 4, 685-691) was introduced into a separate plasmid, designated pSupE, containing a compatible origin of replication (FIG. 34B). These amber suppressor tRNA expression plasmids were transformed into competent cells harboring pBar2 plasmids and plated on growth media supplemented with carbenicillin (to ensure the presence of pSupE) and containing either glucose or arabinose, but lacking chloramiphenicol. It was hypothesized that even in the absence of chloramphenicol (which normally ensures maintenance of the pBar2 plasmid) the 10-20 copies of pBar2 per cell at the time of transformation would be sufficiently toxic in the presence of the amber suppressor tRNA to be lethal. Indeed, essentially no growth of cells harboring pBar2 and pSupE was observed on arabinose (FIG. 35B). In contrast, cells harboring pBar2 and pSupE were viable when grown in the presence of glucose (FIG. 35B).

Clearly, these results demonstrate that the amber suppression of plasmids expressing nonsense-mutated barnase genes is lethal to *E. coli* cells even in the absence of selective pressure to maintain the barnase-encoding plasmids. These findings suggest, therefore, that the rate of barnase-induced cell death is faster than the rate of spontaneous loss of all copies of the pBar2 plasmid.

Figure 36:
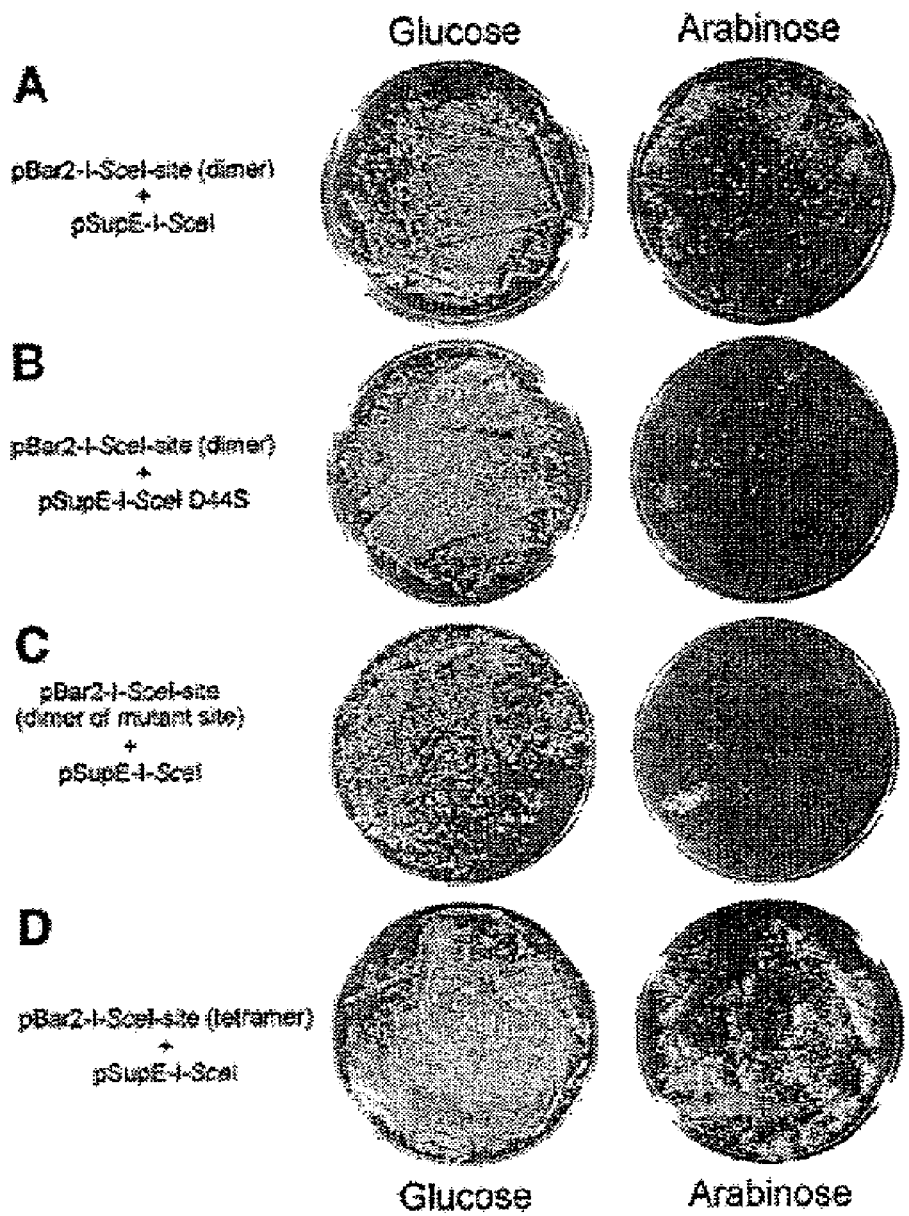
FIG. 36 depicts (A) the transformation of cells harboring pBar2-I-SceI-site with pSupE-I-SceI which results in significant cell survival upon induction with arabinose. (B) In contrast, the same selection strain transformed with pSupE-I-SceID44S encoding an inactive endonuclease results in very low survival rates on arabinose. (C) Repeating the assay in (A) with a pBar2-I-SceI-site variant in which one critical base of the I-SceI cleavage site has been mutated also results in non-viable cells. (D) Increasing the intracellular concentration of homing endonuclease substrate by using a variant of pBar2-I-SceI-site containing four copies of the I-SceI cleavage site results in a higher level of survival compared with the two-copy variant of pBar2-I-SceI-site shown in (A).

Linking Homing Endonuclease Activity and Specificity with Cell Survival: the homing endonuclease I-SceI was used to develop a link between homing endonuclease activity and the alleviation of pBar2-mediated toxicity. I-SceI is a monomeric 237 amino acid protein belonging to the LAGLIDADG family of homing endonucleases. This enzyme cleaves the 18 bp recognition sequence 5'-TAG GGA TAA//CAG GGT AAT-3' (SEQ ID NO: 1) leaving a 4 nt 3' overhang (see, Monteilhet et al. *Nucleic Acids Res.* 1990, 18, 1407-1413) Two repeats of this recognition sequence were ligated into the pBar2 plasmid affording pBar2-I-SceI site. The gene encoding I-SceI was subcloned into pSupE behind a constitutive lac promoter resulting in pSupE-I-SceI. When competent cells harboring pBar2-I-SceI-site were transformed with pSupE-ISceI under the conditions described above, significant levels of survival were observed (approximately 25%) on arabinose (FIG. 36A). As a control, the critical active site aspartate in the PI motif of I-SceI was mutated from Asp44 to Ser (Jurica et al. *Cell. Mol. Life. Sci.* 1999, 55, 1304-1326). When introduced into cells containing pBar2-I-SceI-site, the pSupE-I-SceI-D44S mutant was unable to yield visible colonies on arabinose at a significant rate (<1%; FIG. 36B). As an additional control, the selection using a mutant I-SceI recognition site (5'-TAG GGA TAA CAa GGT AAT-3') (SEQ ID NO: 2) was repeated that is known not to be cleaved by I-SceI (Monteilhet et al. *Nucleic Acids Res.* 1990, 18, 1407-1413; Colleaux et al. *Proc. Natl. Acad. Sci.* 1988, 85, 6022-6026; Beylot et al. *J. Biol. Chem.* 2001, 276, 25243-25253). Transformation of the selection strain containing this mutant recognition site with wild-type pSupE-I-SceI also resulted in very low levels of survival on arabinose (FIG. 36C). Taken together, these results demonstrate that the selection system described above successfully links cell survival with both homing endonuclease activity and DNA sequence specificity.

In addition to the selection strain harboring pBar2-I-SceI-site containing two copies per plasmid of the I-ScI cleavage site (FIG. 36A), a selection strain with a pBar2-I-SceI-site variant containing four copies per plasmid of the wild-type cleavage site was also generated and characterized. When transformed with pSupE-I-SceI, the four-copy variant reproducibly survived at an approximately 2-fold higher rate compared with the survival rate of the two-copy strain, consistent with the hypothesis that elevating the concentration of substrate DNA sites in vivo increases the efficiency of pBar2 cleavage (FIG. 36D). This result suggests that the stringency of the homing endonuclease selection can be modulated by varying the number of nuclease cleavage sites in the pBar2 plasmid. Variants of pBar2 containing more than four copies of endonuclease cleavage sites proved to be unstable when propagated in E. coli.

A Sensitive In vivo Activity Assay for Homing Endonucleases: The suitability of the selection system described above as a general and semi-quantitative assay for homing enconucleases activity and site specificity was next evaluated. To test the generality of the strategy, selection systems were established similar to the I-SceI system described above for two additional homing endonucleases: PI-SceI and I-ScaI. Although these enzymes also belong to the LAGLIDADG (SEQ ID NO: 36) endonuclease family, there is no appreciable sequence sites (16, 18 and approximately 30 base pairs for I-ScaI, I-SceI and PI-SceI respectively) vary significantly and the DNA sequences cleaved by these enzymes are unrelated (Monteilhet et al. *Nucleic Acids Res.* 2000, 28, 1245-1251; Wende et al. *Nucleic Acids Res.* 1996, 24, 4123-4132; Monteilhet et al. *Nucleic Acids Res.* 1990, 18, 1407-1413), suggesting that a selection system compatible with all three enzymes would likely be applicable to homing endonucleases in general.

Figure 37:
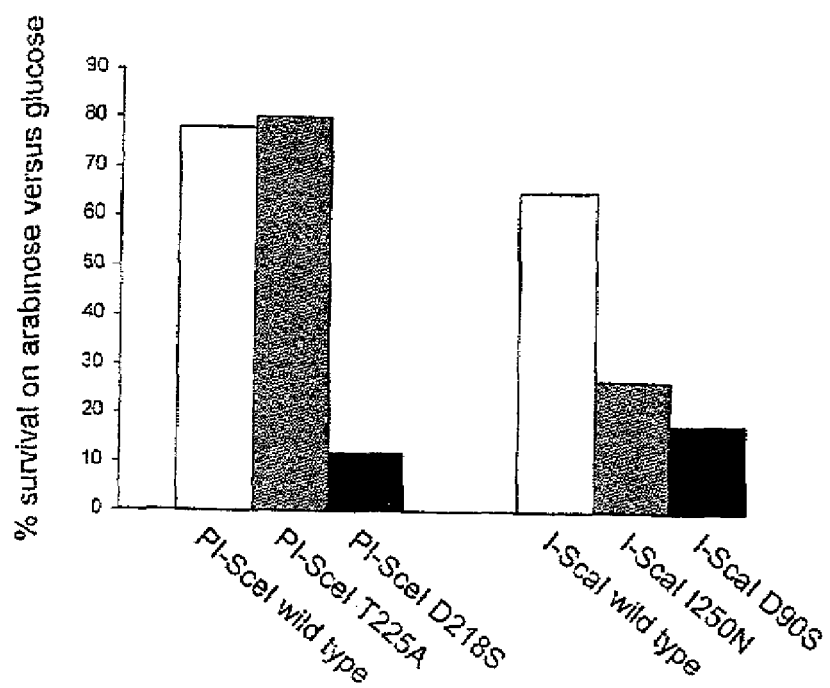
FIG. 37 depicts quantitative analysis of the activities of six homing endonuclease variants of I-ScaI and PI-SceI. Cells harboring pBar2-PI-SceI-site (left three bars) or pBar2-I-ScaI-site (right three bars) were transformed with the pSupE-nuclease plasmids encoding the six nucleases listed and processed as described in the Materials and Methods. The percentage of surviving colonies on arabinose-containing media relative to the number of colonies arising from an identical number of transformants plated on glucose-containing media is shown for each nuclease. Values reflect the average of three independent trials and standard deviations were <15% of each value reported.

Wild-type pSupE-PI-SceI and pSupE-I-ScaI plasmids were generated as well as variants encoding the catalytically inactive D218S (Christ et al. *EMBO J.* 1999, 18, 6908-6916) and D90S (Szczepanek et al. *Mol. Gen. Genet.* 2000, 264, 137-144) mutants of PI-SceI and I-ScaI, respectively. Plasmids pBar2-PI-SceI site and pBar2-I-ScaI-site containing the wild-type cleavage sites of these two homing endonucleases were also constructed. For both the PI-SceI and I-ScaI enzymes high survival rates of cells containing the wild-type pSupE-nuclease plasmid and teh matched pBar2-site wild-type cleavage site was observed when grown in the presence of arabinose (FIG. 37). In contrast, cells expressing the inactive nuclease mutants survived on arabinose at a much lower rate (FIG. 37). To further evaluate the utility of this assay, mutant pSupE plasmids expressing mutant endonucleases with previously characterized activities were constructed. For I-ScaI the I250N mutant was chosen that possesses activity too low to detec in vitro but which can be observed in vivo (Szczepanek et al. *Mol. Gen. Genet.* 2000, 264, 137-144), while for PI-SceI the T225A mutant was used that exhibits slightly higher activity in vitro than wild-type PI-SceI (He et al. *J. Biol. Chem.* 1998, 273, 4607-4615). The signals generated by these mutant enzymes (the percentage of colonies surviving selection on arabinose versus on glucose) were compared with those generated by the wild-type enzymes (FIG. 37). The wild-type I-ScaI nuclease induces survival on arabinose at a 65% rate relative to survival on glucose. In contrast, the I250N I-ScaI mutant causes survival at a 27% rate, while cells expressing the inactive D90S mutant survive at an 18% rate. among PI-SceI variants, the wild-type enzyme results in 78% survival under selection conditions, while cells expressing the T225A mutant survive at an 80% rate (not statistically distinguishable from the wild-type survival rate) and those expressing the inactive D218S mutant survive at a 12% rate. These results are consistent with the previously reported relative activities of those homing endonuclease variants and suggest that the selection system described above can serve as a general semiquantitative in vivo assay for homing endonuclease activity.

As described above, an in vivo selection system for *E. coli* for homing endonuclease-catalyzed DNA cleavage is provided by the present invention. In this system, one plasmid contains a cleavage site of interest together with a caged toxic gene, while a second plasmid encodes the homing endonuclease to be studied and a suppressor tRNA that enables the functional expression of the toxic gene. In the absence of homing endonuclease activity, cells harboring both plasmids are largely not viable in media containing arabinose. The small amount of background growth observed under these conditions is likely due to the rare but detectable rejection of all, or nearly all, copies of the pBar2 plasmid by the cells in the absence of the plasmid maintenance marker (chloramphenicol) during recovery and selection. Consistent with this hypothesis, it has been found that the majority of these background colonies are chloramphenicol sensitive. Expression of an active homing endonuclease presumably leads to cleavage of its recognition site on the pBar2 plasmid, degradation of the linearized pBar2 DNA, and reduction of the pBar2 copy number to an extent that the resulting cells are viable in the presence of arabinose. The system was evaluated for three homing endonucleases that all belong to the LAGLIDADG (SEQ ID NO: 36) family (I-ScaI, I-SceI, and PI-SceI), and in each case an active enzyme-substrate combination was required for cell survival.

These results suggest that this selection system can be used as a sensitive in vivo activity assay for studying combinations of double-strand cleaving homing endonucleases and cleavage sites of interest. A selection strain containing a pBar2 plasmid and a cleavage site of interest allows the semi-quantitative determination of the ability of wild-type or mutant homing endonucleases to cleave that site. Each assay is internally controlled by comparing survival under selection conditions (in the presence of arabinose) with the survival in the absence of selective pressure (in the presence of glucose). This internal control normalizes the signal relative to the total number of transformants and corrects for differences in transformation efficiencies between experiments, although variable expression levels among different endonuclease mutants may also affect survival rates. The endpoints of the signal are conveniently calibrated by measuring the survival rates of wild-type and inactive mutants under selection conditions.

Traditionally, the effect of site-directed or random mutagenesis on the activity of homing endonucleases is determined by in vitro DNA cleavage using purified nucleases and subsequent gel electrophoresis of the resulting DNA fragments. The system described here circumvents laborious protein overexpression and purification and involves simple plasmid transformation and cell plating rather than in vitro cleavage assays. In addition, the ability of this selection to detect cleavage activity of the I250N mutant of I-ScaI-activity that was not detectable by in vitro assay, but is known to exist in vivo (Szczepanek et al. *Mol. Gen. Genet.* 2000, 264, 137-144)-suggests that this system may be able to detect low levels of activity difficult to observe using traditional in vitro endonuclease assay methods. Finally, in vivo selection allows enzyme activities to be assayed in the living cell under complex conditions that in some cases may be more relevant than artificial in vitro conditions. This selection system should, therefore, facilitate structure-function analyses of homing endonucleases and moreover may assist the study of other sequence-specific DNA cleavage agents capable of functioning in living cells.

The successful development of an in vivo selection system linking homing endonuclease activity and specificity with cell survival may also enable the evolution of homing endonucleases with altered cleavage specificities. Mutant endonucleases capable of cleaving DNA sequences of interest may be selected using libraries of pSupE-nuclease plasmids and pBar2 variants containing desired cleavage sites.

(FIG. 21). As a simple validation of this approach, we have constructed a pSitesBar2-SceI variant in which the wild-type recognition sequence TAGGGATAACAGGGTAAT (SEQ ID NO: 1) has been replaced by the single mutant sequence TAGGGATAACAaGGTAAT (SEQ ID NO: 2). Base G12 in this substrate has been biochemically characterized as one of the most crucial recognition elements of I-SceI nuclease, and mutations at this position abolish cleavage activity (L. Colleaux, et al. *Proc. Natl. Acad. Sci. USA* 1988, 85, 6022-6). The basis for recognition of this position is not understood, and no high-resolution structure of the I-SceI homing endonuclease has been solved. The evolution and characterization of mutant enzymes capable of cleaving sites varying at base 12 would identify residues important in the DNA sequence recognition of I-SceI. Together with negative selections to narrow the specificity of evolved nucleases, these studies may also reveal the degree to which specific residues must work together to recognize a base in the substrate, versus the possibility of one residue per base recognition as has been observed (see, S. A. Wolfe, et al. *Annu. Rev. Biophys. Biomol Struct.* 2000, 29, 183-212) in some zinc finger proteins. Libraries of I-SceI mutants are currently being generated using DNA shuffling and selecting for cleavage of our new target site.

As a second target for our nuclease evolution efforts, a triply mutated variant of the I-ScaI recognition site has been chosen that is identical to a sequence found in a viral genome (FIG. 21). Whereas I-ScaI normally cleaves TGAGGTGCACTAGTTA (SEQ ID NO: 3), we seek to evolve mutant I-ScaI nucleases capable of cleaving TGAGGTGCACTAtTat (SEQ ID NO: 4), a sequence present in the gp120 gene of HIV-1. To maximize the likelihood of evolving a mutant I-ScaI capable of efficiently and specifically cleaving this target, and to gain more detailed insights into the basis of each change in specificity, a stepwise approach in addition to a direct strategy has been adopted. Two single mutant, one double mutant, and the triple mutant variants of pSitesBar2-ScaI have been constructed. Both the stepwise evolution of libraries of I-ScaI towards the recognition of the singly and doubly mutated intermediates, as well as the direct evolution of I-ScaI towards recognition of the triply mutated target can be conducted.

Materials and Methods

A) Plasmid Construction: To construct plasmid p-SupE-nuclease, a cassette containing a supE suppressor tRNA under control of the lpp promoter and rrnC terminator was amplified by PCR from plasmid pACsupE (see, Liu et al. *Proc. Natl. Acad. Sci. USA*, 1999, 96, 4780-4785) and subcloned into the large NotI-KpnI fragment of pbluescript II SK(+)-Nco (which is an A823G mutant of pBluescript II SK(+) containing a NcoI site) to provide pSupE. The genes encoding the homing endonucleases I-SceI, I-ScaI and PI-SceI were amplified by PCR from plasmids pSCM525 (see, Perrin et al. *EMBO J.* 1993, 12, 2939-2947), pET 11-p28 bi2 (Monteilhet et al. *Nucleic Acids Res.* 2000, 28, 1245-1251), and pHisVDE (Wende et al. *Nucleic Acids Res.* 1996, 24, 4123-4132), respectively, and subcloned into the large NcoI-NotI fragment of pSupE under the control of the constituitive lac promoter to afford the pSupE-nuclease plamids. PCR primers used to amplify genes encoding the supE expression cassette and the I-SceI, I-ScaI and PI-SceI homing endonucleases were as follows: 5'-TATGCATAACGCGGCCGC-CCCGAGGGCACCTGTCCTAC-3' (SEQ ID NO: 5) and 5'-TATCTGGGTACCGCATGCACCATTCCTTGCGG-3' (SEQ ID NO: 6) for the supE cassette; 5'-AGCTCCATG-GCAATGAAAAACATCAAAAAAAACCAGG-3' (SEQ ID NO: 7) and 5'-TATCAAATGCGGCCGCTTATTATTTCAG-GAAAGTTTCGGAGG-3' (SEQ ID NO: 8) for I-SceI, 5'-AGCTCCATGGAATATACCATGCTGATTAAAAG-3' (SEQ ID NO: 9) and 5'-TATCAAATGCGGCCGCTTATTA-CAGATAGTTGCCCAG-3' (SEQ ID NO: 10) for I-ScaI, and 5'-AGCTCCATGGGATCCGCATGCTTTGCCAAAG-3' (SEQ ID NO: 11) and 5'-TATCAAATGCGGCCGCTCAT-CAGCAATTATGGACGACAACC-3' (SEQ ID NO: 12) for PI-SceI.

Plasmid pBar2 was constructed by ligating the ClaI-SphI fragment from pYsupA38B2 (see, Liu et al. *Proc. Natl. Acad. Sci. USA*, 1999, 96, 4780-4785) containing araC and a two amber codon variant of barnase (Bar2) under the control of the pBAD promoter into the large ClaI-SphI fragment of pACYC184 to provide pACYC-Bar2. In addition, a TGACGCCATTATCTATGTCGGGTGCG-GAGAAAGAGGTAATGAAATGGCAGAAGTCT TGATGGAT-3' (SEQ ID NO: 13) and 5'-GATCATCCAT-CAAGACTTCTGCCATTTCATTAC-CTCTTTCTCCGCACCCGACATAGAT AATGGCGTCA-GAT-3' (SEQ ID NO: 14) (recognition site of PI-SceI underlined). Inserts containing multiple copies of the cleavage sites were obtained by self-ligation of the synthetic cassettes and gel purification of double-stranded fragments of the desired lengths. For I-SceI selections, pBar variants containing a dimer or a tetramer of the recognition site were used. For I-ScaI selections a trimer of the recognition site was used, and for PI-SceI selections a pBar variant containing a single copy of the recognition site was used. Variants of pBar containing more than four copies of any nuclease recognition sequence proved to be unstable in *E. coli* over many cell divisions. The relevant portions of all constructed plasmids were verified by automated DNA sequencing.

B) Selections: Selection strains were constructed by transformations of *E. coli* strain DH10B (Gibco BRL) with the appropriate variant of pBar2. Transformants were grown in 2× YT in the presence of chloramphenicol (40 µg/ml) and glucose (0.5%), and electrocompetent cells of the selection strains were prepared following standard procedures (Tabor, S, and Struhl, K (1989) *Current Protocols in Molecular Biology*. John Wiley and Sons, New York). For selections, typically 40 µl of competent cells were transformed with 10-100 ng of the appropriate variant of pSupE-nuclease. After electroporation, cells were immediately recovered in 2×YT+ glucose (0.5%) and shaken at 37° C. for 15-20 min. In order to estimate the total number of transformants, an aliquot of cells was plated on 2×YT+ glucose (0.5%)+carbenicillin (125 µg/ml). A second aliquot of cells was washed with 2×YT and plated on 2×YT+arabinose (0.5%)+carbenicillin (125 µg/ml). All plates were incubated at 37° C. for 8-18 hours until colonies were clearly visible.

C) In vivo activity assays: Different pSupE nuclease variants were adjusted to approximately equal concentrations (determined by gel densitometry and quantitation of the number of transformants under non-selective conditions), and selections were carried out as described above. Colonies surviving on glucose were used as an internal standard defined as 100% survival. For PI-SceI, the signal-to-background ratio was improved by an additional incubation at 37° C. for 1 hour in 2×YT+125 mg/ml carbenicillin+0.5% arabinose prior to plating. For the enzyme I-ScaI, the optimal signal-to-background ratio was observed by pre-incubating the transformants in 2×YT+125 µg/ml carbenicillin+0.5% glucose for 6 h at 37° C. prior to plating.

Example 2

An in vivo Selection System for Recombinase Activity

Initial efforts to link cell survival with recombinase activity focused on Cre recombinase and its 34 base pair loxP substrate. It was hypothesized that recombination could be positively linked to cell survival by either (i) flanking a gene encoding a toxic protein by loxP sites, or (ii) disrupting an essential gene with an intervening segment of "junk DNA" flanked by loxP sites (FIG. 4). In the former case, recombination excises the toxic gene from the plasmid, rendering the plasmid non-toxic. Because nearly all copies of the toxic gene may need to be removed in order for the cells to be viable, this scheme represents a stringent selection. In the latter case, recombination rejoins two halves of an essential gene, allowing the cell to survive. Since only a small number of copies of the recombined essential gene may be sufficient to confer survival, this strategy may serve as a more sensitive and less stringent selection. We pursued both strategies.

The choice of an essential gene was guided by several factors. Most selections in bacterial cells to date have used metabolic genes such as those encoding β-galactosidase (lactose metabolism) (D. R. Liu, et al Proc. Natl. Acad. Sci. USA 1997, 94, 10092-10097), thymidylate synthase (thymidine biosynthesis) (D. W. Wood, et al. Nat. Biotechnol. 1999, 17, 889-92) oxidosqualene-lanosterol cyclase (sterol biosynthesis) (see, E. A. Hart, et al. J. Am. Chem. Soc. 1999, 121, 9887-9888) or phosphoribosyl-anthranilate isomerase (tryptophan biosynthesis) (M. M. Altamirano, et al. Nature 2000, 403, 617-22). In vivo selections based on metabolic gene complementation, however, have at least two potential drawbacks. First, because many metabolic gene products ultimately impinge on fundamental, essential cellular functions such as protein biosynthesis, cells may require a significant amount of a metabolic gene product in order to survive (P. A. Patten, et al. Molecular Diversity 1995, 1, 97-108). In practice, this would reduce the sensitivity of a recombinase positive selection because cells harboring weak levels of desired recombinase activity may not generate enough metabolic gene product to confer viability. Second, an ideal selection has an adjustable stringency such that early in the evolution process stringency can be set low, while in later rounds a high level of stringency ensures that only the most active enzymes survive the selection. The stringency of metabolic gene product complementation can be difficult to tune because there is often no simple and predictable way of adjusting the concentration of upstream substrates or downstream products to modulate the level of metabolic protein activity needed for cell survival. Two antibiotic resistance genes, TEM-1 β-lactamase ($amp^r$, encoding an ampicillin resistance protein) and aminoglycoside 3'-phosphotransferase ($kan^r$, encoding a kanamycin resistance protein), as the essential genes for our positive selection system were tested. It was hypothesized that the non-metabolic nature of these antibiotic resistance enzymes would increase the sensitivity of our selections, and that varying the concentration of antibiotic in the growth media would modulate the stringency of the selection (D. R. Liu et al. Proc. Natl. Acad. Sci. USA 1999, 96, 4780-4785).

Figure 5:
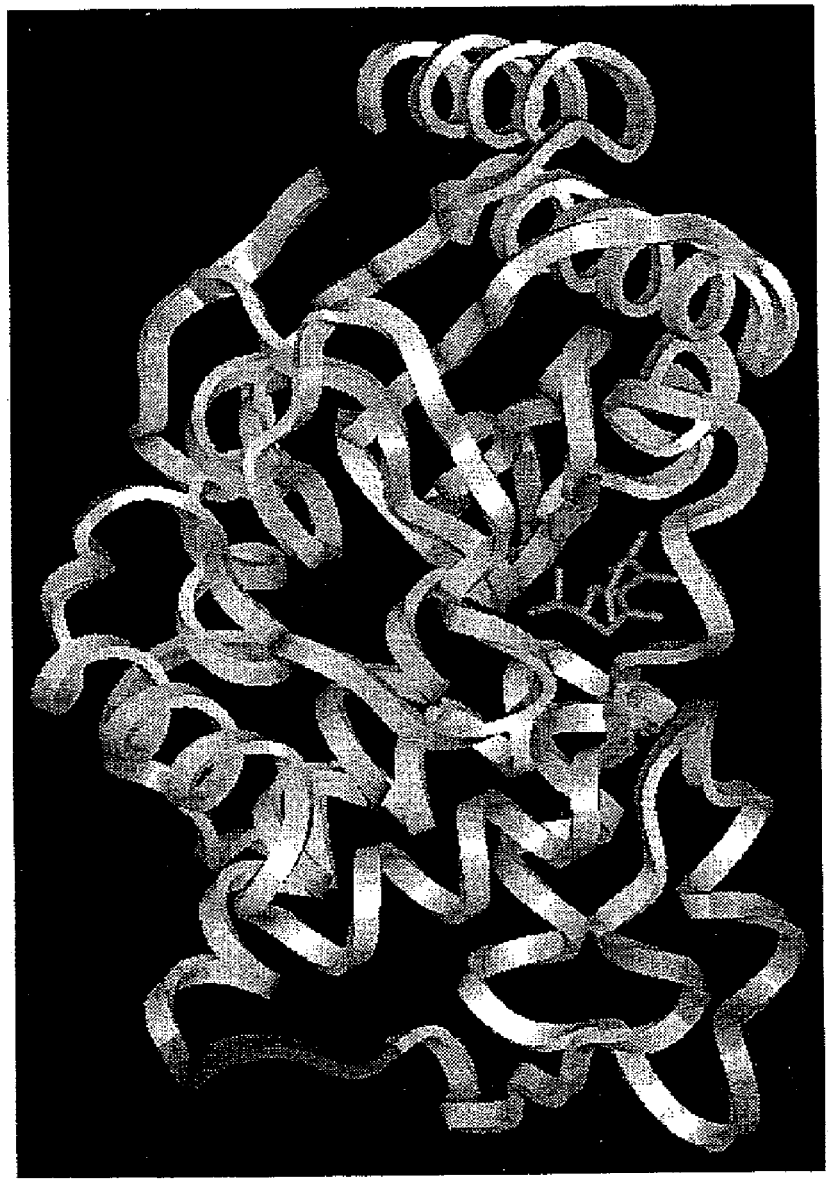
FIG. 5 depicts the location of intervening DNA in the ampr or kanr genes based upon an examination of the crystal structure of β-lactamase or of a kanr homolog.
Figure 6:
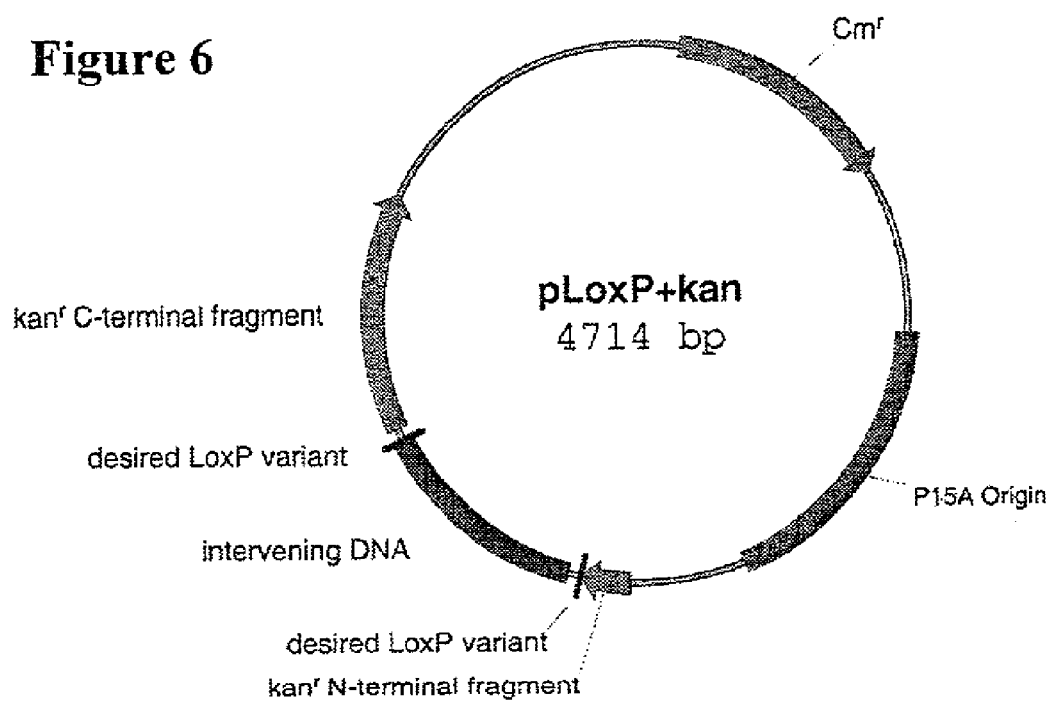
FIG. 6 depicts plasmids (pLoxP+amp and pLOxP+kan).
Figure 7:
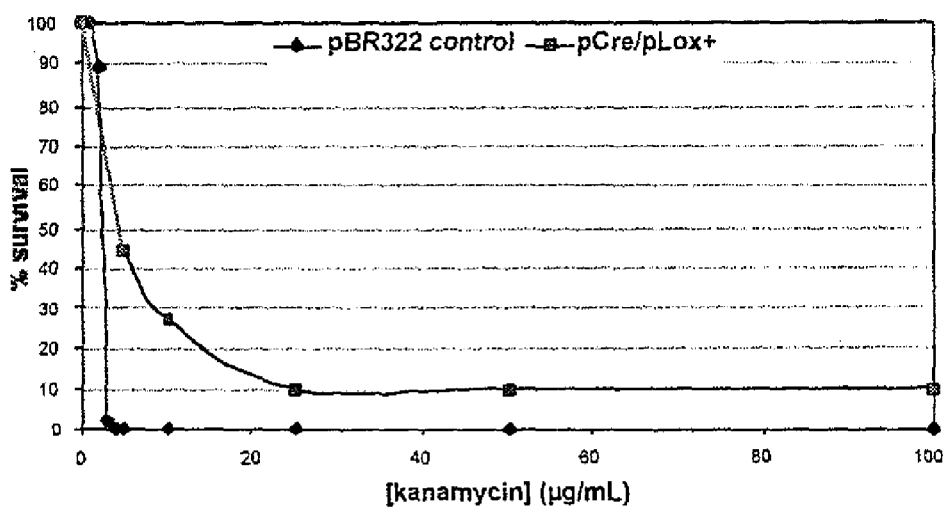
FIG. 7 depicts differences in antibiotic resistance for cells harboring the wild-type Cre expression plasmid versus a control plasmid (pBR322) lacking the Cre gene.

Using standard cloning methods, DNA plasmids were constructed in which constitutively expressed $amp^r$ or $kan^r$ genes were disrupted with a segment of unrelated DNA 2,500 base pairs in length. The intervening DNA segment was flanked by two loxP sequences. The location of the intervening DNA in the $amp^r$ or $kan^r$ genes was chosen based on an examination of the crystal structure of β-lactamase (C. Jelsch, et al. Proteins 1993, 16, 364-83) or of a $kan^r$ homolog, (W. C. Hon, et al. Cell 1997, 89, 887-95) aminoglycoside kinase. Because Cre-mediated recombination leaves behind a 34 base pair loxP "footprint" that translates to yield a 12 residue peptide (ITSYSIHYTKLS)(SEQ ID NO: 37), the 2,500 base pair intervening sequence was inserted into a loop away from the active site and having a high B-factor in each antibiotic resistance protein to maximize the likelihood that the post-recombination footprint would not disrupt antibiotic resistance (FIG. 5). Translation of the disrupted $amp^r$ or $kan^r$ gene was predicted to terminate within the intervening segment and therefore not confer antibiotic resistance in the absence of Cre-mediated recombination. Indeed, the resulting plasmids (pLoxP+amp and pLoxP+kan, FIG. 6) did not confer kanamycin or ampicillin resistance in the absence of Cre expression. We also constructed the mock-recombination product of pLoxP+amp and confirmed that the 12 residue footprint left behind after recombination did not abolish the ability of the modified ampr protein to confer high levels of ampicillin resistance ($IC_{50}$ (ampicillin)=400 µg/mL). To test if this positive selection system links Cre activity with cell survival through antibiotic resistance, competent E. coli DH10B cells harboring pLoxP+kan or pLoxP+amp were transformed with an IPTG-inducible Cre expression plasmid (Q. Liu, et al. Curr. Biol. 1998, 8, 1300-9) and plated on media containing ampicillin or kanamycin following an induction period. Even after optimizing the temperature (30-37° C.), induction time (1 h to 24 hours), and the concentration of antibiotic in the selection media (2 to 1,000 µg/mL), only modest differences in antibiotic resistance were observed for cells harboring the wild-type Cre expression plasmid versus a control plasmid (pBR322) lacking the Cre gene (FIG. 7). Western blot analysis using anti-Cre polyclonal antibodies (BAbCO) confirmed the expression of Cre protein in our selection cells. The slightly increased $IC_{50}$ values resulting from wild-type Cre recombination was judged to be insufficient for use as a general recombinase positive selection. In case the lack of robust antibiotic resistance observed above arose from a flaw in our selection design, the alternative positive selection strategy in which toxic genes flanked by loxP sequences are excised by Cre-catalyzed recombination was also examined. The extreme toxicity of barnase, an RNA-cleaving enzyme from Bacillus amyloliquefaciens, has been extensively characterized (D. R. Liu et al. Proc. Natl. Acad. Sci. USA 1999, 96, 4780-4785; D. D. Axe, et al. Proc. Natl. Acad. Sci. USA 1996, 93, 5590-5594; M. Jucovic Proc. Natl. Acad. Sci. USA 1996, 93, 2343-7).

Figure 8:
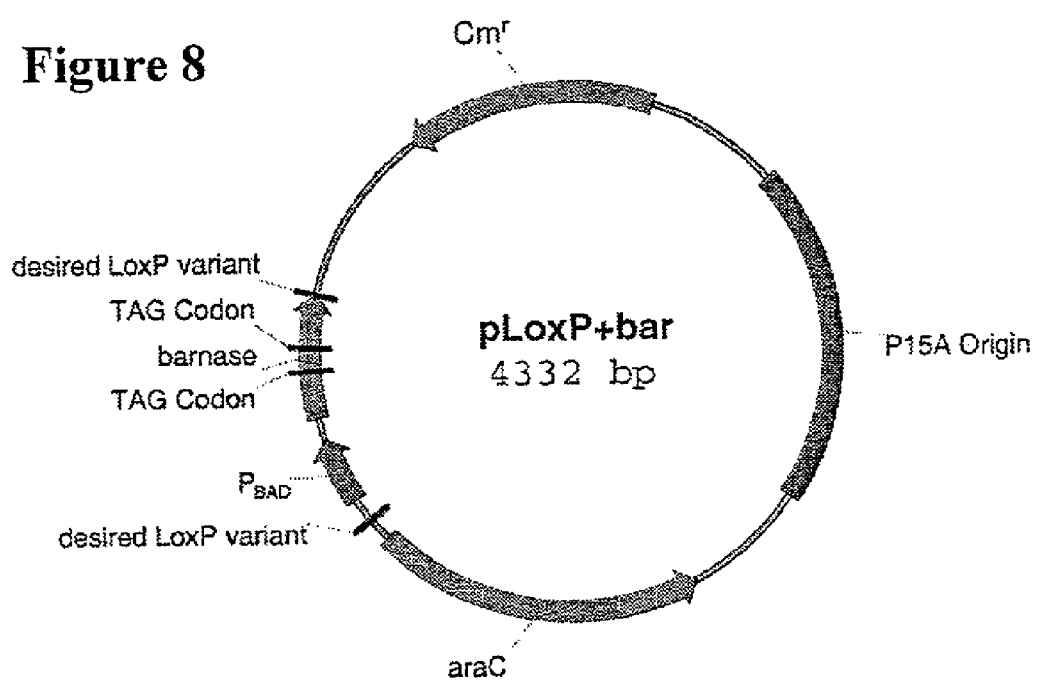
FIG. 8 depicts a DNA plasmid (pLoxP+bar) in which a barnase expression cassette under control of the tightly regulated $P_{BAD}$ promoter (inducible with arabinose and repressible with glucose) was flanked by loxP sequences.

A DNA plasmid (pLoxP+bar) in which a barnase expression cassette under control of the tightly regulated $P_{BAD}$ promoter (inducible with arabinose and repressible with glucose) (L. M. Guzman, et al. J. Bacteriol. 1995, 177, 4121-30) was flanked by loxP sequences (FIG. 8) was constructed. Consistent with our design, in the absence of Cre expression, cells harboring pLoxP+bar were not viable when barnase expression was induced with arabinose. Cell harboring both pLoxP+bar and a Cre expression plasmid demonstrated an increased ability to survive when barnase expression was induced, but only to an unacceptably low extent (<20% survival after 4 h pre-induction incubation). Although Cre has been used in a few examples (Y. G. Yoon, et al. Genet. Anal 1998, 14, 89-95; Q. Liu, et al. Methods Enzymol. 2000, 328, 530-49; D. Sblattero et al. Nat. Biotechnol. 2000, 18, 75-80) to recombine DNA in E. coli cells, we began to suspect that Cre was not expressed at sufficiently high levels or in a sufficiently active form to support the selections described above. The Flp-FRT recombinase system was then explored as a potentially more tractable target for developing our in vivo selections.

Figure 9:
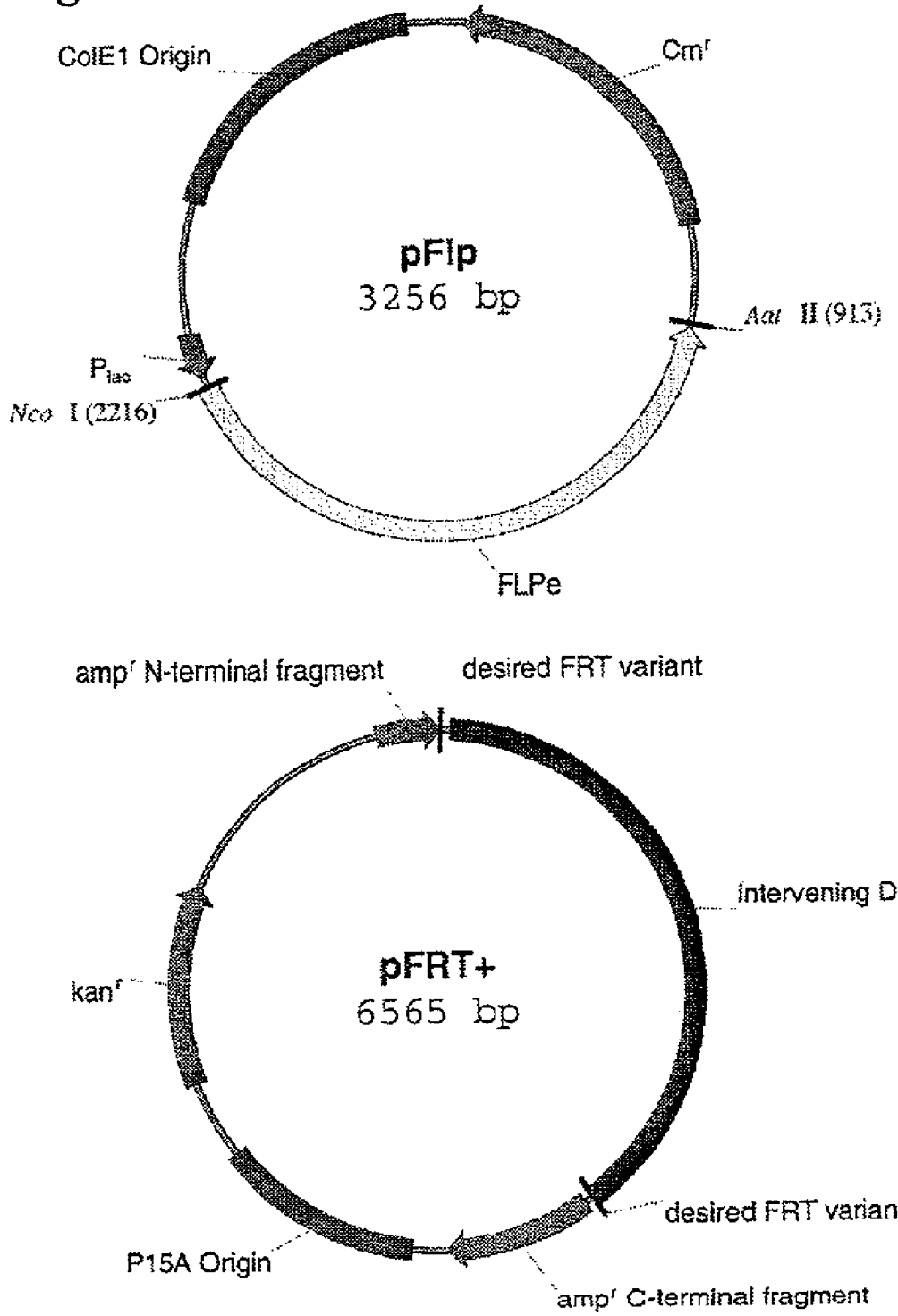
FIG. 9 depicts the subcloning into a constitutive expression plasmid the gene encoding a thermostable Flp recombinase mutant yielding pFlp, and also depicts the replacement of the loxp sites in the positive selection plasmid pLoxP+amp by FRT sites to afford pFRT+.

We subcloned into a constitutive expression plasmid the gene encoding a thermostable Flp recombinase mutant recently isolated by Stewart and co-workers using a β-galactosidase screen (F. Buchholz, et al. *Nat. Biotechnol.* 1998, 16, 657-62) yielding pFlp (FIG. 9). The loxP sites in the positive selection plasmid pLoxP+amp were replaced by FRT sites to afford pFRT+ (FIG. 9). *E. coli* cells harboring pFRT+ and a control plasmid lacking the Flp gene were unable to grow in the presence of 5 μg/mL or higher ampicillin. The mock recombination product of pFRT+ was then constructed, inserting 12 amino acids (RSSYSLESIGTS) into a disordered loop in amp$^r$, and found that this mock-recombined plasmid was able to confer ampicillin resistance at 400 μg/mL.

Figure 10:
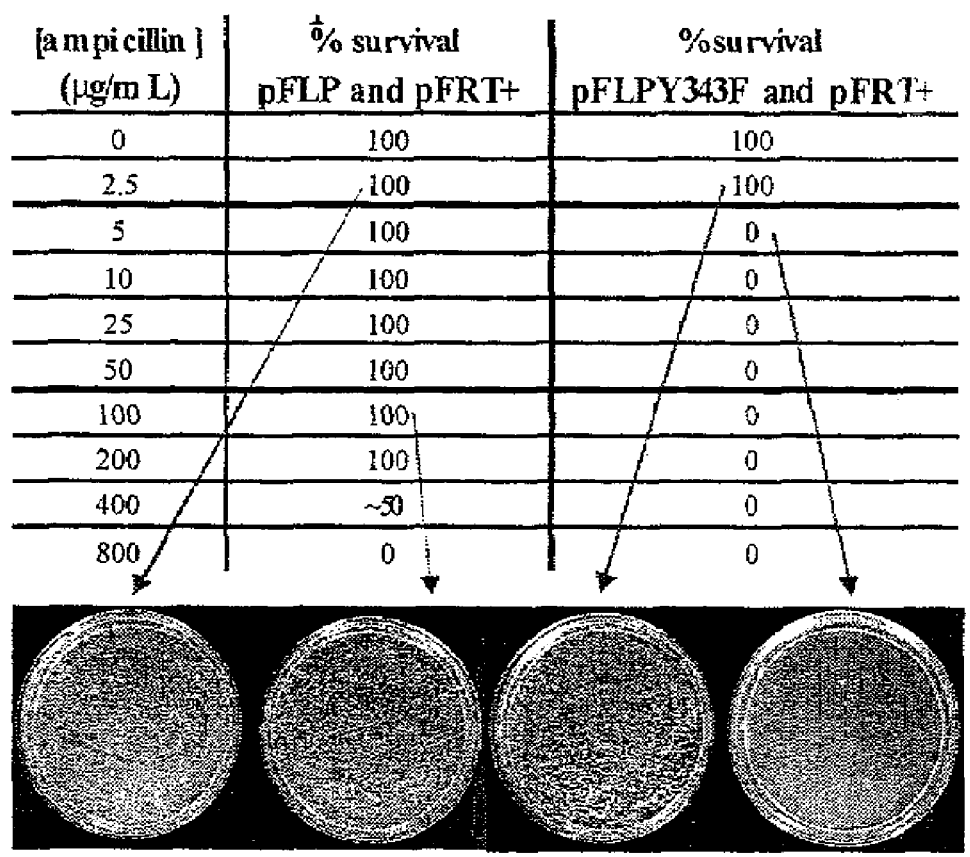
FIG. 10 depicts that cells harboring both pFRT+ and pFlp demonstrated robust ampicillin resistance and were able to grow in the presence of 400 μg/mL ampicillin.
Figure 11:
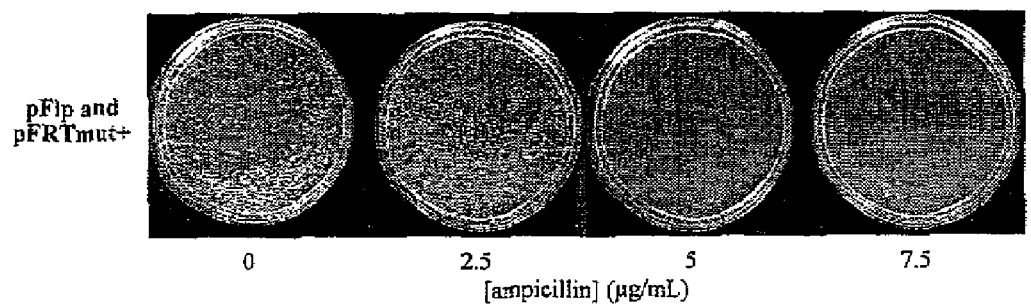
FIG. 11 depicts that cells harboring wild-type pFlp and a mutant pFRT+ (pFRTmut+) in which four critical bases in each FRT half site were mutated also failed to confer ampicillin resistance indicating that cell survival in this system also relies on the substrate specificity of the expressed recombinase.
Figure 12:
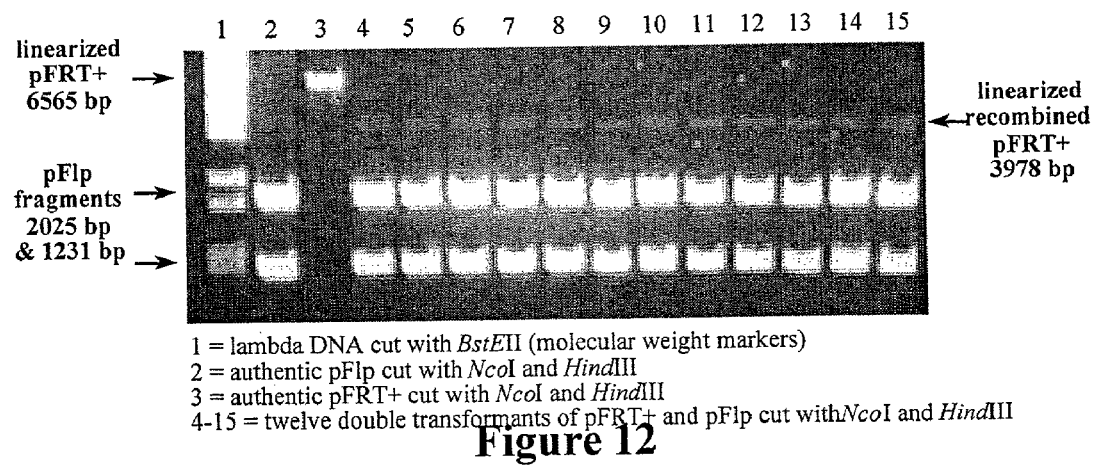
FIG. 12 depicts the loss of a 2,500 base pair DNA fragment by all double transformants consistent with the Flp-catalyzed recombination of pFRT+.

Grafifyingly, cells harboring both pFRT+ and pFlp demonstrated robust ampicillin resistance and were able to grow in the presence of 400 μg/mL ampicillin (FIG. 10), consistent with the Flp-catalyzed recombination of pFRT+. Using site-directed mutagenesis, we mutated the catalytic Tyr 343 in Flp to Phe (pFlpY343F), rendering the recombinase completely inactive. Cells harboring pFRT+ and pFlpY343F were unable to grow in the presence of 5 μg/mL or higher ampicillin (FIG. 10), demonstrating that Flp recombinase activity is essential for cell survival in this system. Similarly, cells harboring wild-type pFlp and a mutant pFRT+ (pFRTmut+) in which four critical bases in each FRT half site were mutated (see below) also failed to confer ampicillin resistance (FIG. 11), indicating that cell survival in this system also relies on the substrate specificity of the expressed recombinase. To confirm in vivo recombination, plasmid DNA isolated from pFlp/pFRT+ double transformants was characterized by restriction digestion. All double transformants analyzed unambiguously show the loss of a 2,500 base pair DNA fragment consistent with the Flp-catalyzed recombination of pFRT+ (FIG. 12). To our knowledge, these results demonstrate for the first time an in vivo selection linking site-specific recombinase activity and specificity to the survival of a bacterial cell. We are currently characterizing the dynamic range and sensitivity of the selection by making, purifying, and assaying in vitro mutant Flp enzymes with intermediate activities and characterizing their phenotypes in our positive selection at varying concentrations of ampicillin.

Evolving Recombinase Enzymes with New DNA Specificities: Using this positive selection system, libraries of mutant Flp enzymes towards new DNA specificities have begun to be evolved. The crystal structure of the Flp-FRT complex (Y. Chen, et al. *Mol. Cell.* 2000, 6, 885-97) together with biochemical studies (J. F. Senecoff, et al. *J. Mol. Biol.* 1988, 201, 405-21) implicate several sets of specific interactions between bases in FRT and residues of Flp. The C-terminal domain of Flp contacts both the major and minor groove of the FRT inverted repeats but makes no base-specific contacts with the core region. Two sets of interactions are especially notable: Lys 285 makes a hydrogen bond with O2 of T in base pair 13, and Arg 281 forms a bidentate hydrogen bond with O6 and N7 of G in base pair 11. The N-terminal domain of Flp makes a variety of non-base specific contacts with FRT in addition to a hydrogen bond between Lys 82 and G in base pair 5 (Y. Chen, et al. *Mol. Cell.* 2000, 6, 885-97). Consistent with many of these structural findings, a comprehensive mutational analysis of FRT (J. F. Senecoff, et al. *J. Mol. Biol.* 1988, 201, 405-21) has previously identified bases G5, A7, and G11 in FRT as particularly intolerant of mutation.

Figure 14:
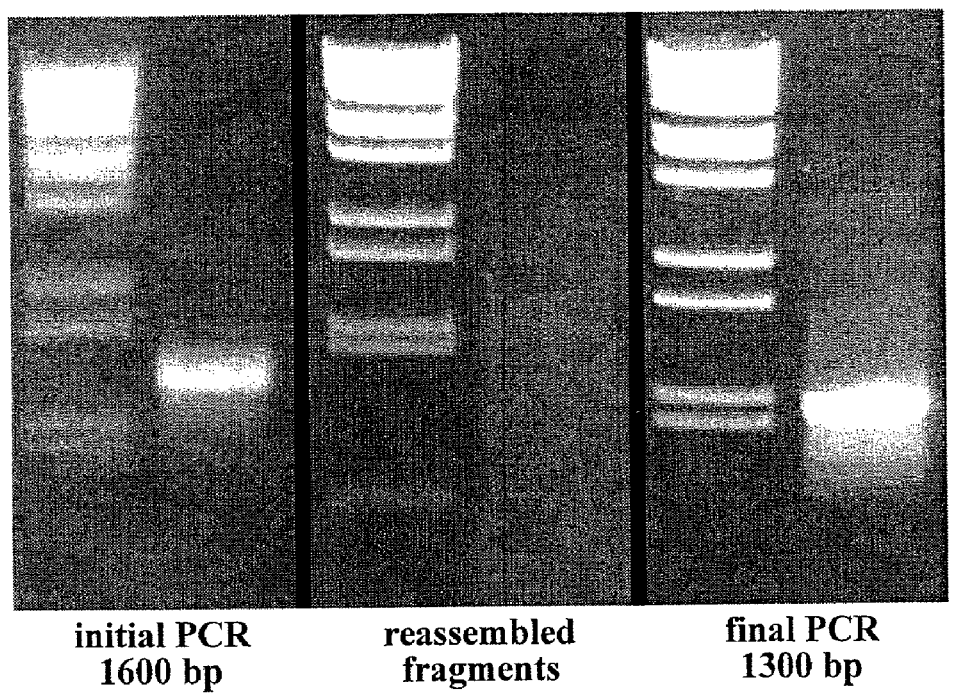
FIG. 14 depicts the generation of large libraries of mutant Flp recombinase genes using DNA shuffling.
Figure 15:
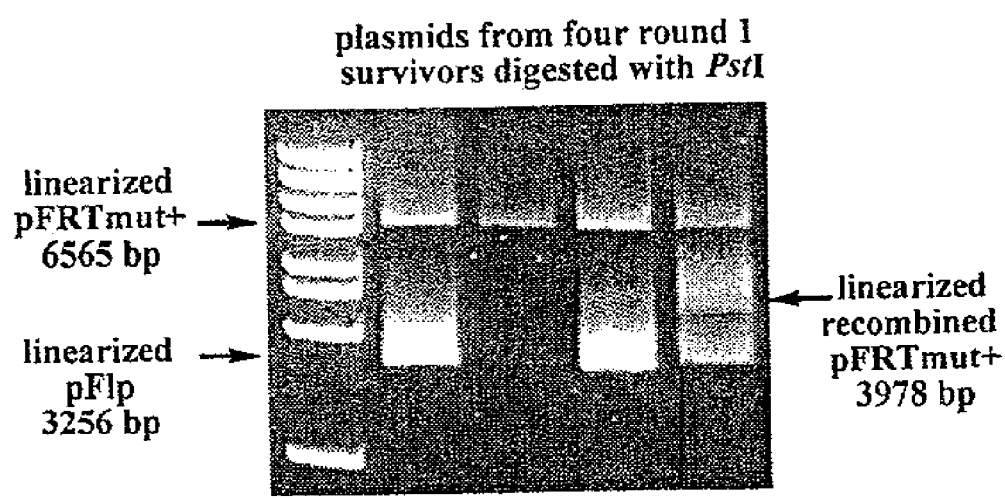
FIG. 15 depicts the in vivo recombination of pFRTmut+ in at least two surviving colonies by restriction digestion of plasmid DNA isolated from round one survivors demonstrating the loss of a 2,500 base pair DNA fragment.
Figure 16:
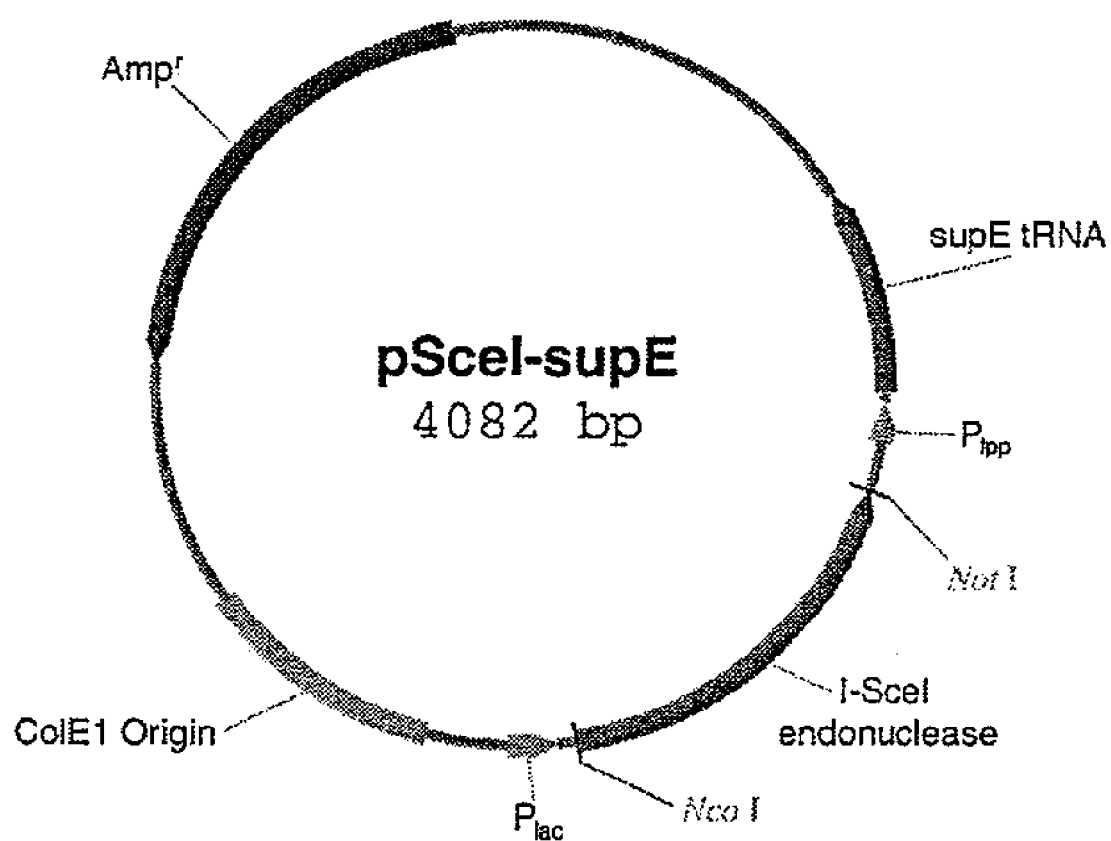
FIG. 16 depicts the introduction of expression cassettes encoding either a strong (supE) or a weak (sup123) amber suppressor tRNA into plasmids I-SceI, PI-SceI, or I-ScaI to afford a total of six ampicillin resistant plasmids, pScel-supE, pScel-sup123, pPIScel-supE, pPIScel-sup123, pScaI-supE, and pScaI-sup123.
Figure 17:
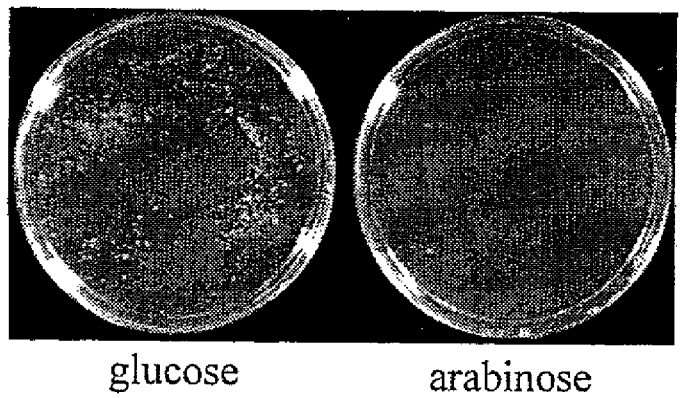
FIG. 17 depicts the lack of growth observed on arabinose for the supE-containing strains while only a small background of growth was observed on arabinose for the sup123-containing strains.

To test the ability of our in vivo selection approach to generate mutant Flp enzymes capable of recognizing and recombining new DNA sequences, a mutant FRT target site (FRTmut) was created in which all four critical bases implicated in the structural and biochemical characterization of the Flp-FRT complex were mutated (FIG. 13). These four changes were reflected in both half sites of the mutant FRT (introducing eight mutations) to allow each evolved Flp monomer to recognize the altered half site specifically. Finally, a ninth mutation was introduced into FRT, changing the T:A of base pair 6 to an A:T base pair, to transform the two half sites into a true inverted repeat. It has been previously shown that mutations at base pair 6 do not significantly affect recombination efficiency (B. J. Andrews, et al. *Cell* 1985, 40, 795-803). A total of nine mutations were thus introduced into pFRT+ to form our first target plasmid, designated pFRTmut+. Using DNA shuffling (W. P. C. Stemmer. *Nature* 1994, 370, 389-91; W. P. Stemmer. *Proc. Natl. Acad. Sci. USA* 1994, 91, 10747-51) we have generated large libraries of mutant Flp recombinase genes (FIG. 14) and transformed these libraries into *E. coli* cells harboring pFRTmut+. The quality of the first round library was verified by characterizing randomly chosen members before selection and estimate its diversity to be approximately 2×10$^7$ mutant recombinases. Cells harboring pFRTmut+ and transformed with wild-type pFlp survive on 10 μg/mL ampicillin at a background rate of 11n 2×10$^5$ transformants plated. When the first library of mutant Flp recombinase enzymes was transformed into cells harboring pFRTmut+, survival on 10 μg/mL ampicillin at a significantly higher rate of approximately 1 in 10$^4$ transformants was observed. The in vivo recombination of pFRTmut+ has been confirmed in at least two surviving colonies by restriction digestion of plasmid DNA isolated from round one survivors demonstrating the loss of a 2,500 base pair DNA fragment (FIG. 15). Starting from the 14,000 round one survivors, we performed a second round of DNA shuffling and selection. Survivors were obtained from the second round of selection at a rate of approximately 1 in 10$^3$ transformants, consistent with the possibility that mutations responsible for desired changes in recombinase specificity are emerging and being enriched in the selection. Efforts are in progress to purify and assay recombinases from the first two selection rounds, as well as to conduct subsequent rounds of DNA shuffling and selection.

Example 3

An in vivo Selection System for Intein Activity

Several of the concepts described above have been applied to efforts to develop an in vivo selection for intein activity. Among the growing collection of inteins studied, the *M. tuberculosis* RecA intein is particularly attractive because of its small size, ability to splice efficiently, and well-characterized in vitro and in vivo properties (K. V. Mills et al. *J. Biol. Chem.* 2001, 276, 10832-8; K. Shingledecker, et al. *Arch. BioChem. Biophys.* 2000, 375, 138-44; B. M. Lew, et al. *J. Biol. Chem.* 1998, 273, 15887-90; K. V. Mills, et al. *Proc. Natl. Acad. Sci. USA* 1998, 95, 3543-8). We hypothesized that protein splicing activity could be linked to cell survival by disrupting an essential gene with the RecA intein. Only cells harboring active inteins would be able to generate the essential protein in the active form required for cell viability. For the reasons discussed above, the use of an antibiotic resistance gene was chosen, rather than a metabolic gene, as the basis for this positive selection. The kanamycin resistance protein aminoglycoside 3'-phosphotransferase (kan$^r$) has previously been shown to tolerate protein splicing by the RecA intein (S. Daugelat et al. *Protein Sci.* 1999, 8, 644-53). While the structure of the kan$^r$ protein has not yet been solved, homology modeling with the structure of the related protein aminoglycoside kinase (W. C. Hon, et al. *Cell* 1997, 89, 887-95) was used to examine several candidate sites in the kan$^r$ protein that would likely tolerate the three amino acid "scar" (Ala-Cys-Arg) left behind by translating the restriction enzyme sites used for cloning our future intein libraries and by the Cys residue required for protein splicing. Insertion of the intein following residue 119 in kan$^r$ offered an excellent combination of high predicted B-factors and distance from the active site, and did not require drastic changes in side chain polarity to accommodate the splice junction scar. Promisingly, this location is adjacent to a site in kan$^r$ chosen previously for intein insertion (S. Daugelat et al. *Protein Sci.* 1999, 8, 644-53), although a different cloning scheme and therefore different scar residues were used in that work.

Figure 22:
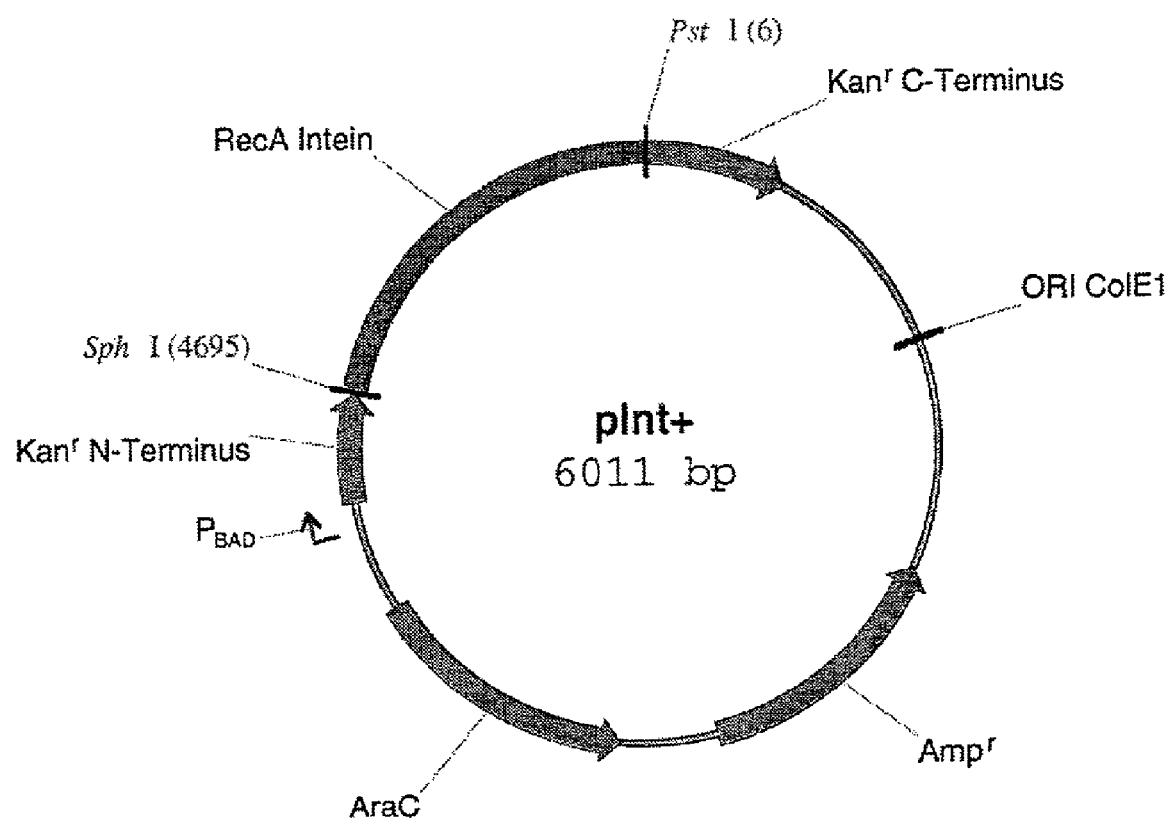
FIG. 22 depicts the construction of the positive selection plasmid (pInt+) in which the kanr gene was disrupted with the RecA intein after position 119 and placed under the transcriptional control of the $P_{BAD}$ promoter.
Figure 23:
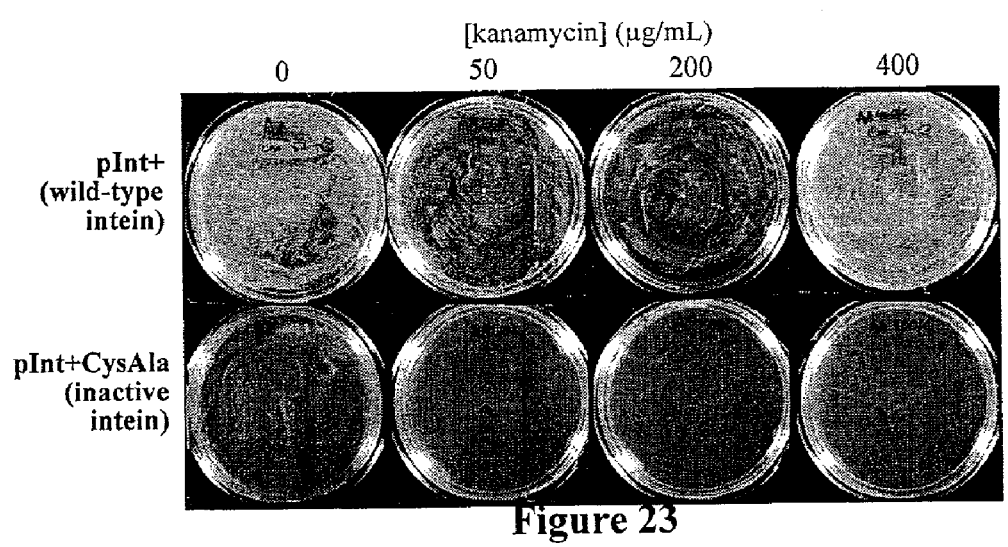
FIG. 23 depicts the mutation of the key catalytic Cys residue at the start of the C-extein to Ala, creating an inactive intein. Cells harboring this nonsplicing version of pInt+, designated pInt+CysAla, were unable to grow in the presence of 50 μg/mL kanamycin.

Using standard site-directed mutagenesis procedures, a control plasmid was generated expressing a mock-spliced kan$^r$ gene containing our Ala-Cys-Arg splicing scar after position 119. Cells harboring this mock-spliced plasmid were able to grow in the presence of 600 µg/mL or more of kanamycin, confirming that the spliced protein can confer high levels of kanamycin resistance. The positive selection plasmid (pInt+) was then constructed in which the kan$^r$ gene was disrupted with the RecA intein after position 119 and placed under the transcriptional control of the $P_{BAD}$ promoter (FIG. 22). *E. coli* cells were transformed with this vector and, following three hours of induction at room temperature to allow protein splicing to take place, were plated on media supplemented with arabinose and a range of kanamycin concentrations. The resulting cells were able to grow at 25° C. in the presence of 400 µg/mL of kanamycin, consistent with protein splicing enabling cell survival in our positive selection (FIG. 23). To verify that the intein activity was responsible for cell survival, the key catalytic Cys residue was mutated at the start of the C-extein to Ala, creating an inactive intein, and repeated our kanamycin titrations. Cells harboring this non-splicing version of pInt+, designated pInt+CysAla, were unable to grow in the presence of 50 µg/mL kanamycin (FIG. 23). As an additional control, the effects of temperature on the ability of the cells to survive were measured in the positive selection. Since protein splicing by the RecA intein out of its natural context is known to be temperature sensitive, it was expected that performing the protein splicing selection at elevated temperatures would decrease the kanamycin resistance of the cells even though the mock-spliced kan$^r$ protein is completely active at 37° C. Indeed, only weak kanamycin resistance was observed at 30° C., and no kanamycin resistance at 37° C., consistent with a linkage between protein splicing and cell survival. Under optimized induction and growth conditions, our signal to background ratio with the wild-type intein was greater than 100,000 to 1, providing a promising basis for intein evolution.

The evolution of conditionally active inteins (such as ligand activated or ligand inactivated inteins) requires a robust negative selection in addition to a positive selection. Ligand activated inteins are evolved by selecting positively for protein splicing in the presence of the small molecule (or library of small molecules) and selecting negatively in the absence of the small molecule. Conversely, ligand inactivated inteins are evolved by selecting negatively in the presence of the small molecule, and selecting positively in its absence.

Efforts have therefore been initiated to couple protein splicing activity with cell death. Several candidate sites for the insertion of the RecA intein into toxic protein barnase have been chosen by applying to the barnase structure (A. M. Buckle, et al. *Biochemistry* 1994, 33, 8878-89) an analysis similar to the one used to examine the kan$^r$ protein for intein insertion sites. Efforts to clone these negative selection vectors, even under glucose repression of barnase-intein expression, were hampered by the extreme toxicity of barnase. As a result, Lys 27 was mutated to Ala in barnase, a change known to lower the RNA hydrolysis activity of the enzyme 100-fold (D. E. Mossakowska, et al. *Biochemistry* 1989, 28, 3843-50) and reconstructed a candidate negative selection vector. In the context of this barnase mutant, the wild-type intein causes cell death, and the inactive Cys to Ala intein mutant survives. A barnase reporter has therefore been generated that can usefully be employed in negative selection assays for identification of allosteric inteins.

Furthermore, it has been demonstrated herein that active inteins can be selected from within a population of inactive inteins using our positive selection construct (the KanR gene interrupted by intein sequence). In particular, the KanR construct containing wild type intein was mixed with an excess ($10^2$, $10^4$, or $10^6$-fold) of the same construct containing inactive intein (Cys to Ala mutant), and used the mixture to transform *E. coli*. After two days of growth in liquid culture in the presence of kanamycin, a 10-fold excess of wild-type intein was isolated, representing an enrichment of at least $10^7$-fold as a result of selection.

Example 4

Development of Negative Selections for Site-Specific Recombinase and Protein Splicing Activities Proteins evolved towards new substrate specificities very often retain much of their wild-type specificity, and occasionally acquire new unselected specificities as well (N. Wymer, et al *Structure* 2001, 9, 1-10; S. Fong, T. D. et al. *Chem. Biol.* 2000, 7, 873-83; A. Iffland, et al. *Biochemistry* 2000, 39, 10790-8; C. Jurgens, et al. *Proc. Natl. Acad. Sci. USA* 2000, 97, 9925-30;T. Lanio, et al. *J. Mol. Biol.* 1998, 283, 59-69; T. Kumamaru, et al. *Nat. Biotechnol.* 1998, 16, 663-6; J. H. Zhang, et al. *Proc. Natl. Acad. Sci. USA* 1997, 94, 4504-9; D. R. Liu, et al. *Proc. Natl. Acad. Sci. USA* 1997, 94, 10092-10097.T. Yano, S. Oue and H. Kagamiyama. Directed evolution of an aspartate aminotransferase with new substrate specificities. *Proc. Natl. Acad. Sci. USA* 1998, 95, 5511-5). The broadening, rather than altering, of substrate specificity in the case of recombinases and homing endonucleases is undesirable for at least two reasons. First, achieving a detailed understanding of how mutations in these enzymes contribute to changes in their DNA recognition is complicated by the broad acceptance of many substrate sequences. A set of evolved mutant recombinases and nucleases ideal for understanding the molecular basis of DNA recognition would each recognize a different substrate with high specificity. Second, homing endonucleases and recombinases with broad substrate tolerances are not appropriate for the manipulation of DNA in vivo because of the possibility that they will cleave or recombine intracellular DNA sequences other than the ones being targeted. Likewise, the molecular evolution of allosterically activated (or inactivated) inteins clearly requires a negative selection to remove the large fraction of intein mutants that will be equally active in the presence or the absence of the small molecule ligand.

Figure 24:
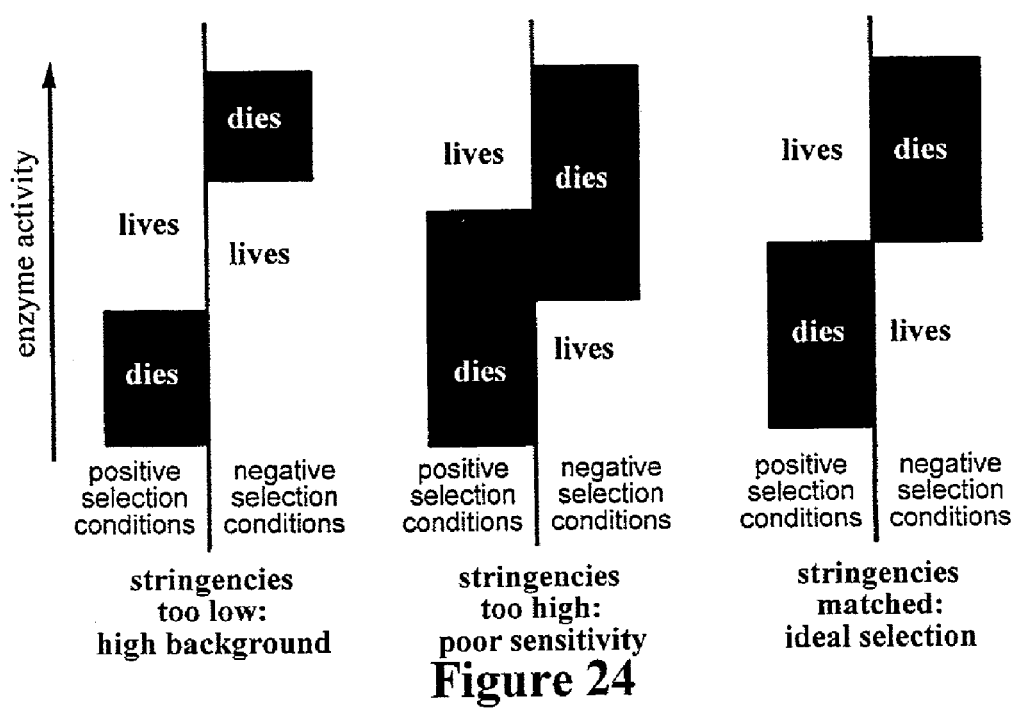
FIG. 24 depicts a plot of enzyme activity versus stringency level. The ideal in vivo negative selection should be matched in stringency with its counterpart positive selection.

An ideal in vivo negative selection for our goals must be matched in stringency with its counterpart positive selection (FIG. 24). If the negative selection is not sufficiently stringent, enzymes with some undesired activity may survive both selections, leading to a high background. On the other hand, if the negative selection is too stringent relative to the positive selection, clones with acceptably low levels of undesired activity may not survive, leading to a low (or zero) hit rate and thus poor sensitivity. As a result of these considerations, we propose to use the highly toxic ribonuclease barnase (D. D. Axe, et al. *Proc. Natl. Acad. Sci. USA* 1996, 93, 5590-5594; M. Jucovic et al. *Proc. Natl. Acad. Sci. USA* 1996, 93, 2343-7; A. M. Buckle, et al. *Biochemistry* 1994, 33, 8878-89; S. M. Deyev, et al. *Mol. Gen. Genet.* 1998, 259, 379-82) as the basis for recombinase and intein negative selections. We have considerable experience with the use of this enzyme in negative selections (D. R. Liu et al. *Proc. Natl. Acad. Sci. USA* 1999, 96, 4780-4785) and have modulated its toxicity over several orders of magnitude by (i) introducing one, two, or three amber nonsense codons at nonessential residues in barnase, (ii) by co-expressing a variety of amber suppressor tRNAs with varying abilities to suppress amber nonsense codons (D. R. Liu, et al. *Chemistry and Biology* 1997, 4, 685-691) and (iii) mutating residues such as Lys 27, Asp 54, or Glu 73 known to play important catalytic roles in barnase to decrease its RNA hydrolysis activity 10- to 10,000-fold (D. E. Mossakowska, et al. *Biochemistry* 1989, 28, 3843-50). The ability to modulate the activity of barnase, and therefore the stringency of a barnase-based in vivo selection, makes this system ideal for developing recombinase and intein negative selections.

Figure 25:
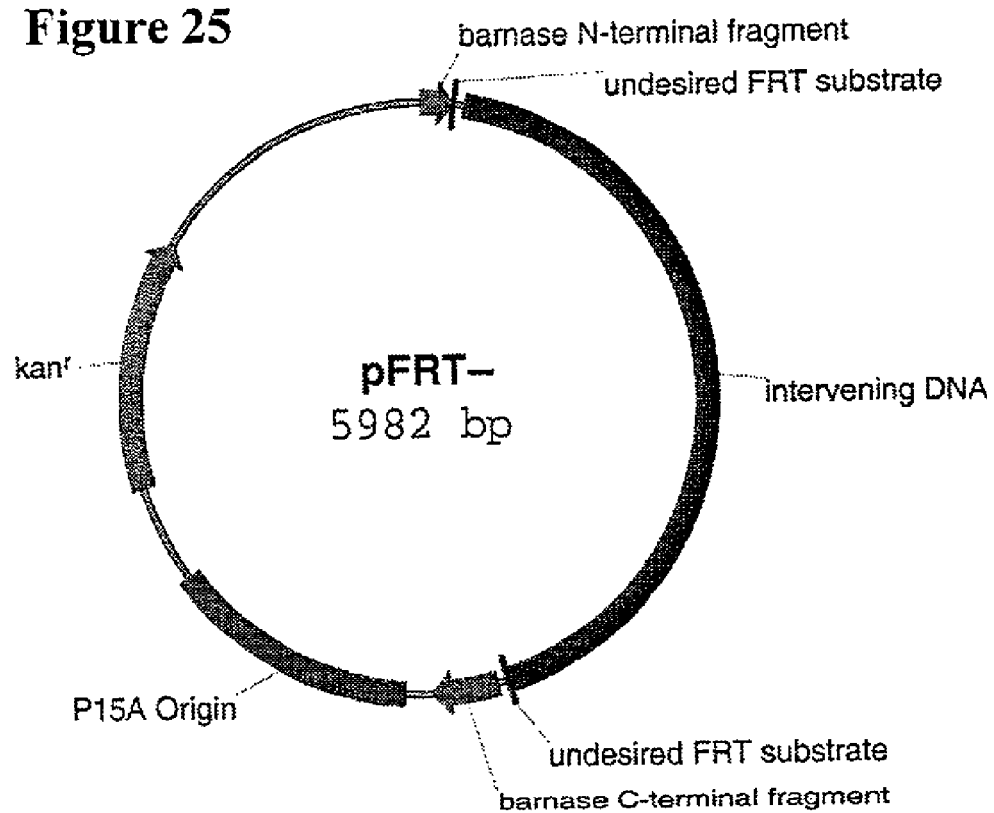
FIG. 25 depicts the construction of variants of the pFRT+ plasmids, designated pFRT, in which the disrupted β-lactamase gene is replaced by a disrupted barnase variant containing one more nonsense or missense mutations to modulate its toxicity.

To develop a negative selection for site-specific recombinase activity, we propose to construct variants of the pFRT+ plasmids, designated pFRT− (FIG. 25), in which the disrupted n-lactamase gene is replaced by a disrupted barnase variant containing one or more nonsense or missense mutations to modulate its toxicity. From our analysis of the high resolution crystal structure of barnase (A. M. Buckle, et al. *Biochemistry* 1994, 33, 8878-89) we propose that the 12-residue recombination footprint left behind by the action of Flp may be accommodated after residue Val 37, which lies in a disordered loop distal from the barnase active site. This region of barnase is also known to accommodate large hydrophilic insertions without significantly reducing barnase activity (S. M. Deyev, et al. *Mol. Gen. Genet.* 1998, 259, 379-82). Competent *E. coli* cells harboring pFRT− will be transformed with wild-type pFlp and the resulting cells plated on media containing chloramphenicol (to maintain the Flp plasmid), kanamycin (to maintain the FRT-barnase plasmid), and arabinose (to induce barnase expression). The resulting cells should recombine the pFRT− plasmid into a lethal, uninterrupted barnase expression vector, resulting in cell death. As controls, transforming pFlpY343F expressing the inactive Flp mutant into cells harboring pFRT− should result in no barnase gene recombination, no functional barnase production, and cell survival. Similarly, cells containing the wild-type pFlp and a pFRT− variant containing an FRT mutant that cannot be recombined by Flp should also be viable. The characterization of these controls and of the ability of Flp and FRT mutants with intermediate activities to survive will complete the development of a negative selection linking recombinase activity with cell death. During recombinase library evolution, undesired recombination sites (such as the wild-type FRT sequence) are cloned into pFRT− flanking the barnase insertion. The introduction of pFlp libraries into cells harboring the pFRT− vectors will remove Flp mutants capable of recombining the undesired substrates from the evolving pool of enzymes.

Figure 26:
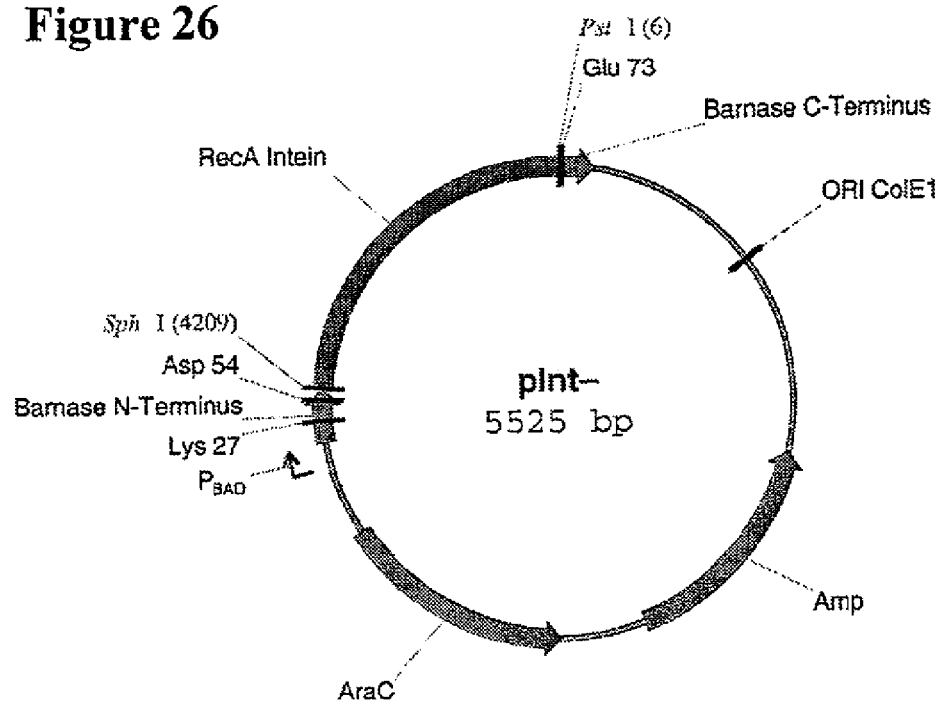
FIG. 26 depicts the replacement of the intein-disrupted kanamycin resistance gene in pInt+ with an intein-disrupted barnase gene to afford pInt−.

As discussed below, a negative selection for intein activity is already under development using similar principles. We have replaced the intein-disrupted kanamycin resistance gene in pInt+ with an intein-disrupted barnase gene to afford pInt− (FIG. 26). Based on an analysis of the sequence and structure of barnase, we hypothesized that insertion of the intein library into the barnase gene after residue Lys 66 would be ideal for our negative selection. Inserting the relatively large RecA intein into this region of the C-terminal domain will likely disrupt the conformation of nearby catalytic residues Glu 73 and His 102, suggesting that the unspliced protein will not possess barnase activity and therefore not be lethal to cells. The spliced protein differs from native barnase in this region only in that the wild-type residues Ser 67, Gly 68, and Arg 69 are replaced by the splice "scar" residues Ala 67, Cys 68, and Ser 69; we predict that the resulting barnase will possess significant RNase activity. To test these hypotheses, we will characterize the ability of the wild-type RecA intein, cloned into pInt− to induce cell death. As a control, we will demonstrate that the inactive C-terminal Cys to Ala mutant of the RecA intein, when cloned into pInt−, is not lethal to cells. If the basal level of barnase expression in either the recombinase or the intein negative selection proves to be lethal, its toxicity will be decreased by introducing additional mutations into the barnase gene, or by introducing amber nonsense codons at positions Gln 2, Asp 44, and/or Gly 65 together with amber suppressor tRNAs (D. R. Liu et al. *Proc. Natl. Acad. Sci. USA* 1999, 96, 4780-4785; D. R. Liu, et al. *Chemistry and Biology* 1997, 4, 685-691). Mutation of Lys 27 to Ala is known to reduce barnase activity by 100-fold, while the Asp 54 Ala mutant exhibits 10-fold lower activity (D. E. Mossakowska, et al. *Biochemistry* 1989, 28, 3843-50). Given the extreme toxicity of unmutated barnase in our hands and those of other researchers, it is very likely that at least one of these variants of barnase will be sufficiently toxic to serve in these negative selections.

Example 5

Development of a Negative Selection for Homing Endonuclease Activity

Figure 27:
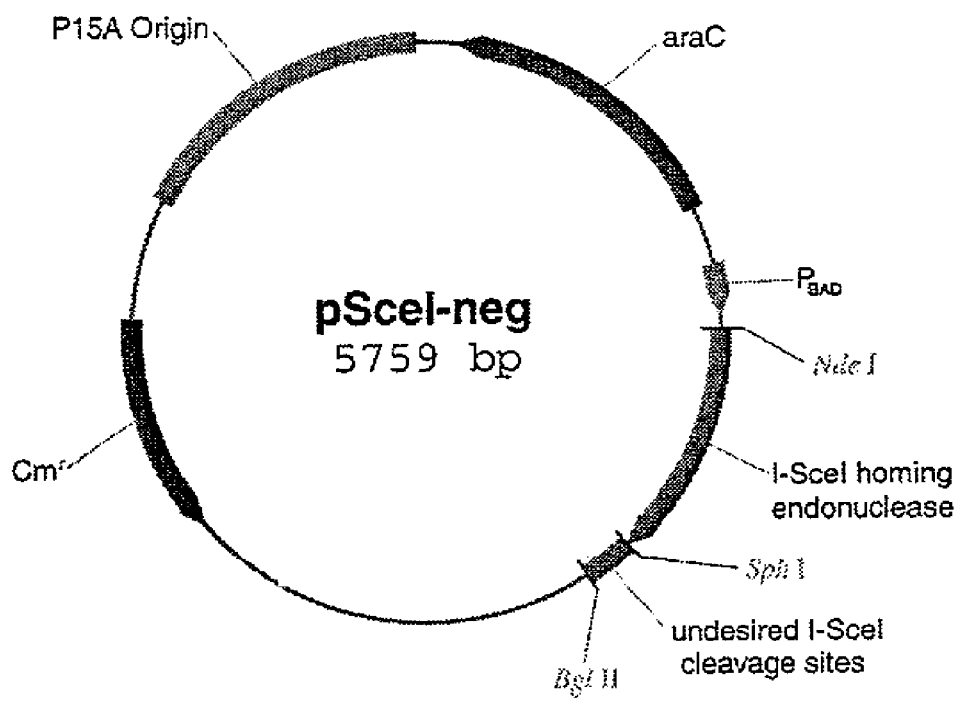
FIG. 27 depicts the cloning of one or more undesired cleavage sites into the homing endonuclease vector to afford pScel-neg, pScaI-neg, or pPIScel-neg.

Evolving homing endonucleases with highly specific and altered cleavage specificities will require the development of a negative selection linking homing endonuclease activity to cell death. To achieve this link, one or more copies of undesired cleavage sites are simply cloned into the homing endonuclease expression vector to afford pSceI-neg, pScaI-neg, or pPISceI-neg (FIG. 27). When a library of homing endonucleases is cloned into these vectors, those nucleases capable of cleaving the undesired sites destroy their own plasmids, removing themselves from the pool of evolving nuclease genes. Because the cleavage of any of the undesired sites will linearize the plasmid encoding that nuclease, the simultaneous selection against the cleavage of several undesired substrates can be accomplished by cloning all of the undesired substrates into the nuclease expression vector. The stringency of this negative selection can be modulated by increasing or decreasing the number of copies of undesired cleavage sites in the vector. To validate this negative selection, the wild-type cleavage sites of I-SceI, I-ScaI, or PI-SceI will be used as the "undesired" cleavage sites, and the corresponding wild-type nuclease will be expressed from the appropriate plasmid. Cells should not survive under these conditions. As controls, the expression of the inactive catalytic Asp to Ser mutants should allow cells to survive in this negative selection. Similarly, the combination of wild-type nucleases and mutant sites known not to be cleaved by the wild-type enzymes (such as those described above) should also be viable. The phenotypic characterization of partially active mutants and cleavage substrates in these negative selections will provide a robust system for removing homing endonuclease with undesired cleavage specificities from the evolving pool of enzymes.

Example 6

Use of the in vivo Positive and Negative Selections to Evolve Recombinases, Nucleases and Inteins A) Evolving Flp Recombinases with Altered DNA Specificities The ongoing positive selections towards generating mutant Flp recombinases capable of recombining the FRT variant are conducted as shown in FIG. 13. While initial selection phenotypes and even in vivo assays of mutant Flp enzymes surviving the selection are already promising (see above), evolution towards this multiply mutated target may prove to be too difficult. In this case, intermediate targets are constructed harboring only one or two mutations per half site. The final two half site mutations could be reintroduced into the target once several rounds of evolution have generated recombinases that efficiently process substrates containing the first two mutations. Later rounds of positive selection will be conducted in the presence of increasing concentrations of ampicillin to raise the stringency of the selection and favor more highly active recombinases. Once positive selection phenotypes and in vivo recombination genotypes are confirmed as described earlier, clones of interest from each round of evolution are subjected to DNA sequence analysis and are subcloned into a hexahistidine-tagged (E. Hochuli, et al. *J. Chromatography* 1987, 411, 177-184) (or GST-tagged) expression vector for facile protein purification. The DNA specificity and activity of purified evolved recombinases will be evaluated using the methods proposed in the section below. Based on the results of previous protein evolution efforts (N. Wymer, et al. *Structure* 2001, 9, 1-10; S. Fong, et al. *Chem. Biol.* 2000, 7, 873-83; A. Iffland, et al. *Biochemistry* 2000, 39, 10790-8; C. Jurgens, et al *Proc. Natl. Acad. Sci. USA* 2000, 97, 9925-30; T. Lanio, et al. *J. Mol. Biol.* 1998, 283, 59-69; T. Kumamaru, et al. *Nat. Biotechnol.* 1998, 16, 663-6; J. H. Zhang, et al. *Proc. Natl. Acad. Sci. USA* 1997, 94, 4504-9; D. R. Liu, et al. *Proc. Natl. Acad. Sci. USA* 1997, 94, 10092-10097; T. Yano, et al. *Proc. Natl. Acad. Sci. USA* 1998, 95, 5511-5) multiple rounds of positive selection will likely afford mutant recombinase enzymes with broadened, rather than altered specificities. To evolve recombinases with truly altered specificities rivaling or exceeding the specificity of the wild-type enzyme will likely require conducting negative selections to remove those enzymes retained or acquired undesired specificity. These positive and negative selections are designed to work together efficiently. Recombinases emerging from a positive selection are amplified by PCR, diversified using DNA shuffling, and cloned directly into the pFRT- plasmid containing the wild-type (or other undesired) FRT site. Those evolved recombinases with a decreased ability to recombine the wild-type FRT site will enjoy a growth advantage in the negative selection because they produce less functional barnase protein. In later rounds, the stringency of the negative selection will be increased by using more active variants of barnase or by decreasing the length of time preceding barnase induction. Multiple rounds of both positive and negative selection with DNA shuffling between rounds should afford evolved recombinases with the ability to recombine the target sequence efficiently and a decreased or negligible ability to recombine the wild-type FRT sequence.

B) Applications and Future Studies of Recombinase Evolution

Figure 28:
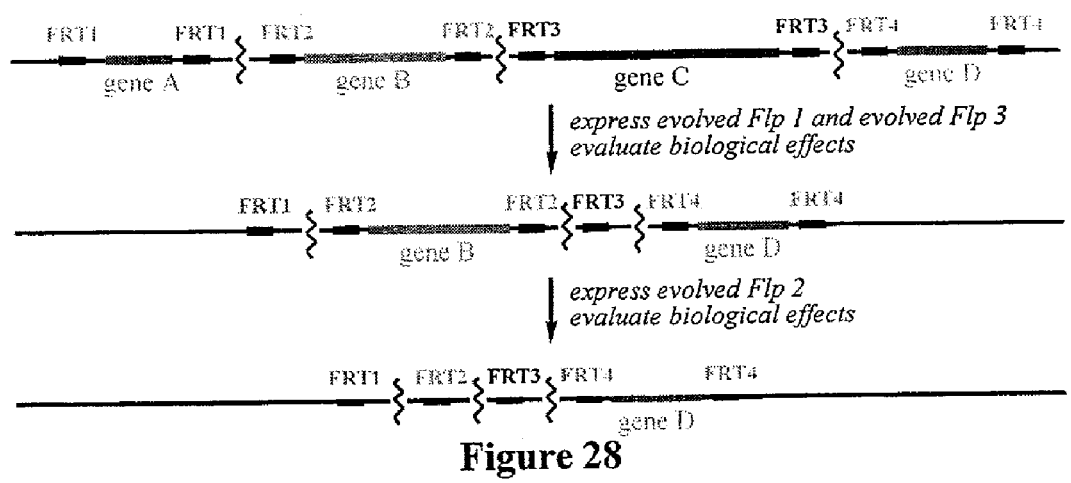
FIG. 28 depicts the evolution in parallel several additional orthogonal mutant Flp-FRT pairs that demonstrate exclusive recombination specificity. These pairs may be used to individually introduce ("knock in") or excise ("knock out") genes of interest participating in complex gene networks such as those involved in development, signal transduction, or apoptosis by flanking each gene of interest with a different FRT variant.

The evolution of mutant Flp enzymes capable of efficiently and specifically recombining new DNA substrates can also be extended in two additional directions. First, several additional orthogonal mutant Flp-FRT pairs that demonstrate exclusive recombination specificity are evolved in parallel. These pairs may be used to individually introduce ("knock in") or excise ("knock out") genes of interest participating in complex gene networks such as those involved in development, signal transduction, or apoptosis by flanking each gene of interest with a different FRT variant (FIG. 28). Expression of any combination of evolved Flp enzymes would induce the recombination of the corresponding combination of genes. Indeed, the value of having independent control over just two genes by using Cre-loxP and Flp-FRT in the same cell was demonstrated recently by Dymecki and coworkers (F. W. Farley, et al. *Genesis* 2000, 28, 106-10). Exerting independent conditional control over a target gene and a selection marker allowed these researchers to cleanly introduce a target gene and then excise the selection marker (F. W. Farley, et al. *Genesis* 2000, 28, 106-10). Expanding the repertoire of orthogonal recombinases with evolved Flp-FRT pairs would allow this independent control over more complex systems involving more than two genes. As a second extension ability of pairs of evolved Flp enzymes to recombine arbitrary, nonpalindromic DNA sequences are evaluated. Two evolved Flp mutants, each of which recombines a different mutant FRT site, are rcoexpressed, and their combined ability to recombine a non-palindromic mutant FRT site made of the two different half sites will be evaluated in vitro and in vivo by the assays described above. Removing the inverted half site requirement from site-specific recombinases would significantly increase the range of DNA substrates accessible by these enzymes, and may enable evolved recombinases to access sites naturally present in the genomes of organisms of interest.

C) Evolving Homing Endonucleases with Altered DNA Specificities

Figure 18:
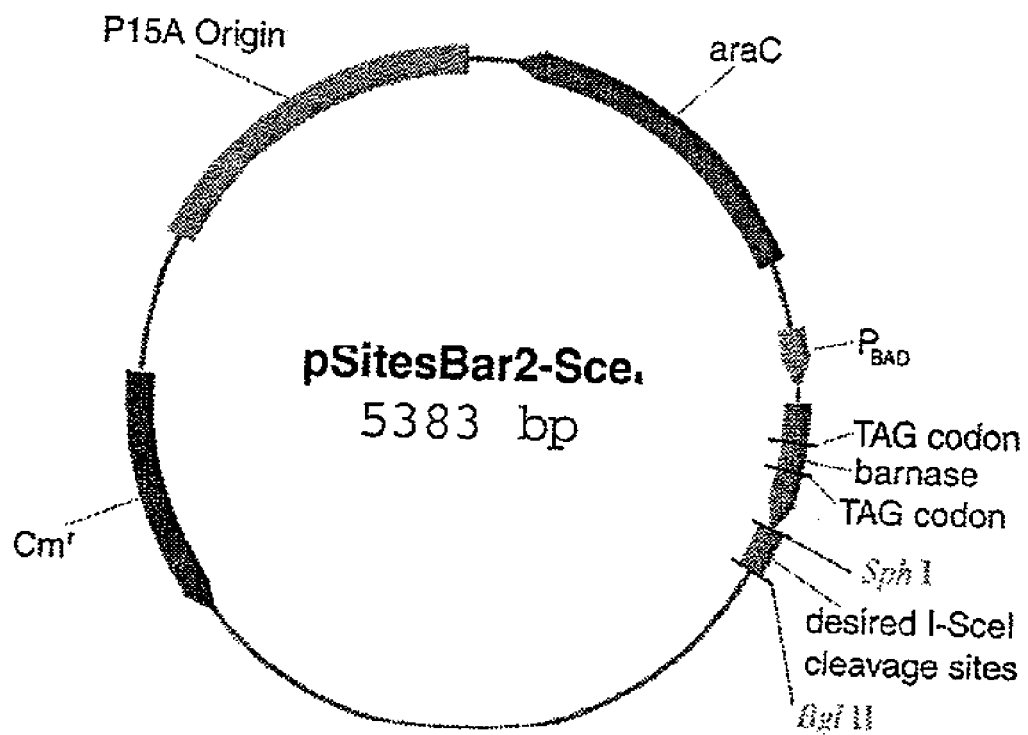
FIG. 18 depicts the linking of homing endonuclease activity and specificity to the alleviation of toxicity and depicts the generation of short DNA cassettes containing the wild-type cleavage sequences of I-Scel, PI-Scel, or I-ScaI. One to seven copies of each recognition sequence were ligated into pBarAm2 to afford pSitesBar2-Scel, pSitesBar2-PIScel, and pSitesBar2-ScaI.
Figure 19:
FIG. 19 depicts that the expression of a homing endonuclease capable of cleaving the pSitesBar2 plasmid was able to confer high levels of survival on arabinose and ampicillin.
Figure 20:
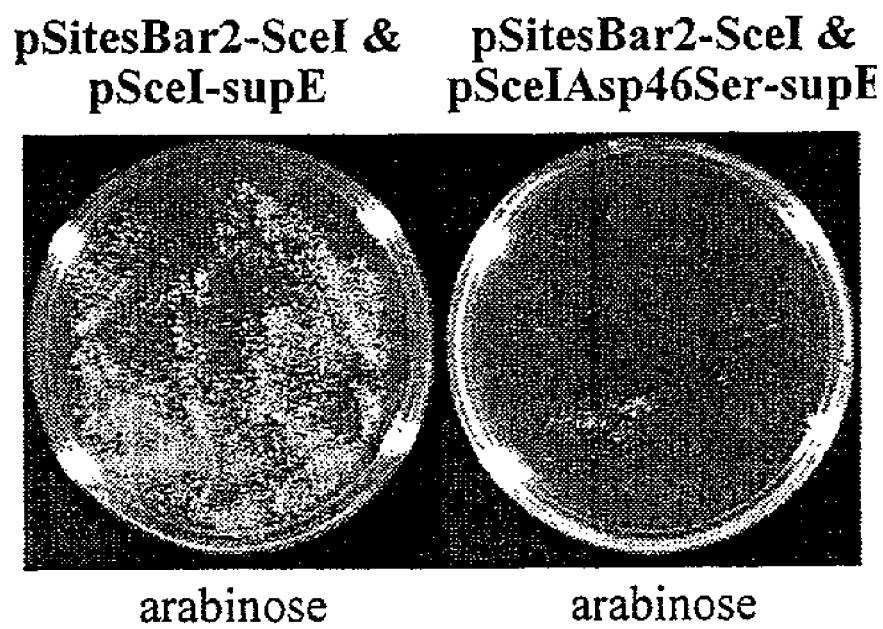
FIG. 20 depicts the mutation of one critical active site Asp residue in each homing endonuclease to Ser (Asp46 in I-Scel, Asp 90 in I-ScaI, and Asp 218 in PI-Scel). The resulting mutant endonuclease expression plasmids were largely unable to produce viable colonies when introduced into cells harboring a corresponding matched pSitesBar2 plasmid.

In a similar manner, positive selections for I-SceI and I-ScaI homing endonucleases capable of cleaving the two target sites are conducted as shown in FIG. 21. The stringency during rounds of positive selection will be gradually increased by using pSitesBar2 vectors (FIG. 18) with fewer copies of the target sites, and by decreasing the duration of homing endonuclease expression prior to barnase induction. While evolving mutant I-SceI enzymes capable of cleaving the singly mutated target site can likely be achieved using our positive selection, mutant I-ScaI enzymes that cleave the triply mutated I-ScaI site matching the HIV-1 glycoprotein 120 sequence may not be accessible at a detectable frequency (greater than 1 in $10^8$) in a first round library. In this case, I-ScaI evolution efforts are focused on the stepwise evolution of altered specificity using the singly and doubly mutated intermediates already constructed. Once positive selection phenotypes are promising, the purification and characterization of mutant homing endonucleases are conducted and negative selections are initiated to remove those nucleases that cleave the wild-type I-SceI or I-ScaI substrates. The stringency of the negative selection are increased, if needed, by increasing the number of copies of undesired cleavage sites in the homing endonuclease vector or in the pSitesKan vector. The combination of positive and negative selections should evolve homing endonucleases capable of efficiently and specifically cleaving our new target sequences. If our I-ScaI evolution efforts are successful, the ability of an evolved I-ScaI nuclease to inhibit the propagation of HIV-1 in human T-cell lines by site-specific cleavage of the gp120 gene can be evaluated.

Positive and negative selections for homing endonuclease specificity also raise the possibility of evolving homing endonucleases with longer than normal recognition sequences, in addition to ones that recognize an altered pattern of DNA bases. To homing endonucleases with extended recognition specificity, the canonical sites cloned into the positive and negative selection vectors are identical, while the DNA bases flanking the canonical sites differ in the positive and negative selections (FIG. 29). To allow nucleases to evolve additional DNA binding determinants, random elongation mutagenesis (T. Matsuura, et al. *Nat. Biotechnol.* 1999, 17, 58-61; R. K. Scopes. *Nat. Biotechnol.* 1999, 17, 21) will be used in which randomized sequences are appended to the N- or C-termini of the nucleases in the library. Cells encoding mutant homing endonucleases that acquire specific interactions with bases outside of the canonical recognition sequence will survive both selections and will be subjected to characterization as described above. Evolving homing endonucleases with extended cleavage specificities represents a novel approach to increasing the selectivity of these enzymes and would provide insights into the mechanisms by which new base-specific contacts can evolve.

D) Developing a High Throughput Method for Profiling the DNA Specificity of Evolved Recombinases and Homing Endonucleases Evaluating the specificity of evolved recombinases and homing endonucleases is central to gaining insights into the role of specific residues in altering the DNA recognition abilities of these enzymes. The specificity of mutant recombinases and nucleases can be evaluated in two ways. First, double-stranded DNA sequences of the wild-type and target FRT, I-SceI, and I-ScaI sites will be generated by PCR or by annealing synthetic oligonucleotides, incubated with purified evolved recombinases or nucleases at varying DNA concentrations, and analyzed over several time points by agarose or polyacrylamide gel electrophoresis. While capable of revealing the $k_{cat}$ and $K_m$ of evolved recombinases and nucleases towards individual DNA substrates, this traditional assay approach is labor intensive and not well-suited to the comprehensive characterization of an evolved enzyme's substrate specificity.

Figure 30:
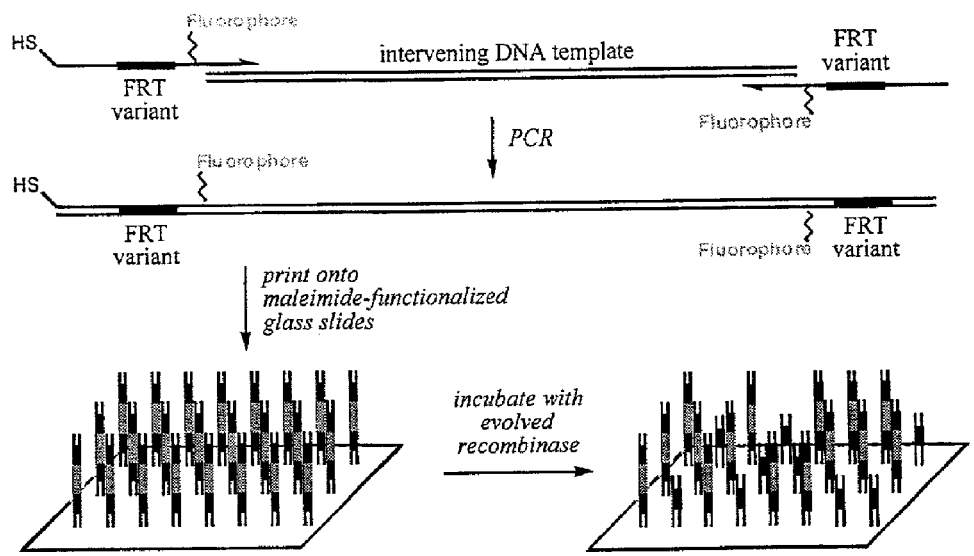
FIG. 30 depicts a general scheme for recombinase specificity profiling in which arrays of spatially separated double-stranded DNA sequences are generated in which each location of the array contains a different potential recombinase substrate.

To address these limitations, a DNA array-based method of rapidly and more comprehensively evaluating the substrate specificity of recombinases and homing endonucleases is developed. In the case of recombinase specificity profiling (FIG. 30), arrays of spatially separated double-stranded DNA sequences are generated in which each location of the array contains a different potential recombinase substrate. While a method for generating arrays of short double-stranded DNA oligonucleotides using photolithography and solid-phase synthesis has been reported (M. L. Bulyk, et al. *Nat. Biotechnol.* 1999, 17, 573-7) the length of recombinase substrates required to form a circular intermediate and the high cost of custom-made lithographic masks for light-directed oligonucleotide synthesis (R. J. Lipshutz, et al. *Nat. Genet.* 1999, 21, 20-4) preclude using this method to characterize evolved recombinases. Instead, we propose to construct potential recombinase substrates in PCR reactions using two synthetic DNA primers. Each primer contains (i) a short 5' leader sequence, (ii) the FRT site variant (34 base pairs), and (iii) a fluorescein-dT (Glen Research) followed by a template annealing region (18 base pairs). The template of the PCR reaction is a double-stranded plasmid DNA fragment several hundred base pairs in length containing the primer binding sequences at its ends. PCR amplification generates a double-stranded DNA molecule containing two copies of the predefined FRT variant flanking a fluorescently labeled intervening region (FIG. 30). Each PCR product is then be printed onto a polylysine-functionalized glass surface at a specific location to generate the fluorescently labeled Flp substrate array containing many potential recombination sites. The incubation of wild-type Flp with a control array containing both wild-type and mutant FRT sites will be used to optimize the printing methods, oligonucleotide density, and incubation conditions for efficient Flp-catalyzed recombination of oligonucleotides attached to the array. For example, if the polylysine-bound DNA proves to be inaccessible to the recombinase, 5'-amino- or 5'-thiol-terminated PCR products can instead be attached monovalently to aldehyde (G. MacBeath et al. *Science* 2000, 289, 1760-3) or maleimide linkers bound to glass, respectively. Recombination will cause the excision of the fluorophore, leading to a decrease in the fluorescence intensity of that spot. Comparing the fluorescence intensities of each location of the array before and after incubation with the wild-type or an evolved Flp enzyme can reveal the DNA specificity of the recombinase towards hundreds of potential substrates simultaneously.

Figure 31:
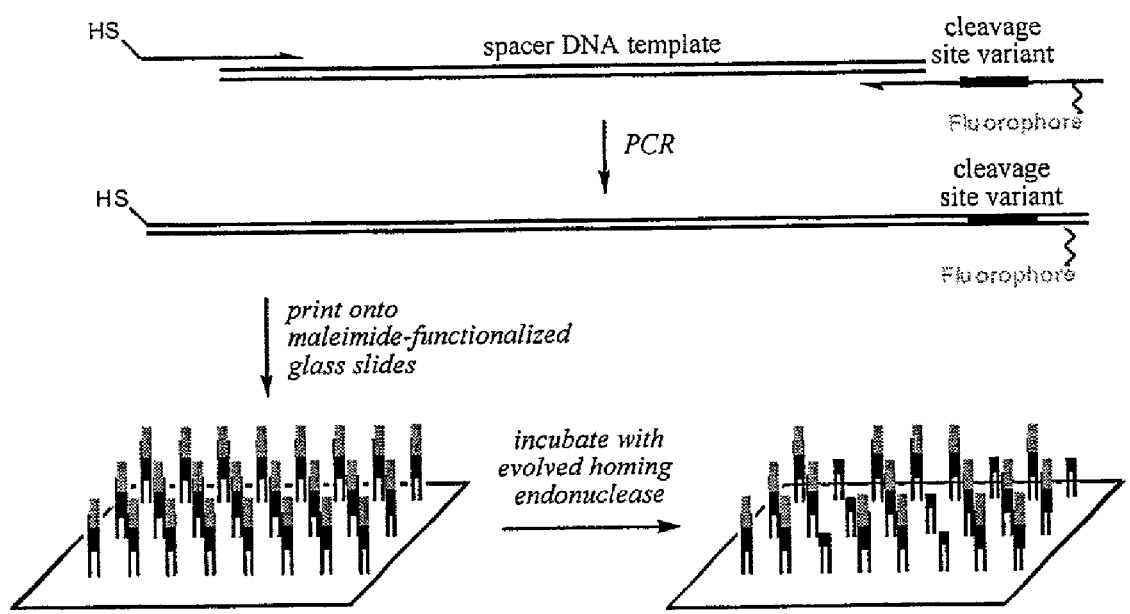
FIG. 31 depicts a similar general scheme for profiling the DNA specificities of evolved homing endonucleases.

A similar method is used for comprehensively profiling the DNA specificities of evolved homing endonucleases (FIG. 31). In this case the potential nuclease substrates are generated by PCR from two synthetic primers, one of which contains a 5' fluorophore and the cleavage site variant, and one of which is 5'-amino or 5'-thiol terminated. The double stranded PCR products are each monovalently attached to aldehyde or maleimide glass slides at a specific location, and the resulting arrays are incubated with a wild-type or evolved homing endonuclease. In this scheme, cleavage activity can be visualized as a decrease of fluorescence over time. The ability of each evolved homing endonuclease to cleave hundreds of potential substrates can be rapidly evaluated in this scheme. The equipment and expertise needed to generate and analyze these arrays is readily available at Harvard's Institute for Chemistry and Cell Biology (ICCB) and at Harvard's Center for Genomics Research (CGR), two institutes closely affiliated with the Department of Chemistry and Chemical Biology. The methods for profiling the DNA specificity of recombinases and homing endonucleases developed in this work may find applications in characterizing other sequence-specific macromolecules and small molecules that manipulate the covalent structure of DNA.

E) Evaluating the Determinants of DNA Specificity in Site-Specific Recombinases and Homing Endonucleases The specificities of recombinase enzymes evolved through iterated rounds of positive and negative selection will provide a wealth of data characterizing the determinants of DNA specificity in Flp recombinase. Careful analysis and follow up studies, often not emphasized in protein evolution efforts, are essential to gaining real insights into the nature of DNA recognition by these enzymes. Many of the nonsilent mutations introduced into the recombinase and nuclease libraries will not affect DNA specificity but are inherited because these mutations may not significantly decrease the ability of enzymes to recognize the target substrate. To eliminate these mutations, a "backcrossing" round of DNA shuffling (W. P. C. Stemmer. Nature 1994, 370, 389-91; H. Zhao et al. *Proc. Natl. Acad. Sci. USA* 1997, 94, 7997-8000) can be performed in which a small amount of recombinase or nuclease library DNA is shuffled with an excess of wild-type gene fragments and subjected to high stringency selection. Because the presence of several molar equivalents of wild-type DNA statistically favors reversion back to the wild-type residue, only those mutations that significantly contribute to the new specificity of the evolved enzymes are retained. In several previous reports, the removal of nonessential mutations collectively increases the evolved activity of the protein significantly (A. Crameri, et al. *Nat. Biotechnol.* 1996, 14, 315-9; W. P. C. Stemmer. *Nature* 1994, 370, 389-91).

Once the nonessential mutations from evolved recombinase and homing endonuclease enzymes have been removed, the mutations responsible for altered specificity can be revealed by automated DNA sequencing of the encoding plasmids. The relatively small size (~1 kB) of the recombinase and homing endonuclease genes allows dozens, if not hundreds, of evolved recombinase and nucleases sequences to be revealed without great expense. Mutations revealed in this fashion will be correlated statistically with the altered DNA specificities of the evolved enzymes and classified as follows:

(i) The importance of mutations that were acquired during positive selection and that correlate highly with recognition of the target substrates will be tested by introducing the mutations, individually and in combinations, into the wild-type recombinase or homing endonuclease gene using site-directed mutagenesis. The specific role of mutations that are verified to contribute to altered specificity by selection phenotype or by in vitro assay will then be interpreted in light of the structural or previous biochemical characterization of Flp, I-SceI, I-ScaI, or PI-SceI.

(ii) Mutations that are found to increase consistently in frequency during the negative selection and which correlate with the loss of wild-type substrate recognition will also be verified using site-directed mutagenesis and their role as determinants against wild-type substrate recognition interpreted in light of existing structural and biochemical data.

(iii) Those mutations introduced during the positive selection but lost during the negative selection may play a role in increasing the nonspecific association of the recombinase or nuclease enzymes with DNA. To test this hypothesis, these mutations will be introduced into wild-type or mutant recombinases and their effects on the comprehensive DNA specificity of the resulting enzymes will be evaluated using the DNA array method described above.

F) Evolving Allosteric Inteins: The development of robust positive and negative selections enables the evolution of conditionally active enzymes by selecting positively under one set of conditions, and negatively under a different set of conditions. When the difference between these two conditions is the presence or absence of a small molecule, proteins that are activated or inactivated by the small molecule emerge from both selections. Inteins are a particularly attractive target for this because a ligand-activated or ligand-inactivated intein may be used to control virtually any protein's activity by disrupting the protein with the evolved allosteric intein. The kinetics of protein splicing (H. Paulus. *Annu. Rev. Biochem.* 2000, 69, 447-96; K. Shingledecker, et al. *Arch. Biochem. Biophys.* 2000, 375, 138-44; Y. Shao et al. *J. Pept Res.* 1997, 50, 193-8) are significantly faster than the rates of transcription followed by translation, and will presumably be improved through rounds of positive selection under kinetic control. Allosterically activated inteins therefore may represent a powerful new approach to rapidly activating proteins of interest with a cell permeable small molecule. Conversely, ligand-inactivated inteins can be used to rapidly stop the production of functional proteins of interest in the presence of a small molecule. In either case, removal of the small molecular effector allows the production of active or inactive protein to be reversible and transient. In addition, modulating the concentration of the small molecule effector may allow the fine titration of intermediate levels of active or inactive protein. The titration of protein expression levels is presently difficult to achieve using gene regulation because of the all- or -none nature of most inducible expression systems D. A. Siegele et al. *Proc. Natl. Acad. Sci. USA* 1997, 94, 8168-72).

Figure 32:
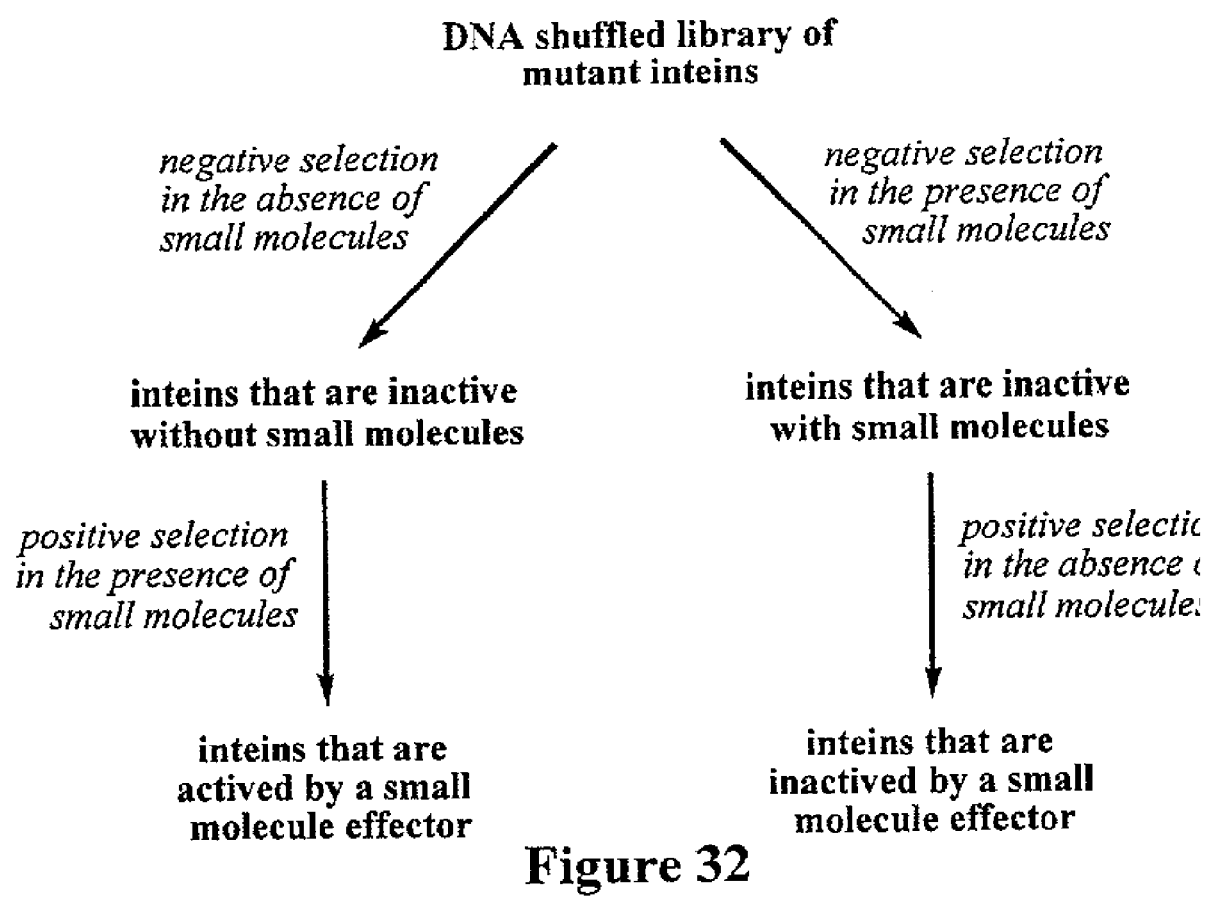
FIG. 32 depicts a general scheme for the evolution of ligand-activated and ligand-inactivated *M. tuberculosis* RecA inteins in two parallel libraries.

We propose to evolve ligand-activated and ligand-inactivated *M. tuberculosis* RecA inteins in two parallel libraries (FIG. 32). In both cases, we will begin our efforts by constructing an initial library of ~$10^9$ intein mutants in which the large hydrophobic residues are mutated at a low frequency to Gly or Ala to create possible allosteric effector binding sites. This library can be generated by synthesizing 39-base oligonucleotides encoding the mutation of each of the nine Trp, eight Tyr, and fourteen Phe codons in the RecA intein to GSC(S=G or C) and adding these oligonucleotides to the fragment reassembly step of the DNA shuffling process (D. R. Liu, et al. *Proc. Natl. Acad. Sci. USA* 1997, 94, 10092-10097). The level of mutagenesis can be controlled by modulating the concentration of mutagenic oligonucleotides relative to the concentration of wild-type intein gene fragments (D. R. Liu, et al. *Proc. Natl. Acad. Sci. USA* 1997, 94, 10092-10097). In the case of evolving ligand-activated inteins, the resulting library of intein mutants will be subjected to the negative selection using the pInt– vector in the absence of small molecule effectors to remove those inteins from the library that are still significantly active. As described earlier, the stringency of this negative selection can be modulated by varying the toxicity of the barnase gene used in the selection. Survivors of this selection will encode mutant inteins with decreased splicing activities. Intein-encoding genes will be amplified by PCR and subcloned into the pInt+ vector. In vivo positive selections will then be carried out in the presence of a small library of potential allosteric effectors (see below). The stringency of each round of positive selection can be modulated by varying the concentration of kanamycin present in the growth media. Surviving clones will be amplified by PCR, diversified with DNA shuffling, and subjected to the next round of selection. Inteins surviving several rounds of negative and positive selection in the absence and presence of small molecule effectors, respectively, may have acquired the ability to be allosterically activated. Conversely, ligand-inactivated inteins will be evolved from the same starting library by conducting the negative selection in the presence of the small molecule effector library, and the positive selection in the absence of the effectors. In this case, survivors of both selections may encode mutant inteins that are inactivated by the binding of a small molecule effector. As the low optimum temperature of the current RecA intein system (25° C.) is not ideal, the temperature of the positive selections will also be gradually increased to 37° C. once desired activities begin to emerge.

Figure 33:
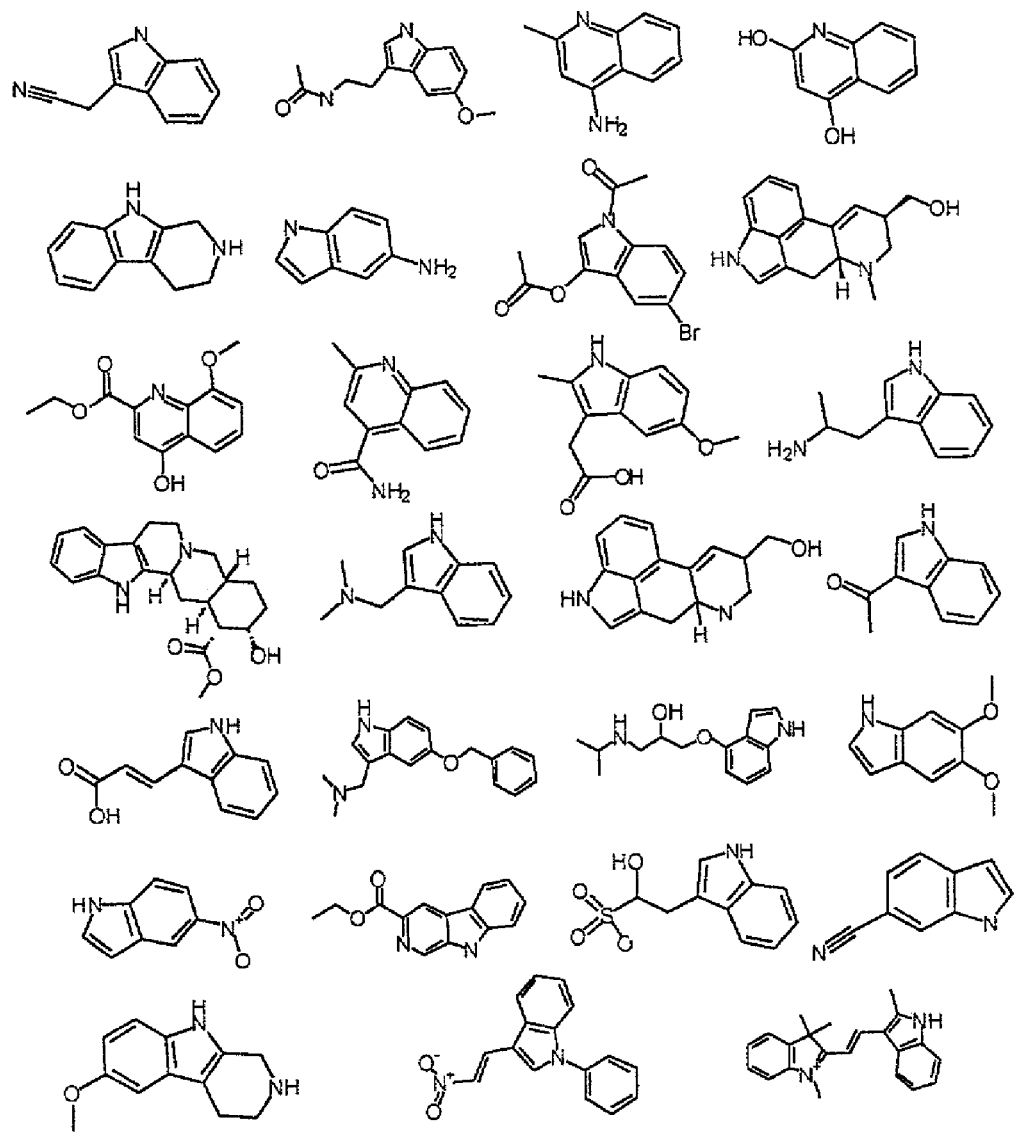
FIG. 33 depicts an exemplary library of potential allosteric effectors.

The candidate small molecule effector library will be constructed of compounds that satisfy the following criteria: (i) the compound must be commercially available or synthesized in one step; (ii) the compound must not be highly charged and must have a molecular weight less than 600 D to maximize the likelihood of cell permeability; (iii) the compound must have at least one aromatic ring to increase the chance of complementing one of the mutations introduced into the intein library; (iv) the compound must have some conformational constraints to decrease the entropic penalty associated with binding the intein; (v) the compound must not be toxic to *E. coli*; and (vi) the compound must be soluble in water at concentrations of 1 mM. Criteria (i), (ii), (iii), and (iv) can be judged by inspection and yield candidates such as the structures should in FIG. 33. We will screen these and other similar compounds for criteria (v) and (vi) using existing methods (D. R. Liu et al. *Proc. Natl. Acad. Sci. USA* 1999, 96, 4780-4785) and assemble several groups of five to ten compounds for simultaneous use in our selections.

G) Characterizing Evolved Allosteric Inteins; Evolved inteins from various rounds of selection will be characterized both in vivo and in vitro. The small molecule specificity of evolved allosteric clones will be deconvoluted by phenotypic screening of each clone of interest in the presence of one of each effector present during the evolution of that clone. Inteins with promising phenotypes will be cloned into pInt+ as hexahistidine-tagged kan$^r$ fusion proteins. Protein splicing in vivo can be assayed by incubating cells in the presence or absence of the small molecule effector, separating crude cell lysate proteins by gel electrophoresis, and visualizing the distinct sizes of the unspliced and spliced proteins by Western blotting using commercially available anti-hexahistidine antibodies (Roche Biosciences). Similarly, evolved intein proteins can be purified from cell lysates using metal affinity chromatography in their inactive forms (i.e., in the absence of the small molecule activator or in the presence of the small molecule inhibitor). The addition of allosteric activator or the removal of the allosteric inhibitor can then initiate protein splicing in vitro and the splicing reaction can be followed by gel electrophoresis.

Similar to the strategy described above to analyze evolved recombinases and homing endonucleases, the mutations responsible for creating an allosteric binding site in the evolved inteins will be analyzed by backcrossing to remove nonessential mutations and correlating remaining mutations with their assayed effects on ligand-activated or ligand-inactivated protein splicing. Site directed mutagenesis will then be used to dissect the role of these critical mutations in the context of the wild-type intein or of inteins containing other critical mutations. The resulting analysis may reveal a common mechanism, or several diverse methods, by which small molecule binding sites that regulate a protein's activity can be evolved.

G) Applications of Allosteric Inteins: Because a single Cys residue is the only absolute extein requirement for RecA-catalyzed protein splicing, the successful evolution of small molecule regulated inteins may allow the rapid, conditional, and reversible control of nearly any protein's activity in vivo. An allosteric intein may also enable the titration of active protein in a cell in response to varying effector dosages. To test this possibility, the quantity of spliced protein generated by *E. coli* cells harboring the allosteric intein in pInt+will be measured in the presence of varying exogenous effector concentrations by quantitative Western and immunoprecipitation analysis using anti-hexahistidine antibodies. In addition, the concentration of kanamycin required to inhibit the growth of cells harboring pInt+ will be quantitated as a function of small molecule concentration to provide a phenotypic in vivo quantitation of dose-dependent intein activity. Unlike traditional transgenic knock out or allelic replacement approaches in which permanent deletions or mutations are introduced into a genome, insertion of an allosteric intein into a gene of interest can be used to study proteins essential for a cell's reproduction and survival. The role of a nonessential protein of interest can be explored by inserting an allosterically activated intein into its sequence and evaluating the effects of varying concentrations of small molecule activator. Conversely, the role of an essential protein may be studied by disrupting the corresponding gene with an allosterically inactivated protein. The production of functional protein in this case can be terminated rapidly by the addition of the allosteric repressor. To decrease the lag time between administration of activator or repressor and the disappearance of non-functional or functional protein in the cell, the N-terminus of the protein of interest can be mutated to an Arg residue to accelerate its degradation (A. Bachmair, et al. *Science* 1986, 234, 179-86; Varshavsky, G. et al. *Biol. Chem.* 2000, 381, 779-89). If the kinetics of evolved intein-catalyzed splicing and target protein degradation are sufficiently fast, it may be possible to "pulse" a protein's activity on the time scale of minutes in a living cell by cycling the concentration of allosteric effector. This level of temporal control of a protein's function is not possible using traditional biochemical methods. Evolved allosteric inteins may therefore become powerful tools for studying time-sensitive biological processes including signal transduction, circadian rhythms, or neuronal communication. In conjunction with gene therapy vectors, allosteric inteins may also allow active proteins including hormones such as insulin to be rapidly generated in mammalian tissues in a dose-dependent response to a small molecule drug.

Example 7

Toxic Gene with Reduced Toxicity

A selection system has been devised similar to one described above utilizing barnase as the toxic gene except that, instead of barnase, we have used the topoisomerase poison CcdB. CcdB is less toxic than barnase, and we have found that we do not need to use a nonsense mutation, but rather can employ the wild type CcdB gene in our assays. In particular, a plasmid has been created containing the CcdB gene under contron of the PBAD promoter, and a homing endonuclease site, exactly analogous to the construct presented in FIG. 34. Experiments indicate that, in the absence of active endonuclease, induction of the toxic gene leads to cell death with a very low background of 1 in 1000.

The invention claimed is:

1. A method for identifying altered inteins that manipulate the covalent structure of macromolecules, wherein the macromolecule is a protein, and wherein the inteins have altered activity or specificity compared to the wild-type intein, the method comprising the steps of:
prov018ing cells comprising a first protein, wherein the first protein without disruption reduces cell growth, wherein the first protein is disrupted by an inserted amino acid sequence, and wherein the inserted amino acid sequence in the first protein comprises a test intein that differs from the wild-type intein;
identifying cells wherein the disruption of the first protein has been removed by the test intein.

2. The method of claim 1, wherein the cells comprise *E. coli* cells.

3. The method of claim 1, wherein the first protein without disruption is toxic.

4. The method of claim 3, wherein the step of providing cells comprises introducing a plasmid encoding the first protein with disruption into the cell.

5. The method of claim 1, wherein the first protein without disruption inhibits the function of a second protein, and wherein the second protein is essential for cell growth.

6. The method of claim 1, wherein the test intein differs by at least one amino acid from the wild type intein.

7. The method of claim 1, wherein the test intein differs in post-translational modification from the wild-type intein.

8. A method for identifying homing endonucleases having altered activity or specificity compared to a wild-type homing endonuclease, the method comprising the steps of:
providing a first plasmid, which plasmid comprises a caged toxic gene, wherein the caged toxic gene is disrupted by an inserted altered homing endonuclease cleavage site of interest, wherein the cleavage site is not recognized by a wild-type homing endonuclease, whereby cells with the first plasmid are not killed by the caged toxic gene before the test homing endonuclease has had an opportunity to act, which caged toxic gene comprises amino acid residues that have been mutated to stop codons, wherein the stop codons are suppressed by a suppressor tRNA;
providing a second plasmid in a cell, which plasmid encodes the test homing endonuclease and a suppressor tRNA that suppresses the stop codons in the caged toxic gene and enables the functional expression of the caged toxic gene;
transforming the first plasmid into the cell with the second plasmid; and
detecting cell survival.

9. The method of claim 8, wherein the caged toxic gene is a mutant form of barnase.

10. The method of claim 9, wherein the mutant form of barnase comprises at least one amber mutation in non-essential residues.

11. The method of claim 9, wherein expression of the barnase gene is controlled by the PBAD promoter.

12. The method of claim 9, wherein the suppressor tRNA is supE.

13. The method of claim 9, wherein the suppressor tRNA is sup123.

14. The method of claim 8, wherein the step of detecting cell survival comprises detecting cell survival growth in the presence of arabinose.

15. A method for identifying altered homing endonucleases that manipulate the covalent structure of macromolecules, wherein the macromolecule is a polynucleotide, and wherein the homing endonucleases have altered activity or specificity compared to the wild-type homing endonuclease, the method comprising the steps of:
providing cells comprising a polynucleotide, wherein the polynucleotide without disruption reduces cell growth, and wherein the polynucleotide is disrupted by an inserted altered homing endonuclease cleavage site of interest, wherein the cleavage site is not recognized by a wild-type homing endonuclease;
transforming the cells with nucleic acids encoding at least one test homing endonuclease that differs from the wild-type homing endonuclease;
identifying transformed cells wherein the disruption of the polynucleotide has been removed by the test homing endonuclease.

16. The method of claim 15, wherein the polynucleotide is DNA.

17. The method of claim 15, wherein the cells comprise *E. Coli* cells.

18. The method of claim 15, wherein the polynucleotide without disruption is toxic.

19. The method of claim 15, wherein the polynucleotide with disruption is on a plasmid.

20. The method of claim 15, wherein the step of identifying transformed cells comprises identifying cells that have decreased cell growth.

21. The method of claim 15, wherein the polynucleotide without disruption inhibits the function of a protein essential for cell growth.

22. The method of claim 21, wherein inhibition of the function of a protein essential for cell growth comprises insertion of a nucleotide sequence in the polynucleotide encoding the protein, such that the inserted nucleotide sequence inhibits the function of the protein essential for cell growth.

23. The method of claim 22, wherein the step of identifying transformed cells comprises identifying cells wherein the test homing endonuclease removes the inserted nucleotide sequence, whereby reduced cell growth indicates removal of the inserted nucleotide sequence by the test homing endonuclease.

24. The method of claim 22, wherein the inserted nucleotide sequence encodes an intervening protein sequence.

25. The method of claim 24, wherein the step of identifying transformed cells comprises identifying cells wherein the test homing endonuclease excises the inserted nucleotide sequence encoding the intervening protein sequence, whereby reduced cell growth indicates removal of the inserted nucleotide sequence by the test homing endonuclease.

26. The method of claim 15, wherein the test homing endonucleases differ by at least one amino acid from the wild type homing endonuclease.

27. The method of claim 15, wherein the test homing endonucleases differ in post-translational modification from the wild-type homing endonuclease.

28. A method for identifying altered inteins that manipulate the covalent structure of macromolecules, wherein the macromolecule is a protein, and wherein the inteins have altered activity or specificity compared to the wild-type intein, the method comprising the steps of:
providing cells comprising a first protein, wherein the first protein without disruption is essential for cell growth, wherein the first protein is disrupted by an inserted amino acid sequence, and wherein the inserted amino acid sequence in the first protein comprises a test intein that differs from the wild-type intein;
identifying cells wherein the disruption of the first protein has been removed by the test intein.

29. The method of claim 28, wherein the cells comprise *E Coli* cells.

30. The method of claim 28, wherein the step of providing cells comprises introducing a plasmid encoding the first protein with disruption into the cell.

31. The method of claim 28, wherein the first protein without disruption inhibits the function of a second protein, and wherein the second protein reduces cell growth.

32. The method of claim 28, wherein the test inteins differ by at least one amino acid from the wild type intein.

33. The method of claim 28, wherein the test inteins differ in post-translational modification from the wild-type intein.

34. A method for identifying altered homing endonucleases that manipulate the covalent structure of macromolecules, wherein the macromolecule is a polynucleotide, and wherein the homing endonucleases have altered activity or specificity compared to the wild-type homing endonuclease, the method comprising the steps of:
providing cells comprising a polynucleotide, wherein the polynucleotide without disruption is essential for cell growth, and wherein the polynucleotide is disrupted by an inserted altered homing endonuclease cleavage site of interest, wherein the cleavage site is not recognized by a wild-type homing endonuclease;
transforming the cells with nucleic acids encoding at least one test homing endonuclease that differs from the wild-type homing endonuclease;

identifying transformed cells wherein the disruption of the polynucleotide has been removed by the test homing endonuclease.

35. The method of claim 34, wherein the cells comprise *E. coli* cells.

36. The method of claim 34, wherein the polynucleotide without disruption is on a plasmid.

37. The method of claim 34, wherein the step of identifying transformed cells comprises identifying cells that have reduced cell growth.

38. The method of claim 34, wherein the polynucleotide without disruption inhibits the function of a protein that reduces cell growth.

39. The method of claim 34, wherein the step of identifying transformed cells exhibiting a disruption in the polynucleotide comprises identifying cells wherein the test homing endonuclease removes the inserted nucleotide sequence, whereby increased cell growth indicates removal of the inserted nucleotide sequence by the test homing endonuclease.

40. The method of claim 34, wherein the polynucleotide without disruption encodes a protein that is essential for cell growth.

41. The method of claim 40, wherein the inserted nucleotide sequence encodes an intervening protein sequence.

42. The method of claim 41, wherein the step of identifying transformed cells comprises identifying cells wherein the test homing endonuclease excises the inserted nucleotide sequence encoding the intervening protein sequence, whereby increased cell growth indicates removal of the inserted nucleotide sequence by the test homing endonuclease.

43. The method of claim 34, wherein the test homing endonucleases differ by at least one amino acid from the wild type homing endonuclease.

44. The method of claim 34, wherein the test homing endonucleases differ in post-translational modification from the wild-type homing endonuclease.

45. The method of claim 34, wherein the polynucleotide is DNA.

* * * * *

SEQUENCE LISTING

```
<160> NUMBER OF SEQ ID NOS: 37

<210> SEQ ID NO 1
<211> LENGTH: 18
<212> TYPE: DNA
<213> ORGANISM: Artificial
<220> FEATURE:
<223> OTHER INFORMATION: Recognition sequence of homing endonuclease
      I-SceI

<400> SEQUENCE: 1
```

-continued tagggataac agggtaat                                          18

<210> SEQ ID NO 2
<211> LENGTH: 18
<212> TYPE: DNA
<213> ORGANISM: Artificial
<220> FEATURE:
<223> OTHER INFORMATION: Mutant of recognition sequence of homing
      endonuclease I-SceI

<400> SEQUENCE: 2
tagggataac aaggtaat                                          18

<210> SEQ ID NO 3
<211> LENGTH: 16
<212> TYPE: DNA
<213> ORGANISM: Artificial
<220> FEATURE:
<223> OTHER INFORMATION: Recognition sequence of homing endonuclease
      I-ScaI

<400> SEQUENCE: 3
tgaggtgcac tagtta                                            16

<210> SEQ ID NO 4
<211> LENGTH: 16
<212> TYPE: DNA
<213> ORGANISM: HIV-1

<400> SEQUENCE: 4
tgaggtgcac tattat                                            16

<210> SEQ ID NO 5
<211> LENGTH: 38
<212> TYPE: DNA
<213> ORGANISM: Artificial
<220> FEATURE:
<223> OTHER INFORMATION: PCR-primer for amplifying SupE cassette

<400> SEQUENCE: 5
tatgcataac gcggccgccc cgagggcacc tgtcctac                    38

<210> SEQ ID NO 6
<211> LENGTH: 32
<212> TYPE: DNA
<213> ORGANISM: Artificial
<220> FEATURE:
<223> OTHER INFORMATION: PCR primer for amplifying SupE cassette

<400> SEQUENCE: 6
tatctgggta ccgcatgcac cattccttgc gg                          32

<210> SEQ ID NO 7
<211> LENGTH: 37
<212> TYPE: DNA
<213> ORGANISM: Artificial
<220> FEATURE:
<223> OTHER INFORMATION: PCR primer for amplifying I-SceI homing
      endonuclease

<400> SEQUENCE: 7
agctccatgg caatgaaaaa catcaaaaaa aaccagg                     37

<210> SEQ ID NO 8
<211> LENGTH: 42
<212> TYPE: DNA

```
<213> ORGANISM: Artificial
<220> FEATURE:
<223> OTHER INFORMATION: PCR primer for amplifying I-SceI homing
      endonuclease

<400> SEQUENCE: 8
tatcaaatgc ggccgcttat tatttcagga aagtttcgga gg                          42

<210> SEQ ID NO 9
<211> LENGTH: 32
<212> TYPE: DNA
<213> ORGANISM: Artificial
<220> FEATURE:
<223> OTHER INFORMATION: PCR primer for amplifying I-SceI homing
      endonuclease

<400> SEQUENCE: 9
agctccatgg aatataccat gctgattaaa ag                                     32

<210> SEQ ID NO 10
<211> LENGTH: 37
<212> TYPE: DNA
<213> ORGANISM: Artificial
<220> FEATURE:
<223> OTHER INFORMATION: PCR primer for amplifying I-SceI homing
      endonuclease

<400> SEQUENCE: 10
tatcaaatgc ggccgcttat tacagatagt tgcccag                                37

<210> SEQ ID NO 11
<211> LENGTH: 31
<212> TYPE: DNA
<213> ORGANISM: Artificial
<220> FEATURE:
<223> OTHER INFORMATION: PCR primer for amplifying PI-SceI homing
      endonuclease

<400> SEQUENCE: 11
agctccatgg gatccgcatg ctttgccaaa g                                      31

<210> SEQ ID NO 12
<211> LENGTH: 41
<212> TYPE: DNA
<213> ORGANISM: Artificial
<220> FEATURE:
<223> OTHER INFORMATION: PCR primer for amplifying PI-SceI homing
      endonuclease

<400> SEQUENCE: 12
tatcaaatgc ggccgctcat cagcaattat ggacgacaac c                           41

<210> SEQ ID NO 13
<211> LENGTH: 64
<212> TYPE: DNA
<213> ORGANISM: Artificial
<220> FEATURE:
<223> OTHER INFORMATION: Recognition site of PI-SceI homing endonuclease

<400> SEQUENCE: 13
tgacgccatt atctatgtcg ggtgcggaga aagaggtaat gaaatggcag aagtcttgat       60
ggat                                                                   64

<210> SEQ ID NO 14
<211> LENGTH: 71
<212> TYPE: DNA
```

<213> ORGANISM: Artificial
<220> FEATURE:
<223> OTHER INFORMATION: Recognition site of PI-SceI homing endonuclease

<400> SEQUENCE: 14
gatcatccat caagacttct gccatttcat tacctctttc tccgcacccg acatagataa    60
tggcgtcaga t    71

<210> SEQ ID NO 15
<211> LENGTH: 34
<212> TYPE: DNA
<213> ORGANISM: Artificial
<220> FEATURE:
<223> OTHER INFORMATION: Recombination sequence designated loxP

<400> SEQUENCE: 15
ataacttcgt atagcataca ttatacgaag ttat    34

<210> SEQ ID NO 16
<211> LENGTH: 34
<212> TYPE: DNA
<213> ORGANISM: Artificial
<220> FEATURE:
<223> OTHER INFORMATION: Recombination sequence designated loxP

<400> SEQUENCE: 16
ataacttcgt ataatgtatg ctatacgaag ttat    34

<210> SEQ ID NO 17
<211> LENGTH: 34
<212> TYPE: DNA
<213> ORGANISM: Artificial
<220> FEATURE:
<223> OTHER INFORMATION: Recombination sequence designated FRT

<400> SEQUENCE: 17
gaagttccta ttctctagaa agtataggaa cttc    34

<210> SEQ ID NO 18
<211> LENGTH: 34
<212> TYPE: DNA
<213> ORGANISM: Artificial
<220> FEATURE:
<223> OTHER INFORMATION: Recombination sequence designated FRT

<400> SEQUENCE: 18
gaagttccta tactttctag agaataggaa cttc    34

<210> SEQ ID NO 19
<211> LENGTH: 18
<212> TYPE: DNA
<213> ORGANISM: Artificial
<220> FEATURE:
<223> OTHER INFORMATION: Recognition sequence of homing endonuclease
      I-SceI

<400> SEQUENCE: 19
attaccctgt tatccta    18

<210> SEQ ID NO 20
<211> LENGTH: 16
<212> TYPE: DNA
<213> ORGANISM: Artificial
<220> FEATURE:
<223> OTHER INFORMATION: Recognition sequence of homing endonuclease
      I-ScaI

```
<400> SEQUENCE: 20
taactagtgc acctca                                              16

<210> SEQ ID NO 21
<211> LENGTH: 30
<212> TYPE: DNA
<213> ORGANISM: Artificial
<220> FEATURE:
<223> OTHER INFORMATION: Recognition sequence of homing endonuclease
      PI-SceI

<400> SEQUENCE: 21
ttatctatgt cgggtgcgga gaaagaggta                               30

<210> SEQ ID NO 22
<211> LENGTH: 30
<212> TYPE: DNA
<213> ORGANISM: Artificial
<220> FEATURE:
<223> OTHER INFORMATION: Recognition sequence of homing endonuclease
      PI-SceI

<400> SEQUENCE: 22
tacctctttc tccgcacccg acatagataa                               30

<210> SEQ ID NO 23
<211> LENGTH: 34
<212> TYPE: DNA
<213> ORGANISM: Artificial
<220> FEATURE:
<223> OTHER INFORMATION: Mutant FRT target sequence

<400> SEQUENCE: 23
gaagattcta ctgtctagaa acagtagaat cttc                          34

<210> SEQ ID NO 24
<211> LENGTH: 34
<212> TYPE: DNA
<213> ORGANISM: Artificial
<220> FEATURE:
<223> OTHER INFORMATION: Mutant FRT target sequence

<400> SEQUENCE: 24
gaagattcta ctgtttctag acagtagaat cttc                          34

<210> SEQ ID NO 25
<211> LENGTH: 18
<212> TYPE: DNA
<213> ORGANISM: Artificial
<220> FEATURE:
<223> OTHER INFORMATION: Mutant recognition sequence of homing
      endonuclease I-SceI

<400> SEQUENCE: 25
attaccttgt tatcccta                                            18

<210> SEQ ID NO 26
<211> LENGTH: 16
<212> TYPE: DNA
<213> ORGANISM: HIV-1 gp 120

<400> SEQUENCE: 26
tgaggtgcac tattat                                              16
```

```
<210> SEQ ID NO 27
<211> LENGTH: 16
<212> TYPE: DNA
<213> ORGANISM: HIV-1 gp 120

<400> SEQUENCE: 27
atattagtgc acctca                                                      16

<210> SEQ ID NO 28
<211> LENGTH: 19
<212> TYPE: DNA
<213> ORGANISM: Artificial
<220> FEATURE:
<223> OTHER INFORMATION: Target extended I-SceI cleavage site for
      pSites+ vector

<400> SEQUENCE: 28
tagggataac agggtaatg                                                   19

<210> SEQ ID NO 29
<211> LENGTH: 19
<212> TYPE: DNA
<213> ORGANISM: Artificial
<220> FEATURE:
<223> OTHER INFORMATION: Target extended I-SceI cleavage for pSites+
      vector

<400> SEQUENCE: 29
cattaccctg ttatccta                                                    19

<210> SEQ ID NO 30
<211> LENGTH: 19
<212> TYPE: DNA
<213> ORGANISM: Artificial
<220> FEATURE:
<223> OTHER INFORMATION: Non-target extended I-SceI cleavage sites for
      pSite- vector

<400> SEQUENCE: 30
tagggataac agggtaata                                                   19

<210> SEQ ID NO 31
<211> LENGTH: 19
<212> TYPE: DNA
<213> ORGANISM: Artificial
<220> FEATURE:
<223> OTHER INFORMATION: Non-target extended I-SceI cleavage sites for
      pSites- vector

<400> SEQUENCE: 31
tattaccctg ttatccta                                                    19

<210> SEQ ID NO 32
<211> LENGTH: 19
<212> TYPE: DNA
<213> ORGANISM: Artificial
<220> FEATURE:
<223> OTHER INFORMATION: Non-target extended I-SceI cleavage sites for
      pSites- vector

<400> SEQUENCE: 32
tagggataac agggtaatt                                                   19

<210> SEQ ID NO 33
<211> LENGTH: 19
<212> TYPE: DNA
<213> ORGANISM: Artificial
```

```
<220> FEATURE:
<223> OTHER INFORMATION: Non-target extended I-SceI cleavage sites for
      pSites- vector

<400> SEQUENCE: 33
aattaccctg ttatcccta                                                  19

<210> SEQ ID NO 34
<211> LENGTH: 19
<212> TYPE: DNA
<213> ORGANISM: Artificial
<220> FEATURE:
<223> OTHER INFORMATION: Non-target extended I-SceI cleavage sites for
      pSites- vector

<400> SEQUENCE: 34
tagggataac agggtaatc                                                  19

<210> SEQ ID NO 35
<211> LENGTH: 19
<212> TYPE: DNA
<213> ORGANISM: Artificial
<220> FEATURE:
<223> OTHER INFORMATION: Non-target extended I-SceI cleavage sites for
      pSites- vector

<400> SEQUENCE: 35
gattaccctg ttatcccta                                                  19

<210> SEQ ID NO 36
<211> LENGTH: 9
<212> TYPE: PRT
<213> ORGANISM: Artificial
<220> FEATURE:
<223> OTHER INFORMATION: Protein

<400> SEQUENCE: 36

Leu Ala Gly Leu Ile Asp Ala Asp Gly
1               5

<210> SEQ ID NO 37
<211> LENGTH: 12
<212> TYPE: PRT
<213> ORGANISM: Artificial
<220> FEATURE:
<223> OTHER INFORMATION: Translation of 34 base pair loxP "footprint"

<400> SEQUENCE: 37

Ile Thr Ser Tyr Ser Ile His Tyr Thr Lys Leu Ser
1               5                   10
```